US007323334B2

(12) United States Patent
Zhou et al.

(10) Patent No.: US 7,323,334 B2
(45) Date of Patent: Jan. 29, 2008

(54) SCREENING AND THERAPEUTIC METHODS RELATING TO NEUROGENESIS

(75) Inventors: Qun-Yong Zhou, Irvine, CA (US); Michelle Y. Cheng, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 471 days.

(21) Appl. No.: 10/680,554

(22) Filed: Oct. 3, 2003

(65) Prior Publication Data
US 2004/0229291 A1 Nov. 18, 2004

Related U.S. Application Data

(60) Provisional application No. 60/416,202, filed on Oct. 4, 2002.

(51) Int. Cl.
C12N 5/02 (2006.01)
A61K 38/00 (2006.01)
(52) U.S. Cl. ............... 435/377; 435/325; 435/354; 435/365; 435/368; 512/12
(58) Field of Classification Search ............. None
See application file for complete search history.

(56) References Cited

U.S. PATENT DOCUMENTS

| 6,756,479 B2 | 6/2004 | Sheppard et al. |
| 2002/0106731 A1 | 8/2002 | Ruben et al. |
| 2002/0115610 A1 | 8/2002 | Zhou et al. |
| 2002/0165380 A1 | 11/2002 | Bard |
| 2003/0203847 A1 | 10/2003 | Rosenfeld et al. |
| 2004/0229291 A1 | 11/2004 | Matsumoto et al. |

FOREIGN PATENT DOCUMENTS

| EP | 1207198 | 5/2002 |
| EP | 1302542 | 4/2003 |
| WO | WO 98/46620 | 10/1998 |
| WO | WO 99/63088 | 12/1999 |
| WO | WO 00/34334 | 6/2000 |
| WO | WO 00/52022 | 9/2000 |
| WO | WO 01/16309 | 3/2001 |
| WO | WO 01/36465 | 5/2001 |
| WO | WO 01/36471 | 5/2001 |
| WO | WO 01/48188 | 7/2001 |
| WO | WO 01/53308 | 7/2001 |
| WO | WO 02/06483 | 1/2002 |
| WO | WO 02/36625 A2 | 5/2002 |
| WO | WO 2004/031367 | 4/2004 |

OTHER PUBLICATIONS

Ng et al., Science Jun. 24, 2005: vol. 308. No. 5730, pp. 1923-1927.*
Burstein et al, "Structure/function relationships of a G-protein coupling pocket formed by the third intracellular loop of the m5 muscarinic receptor," *Biochemistry*. 37(12):4052-4058 (1998).
Burstein et al., The second intracellular loop of the m5 muscarinic receptor is the switch which enables G-protein coupling. *J Biol Chem.* 273(38):24322-24327 (1998).
Cao et al., "Stem cell repair of central nervous system injury," *J Neurosci Res.* 68(5):501-510 (2002).
Bullock et al., "Identification of Two Prokineticin cDNAs: Recombinant Proteins Potently Contract Gastrointestinal Smooth Muscle." *Society for Neuroscience Abstracts* 27(2):2226 (2001).
Cheng et al., "Prokineticin 2 transmits the behavioural circadian rhythm of the suprachiasmatic nucleus," *Nature.* 417(6887):405-410 (2002).
Conklin et al., "Substitution of three amino acids switches receptor specificity of Gq alpha to that of Gi alpha," *Nature.* 363(6426):274-276 (1993).
Cunningham et al., "Actin-binding protein requirement for cortical stability and efficient locomotion," *Science.* 255(5042):325-327 (1992).
Hunziker et al., "Nestin-expressing cells in the pancreatic islets of Langerhans," *Biochem Biophys Res Commun.* 271(1):116-119 (2000).
Klassen et al., "Surface markers expressed by multipotent human and mouse neural progenitor cells include tetraspanins and non-protein epitopes," *Neurosci Lett.* 312(3):180-182 (2001).
Komatsuzaki et al., "A novel system that reports the G-proteins linked to a given receptor: a study of type 3 somatostatin receptor," *FEBS Lett.* 406(1-2):165-170 (1997).
LeCouter et al., "Identification of an angiogenic mitogen selective for endocrine gland endothelium," *Nature.* 412(6850):877-884 (2001).
Le Poul et al., "Adaptation of aequorin functional assay to high throughput screening," *J Biomol Screen.* 7(1):57-65 (2002).
Lin et al., "Identification and molecular characterization of two closely related G protein-coupled receptors activated by prokineticins/endocrine gland vascular endothelial growth factor," *J Biol Chem.* 277(22):19276-19280 (2002).
Masuda et al., "Isolation and identification of EG-VEGF/prokineticins as cognate ligands for two orphan G-protein-coupled receptors," *Biochem Biophys Res Commun.* 293(1):396-402 (2002).

(Continued)

Primary Examiner—David Romeo
Assistant Examiner—Daniel C Gamett
(74) Attorney, Agent, or Firm—DLA Piper US LLP

(57) ABSTRACT

The invention provides methods of identifying compounds that modulate neurogenesis. The methods involve providing a compound that modulates prokineticin receptor signaling; contacting a neural stem or progenitor cell with the compound; and determining the ability of the compound to modulate neurogenesis. The invention also provides methods for modulating neurogenesis. The methods involve contacting a neural stem or progenitor cell with an effective amount of a compound that modulates prokineticin receptor signaling. Such methods are useful for both ex vivo or in vivo therapeutic applications where neural regeneration is desirable.

9 Claims, 20 Drawing Sheets

OTHER PUBLICATIONS

Mellentin-Michelotti et al., "Determination of ligand binding affinities for endogenous seven-transmembrane receptors using fluorometric microvolume assay technology," *Anal Biochem.* 272(2):182-190 (1999).

Mollay et al., "Bv8, a small protein from frog skin and its homologue from snake venom induce hyperalgesia in rats," *Eur J Pharmacol.* 374(2):189-196 (1999).

Okano et al., "Stem cell biology of the central nervous system," *J Neurosci Res.* 69(6):698-707 (2002).

Park et al., "Global gene and cell replacement strategies via stem cells," *Gene Ther.* 9(10):613-624 (2002).

Rees et al., "Development of a homogeneous MAP kinase reporter gene screen for the identification of agonists and antagonists at the CXCR1 chemokine receptor," *J Biomol Screen.* 6(1):19-27 (2001).

Schweitz et al., "MIT(1), a black mamba toxin with a new and highly potent activity on intestinal contraction," *FEBS Lett.* 461(3):183-188 (1999).

Tate et al., "Heterologous expression of G-protein-coupled receptors," *Trends Biotechnol.* 14(11):426-430 (1996).

Van der Wal et al., "Monitoring agonist-induced phospholipase C activation in live cells by fluorescence resonance energy transfer," *J Biol Chem.* 276(18):15337-15344 (2001).

Wechselberger et al., "The mammalian homologues of frog Bv8 are mainly expressed in spermatocytes," *FEBS Lett.* 462(1-2):177-181 (1999).

Zhang et al., "A scintillation proximity assay for human interleukin-5 (hIL-5) high-affinity binding in insect cells coexpressing hIL-5 receptor alpha and beta subunits," *Anal Biochem.* 268(1):134-142 (1999).

Zuck et al., "Ligand-receptor binding measured by laser-scanning imaging," *Proc. Natl. Acad. Sci. USA.* 96(20):11122-11127 (1999).

GenBank Accession No. AF487278, Jun. 9, 2002.
GenBank Accession No. AF487279, Jun. 9, 2002.
GenBank Accession No. AF487280, Jun. 9, 2002.

* cited by examiner

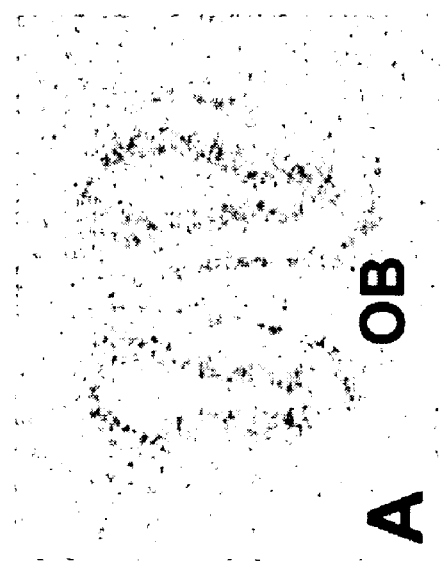
FIGURE 4

SEQ ID NO:1
human PKR1, GenBank Accession No. AAM48127

```
  1 METTMGFMDD NATNTSTSFL SVLNPHGAHA TSFPFNFSYS DYDMPLDEDE DVTNSRTFFA
 61 AKIVIGMALV GIMLVCGIGN FIFIAALVRY KKLRNLTNLL IANLAISDFL VAIVCCPFEM
121 DYYVVRQLSW EHGHVLCTSV NYLRTVSLYV STNALLAIAI DRYLAIVHPL RPRMKCQTAT
181 GLIALVWTVS ILIAIPSAYF TTETVLVIVK SQEKIFCGQI WPVDQQLYYK SYFLFIFGIE
241 FVGPVVTMTL CYARMTRELW FKAVPGFQTE QIRKRLRCRR KTVLVLMCIL TAYVLCWAPF
301 YGFTIVRDFF PTVFVKEKHY LTAFYIVECI AMSNSMINTL CFVTVKNDTV KYFKKIMLLH
361 WKASYNGGKS SADLDLKTIG MPATEEVDCI RLK
```

SEQ ID NO:2
human PKR2, GenBank Accession No. AAM48128

```
  1 MAAQNGNTSF TPNFNPPQDH ASSLSFNFSY GDYDLPMDED EDMTKTRTFF AAKIVIGIAL
 61 AGIMLVCGIG NFVFIAALTR YKKLRNLTNL LIANLAISDF LVAIICCPFE MDYYVVRQLS
121 WEHGHVLCAS VNYLRTVSLY VSTNALLAIA IDRYLAIVHP LKPRMNYQTA SFLIALVWMV
181 SILIAIPSAY FATETVLFIV KSQEKIFCGQ IWPVDQQLYY KSYFLFIFGV EFVGPVVTMT
241 LCYARISREL WFKAVPGFQT EQIRKRLRCR RKTVLVLMCI LTAYVLCWAP FYGFTIVRDF
301 FPTVFVKEKH YLTAFYVVEC IAMSNSMINT VCFVTVKNNT MKYFKKMMLL HWRPSQRGSK
361 SSADLDLRTN GVPTTEEVDC IRLK
```

SEQ ID NO:3
mouse PKR1, GenBank Accession No. AAM49570

```
  1 METTVGALGE NTTDTFTDFF SALDGHEAQT GSLPFTFSYG DYDMPLDEEE DVTNSRTFFA
 61 AKIVIGMALV GIMLVCGIGN FIFITALARY KKLRNLTNLL IANLAISDFL VAIVCCPFEM
121 DYYVVRQLSW EHGHVLCASV NYLRTVSLYV STNALLAIAI DRYLAIVHPL RPRMKCQTAA
181 GLIFLVWSVS ILIAIPAAYF TTETVLVIVE RQEKIFCGQI WPVDQQFYYR SYFLLVFGLE
241 FVGPVVAMTL CYARVSRELW FKAVPGFQTE QIRRTVRCRR RTVLGLVCVL SAYVLCWAPF
301 YGFTIVRDFF PSVFVKEKHY LTAFYVVECI AMSNSMINTL CFVTVRNNTS KYLKRILRLQ
361 WRASPSGSKA SADLDLRTTG IPATEEVDCI RLK
```

SEQ ID NO:4
mouse PKR2, GenBank Accession No. AAM49571

```
  1 MGPQNRNTSF APDLNPPQDH VSLNYSYGDY DLPLGEDEDV TKTQTFFAAK IVIGVALAGI
 61 MLVCGIGNFV FIAALARYKK LRNLTNLLIA NLAISDFLVA IVCCPFEMDY YVVRQLSWAH
121 GHVLCASVNY LRTVSLYVST NALLAIAIDR YLAIVHPLKP RMNYQTASFL IALVWMVSIL
181 IAVPSAYFTT ETILVIVKNQ EKIFCGQIWS VDQQLYYKSY FLFVFGLEFV GPVVTMTLCY
241 ARISQELWFK AVPGFQTEQI RKRLRCRRKT VLLLMGILTA YVLCWAPFYG FTIVRDFFPT
301 VVVKEKHYLT AFYVVECIAM SNSMINTICF VTVKNNTMKY FKKMLRLHWR PSHYGSKSSA
361 DLDLKTSGVP ATEEVDCIRL K
```

FIGURE 6-1

SEQ ID NO:5
human PK1, GenBank Accession No. P58294

AVITGACERDV QCGAGTCCAI SLWLRGLRMC TPLGREGEEC HPGSHKVPFF RKRKHHTCPC
LPNLLCSRFP DGRYRCSMDL KNINF

SEQ ID NO:6
human PK2, isoform 1, GenBank Accession No. Q9HC23

AVI TGACDKDSQC GGGMCCAVSI WVKSIRICTP MGKLGDSCHP LTRKNNFGNG RQERRKRKRS
KRKKEVPFFG RRMHHTCPCL PGLACLRTSF NRFICLAQK

SEQ ID NO:7
human PK2, isoform 2, GenBank Accession No. Q9HC23

AVI TGACDKDSQC GGGMCCAVSI WVKSIRICTP MGKLGDSCHP LTRK VPFFG RRMHHTCPCL
PGLACLRTSF NRFICLAQK

SEQ ID NO:8
mouse PK1, GenBank Accession No. AAM49573

(AVITG) ACERDIQCGA GTCCAISLWL RGLRLCTPLG REGEECHPGS HKIPFLRKRQ HHTCPCSPSL
LCSRFPDGRY RCFRDLKNAN F

SEQ ID NO:9
mouse PK2, GenBank Accession No. AAM49572

AVIT GACDKDSQCG GGMCCAVSIW VKSIRICTPM GQVGDSCHPL TRKVPFWGRR MHHTCPCLPG
LACLRTSFNR FICLARK

SEQ ID NO:10
rat PK1, GenBank Accession No. AAM09104

A VITGACERDV QCGAGTCCAI SLWLRGLRLC TPLGREGEEC HPGSHKIPFF RKRQHHTCPC
SPSLLCSRFP DGRYRCSQDL KNVNF

SEQ ID NO:11
rat PK2, GenBank Accession No. AAM09105

AVIT GACDKDSQCG GGMCCAVSIW VKSIRICTPM GQVGDSCHPL TRKVPFWGRR MHHTCPCLPG
LACLRTSFNR FICLARK

FIGURE 6-2

SEQ ID NO:12
MIT1 (black mamba snake prokineticin), GenBank Accession
No. P25687

AVITGACERD LQCGKGTCCA VSLWIKSVRV CTPVGTSGED CHPASHKIPF SGQRKMHHTC
PCAPNLACVQ TSPKKFKCLS K

SEQ ID NO:13
Bv8 (Bombina variegata prokineticin), GenBank Accession No.
Q9PW66

A VITGACDKDV QCGSGTCCAA SAWSRNIRFC IPLGNSGEDC HPASHKVPYD GKRLSSLCPC
KSGLTCSKSG EKFKCS

SEQ ID NO:14
Bv8 homolog (Bombina maxima prokineticin), GenBank
Accession No. AAN03822

A VITGACDRDV QCGSGTCCAA SLWSRNIRFC VPLGNNGEEC HPASHKVPYN GKRLSSLCPC
KSGLTCSKSG EKFQCS

SEQ ID NO:15
human PK1/PK2 chimera

AVITGACERDVQCGAGTCCAISLWLRGLRMCTPLGREGEECHPGSHKVPFFGRRMHHTCPCLPGLACLRTSFNRF
ICLAQK

SEQ ID NO:16
human PK2/PK1 chimera

AVITGACDKDSQCGGGMCCAVSIWVKSIRICTPMGKLGDSCHPLTRKVPFFRKRKHHTCPCLPNLLCSRFPDGRY
RCSMDLKNINF

SEQ ID NO:17
human PK1 promoter region

AATAAATAAATAGATGAATACTCGCAAAATCGTATGATGTAAATGCTATTCTTATCCCATGTTATAGATAGGAAA
ACTGAGGCTTGGAGAGATTAGCAATATTTTCAAGGTCATGAAGCCATCGATCTGAATCAAAGCATCTGCCTCTGG
GGGCTTAGCTCCCAGCTCCCGTGCTAGTTAACCTTCCTCTCTGCACTCATAAATGCCTATCAGCGTTTCAATGTG
GAAACCCTAGACCCCTGTGACATTTGATAAGAAAGGTTTTGTGGATGAATCTGCTTGTGAAATACTACAAACTGC
ATTTCCCACTTGGTGTTTCAAACACTTATTAGCATATGAAAGGCCCTGAAAAGTTCTGCAAAAAACAAGCCGGTT
TGTGTTTCCCAAATTTTTGACTGTAGAAGTCTTTTATTTGTTTATTTGtGTATTAACATATTGCAACACATACCT

FIGURE 6-3

```
TGGGAAATGTTGGCTTTTATTACTGTGGAGAGAAGGCAGATCATCTGACAAAGCACTGGGAGCTCTCTCTGGGTC
GTATGACACAGAGAGGGCTGGGGTCAGGGGCTTCCCTCACAGGCGGAGGGGCCATCCCGAAAGTCAACTTCCCAC
CAGACTGGCATCTGAGACCACCGTGTTTATACACTCACGGATAAGGCCACTCTCATGCTCACCCCTAAAACTGGA
AGGCCAGTGGTGTGGCTCTGGTACCTTTCAGCCACAGCCCATACCAGCTCGGCTCTGCAGGGTACTGAGAGAGTG
TGTGCCCTGTATGTTTGCTGGCTTTCTGCCCTTGGGTCATTGTACCAAGGGACACTTGCTGGTGTTCATCCTGAG
CCCATGAGAGAGCAAATCCTTATGTGTGTGTCACTTAGGAACATCAGCCCCACAAGTCTGGTCTTTTTTTCCTCA
CTGTCTTATGGCTCCTCACTATAATTTTAACCTTTTAGAGAAATAAGGATACCACCTCACCCTCTTCTGTCTTCT
CAGCTACCTCTGTGTTGAGCCCATGGTAAATGCCTAGATAAGTCTTGGTGTGAGTGAGAGGGAACCAATAATCTT
GTATGTTGCATAGTTTGGTGCAGGGAAGCATAAATGGTGATGTTGCAAATCCCTTAATTCATTACCAGAGGCTTT
CCTCTGCCCCAAGTAGGATAGAAGGATACCCAGAGGCAGAAAAGAACATTGAGTGAAATATACATAACTGTCTGA
ATCACTGCGTTCTTGGGAGAGTTAGAGCAACCGTCAAGCCCCCCAAGTATCCATTTTTATTGGTTTTGATGTTG
ATTTGATGTTGTTAGAGATTCAGGTCTCATCTTCGCTTCTGAGATCATCTGAGTAACATCGGTGTTGGAGAAGGG
AAGAGCAGAGATGAGGCATCCACAGGCAGCCCTGGATCCTGAGTGTAAACATCTGGGAGGAGGCGGGGGATGCAG
GAGAGCCTGGCCTCCCCAGCTTGCCAGGCACAAGGCTGAGCGGGAGGAAGCGAGAGGCATCTAAGCAGGCAGTGT
TTTGCCTTCACCCCAAGTGACCATGAGAGGTGCCACGCGAGTCTCAATCATGCTCCTCCTAGTAACTGTGTCTGA
CTGTGCTGTGATCACAGGGGTAA
```

SEQ ID NO:18
mouse PK2 promoter region (GenBank Accession No. AF500108)

```
ACACAAGAAAGAAGAGGGAAGAGTGTTCTAGACCATCCTGAAAGTAGATAGCCATAGAT
CAGTGGCCCAGGCTCTGCACTACTGTTCTCTGGCAAGTCACATGTGGAGGCTCAGAAAC
ATCTGAGATTTGTGGAAACAAGTTTAAAGATTGAGTATATGGAATACTCCCACCAAATT
GCTGTGTCTTACTTCTAGTTATTGGCCACCCAAGGTTTTTATGGCAATGTTATAAATTT
GAAGAGAAACTCTAACAGTTAAAAGCTTGGCACCAGAGCACACTGGGTTTAAATCTAGT
TTCTTTCCTTAGCAATTACCCTGGCTTGAGATGGCATGGTTGACCTTTCTAAATTCCAC
TTTGCTCTTCCATAATGGCCAAGAGTTCTACCCAGAGGGTCCCTGGGGTTTTTATAGAA
GATGTACTGGAATTCACAAAGTACTTACTGTGTGCAACGCATAGCTCTGCACTTTTGAA
ATGAAAACACCACAATTGGCTTGTGCCCCAAAACAAAGAAACAAAACAAAATAAAGCTA
GGAGTCATAATGTGAACCCTAGTTCCCTAGCAAGCCTCCTGCCTCAGCTTCCTGAATGC
TGGGATTTCAAGCTAAGAGCCACCACATCTGGTTATAAAAGTTTTGTACCTATTATTTC
ATATGTATATGAATATGTCTTGTTACTTCTTCTAGGTCCTTTCCTTCTTTAAATGTTGC
TGAATGAGGTTTATTTCGCTGTGATAGATAGTTCCTGTTGACCTGAAAGGATGATAAAG
TAACTACCTAGTCATGGTTTTTAATCTTAAGAAAACCCCTTTCTTAGGTGAGACTTCTT
TTTTTTCCATCTGGAAAGTTACCAAATACGCCACACATTTGCATAACAATCTCTTTGAA
TGAAGACAGCAGCGCACGCAGCACCAGCTTTTGCCTTTAGGGCCATCTTCAATAGAAAA
AAAATAAAAAAATAAAAAAGCTGACAGAGAAGAGCAGCGAACGTTATAATGAGAACAT
CTGAATCTTTTAGAACCAAATGTTCTTCGGTGACCCTTCATATTATCTCAAAGTCACGG
TGTGCTAATTGCTTGAAGAAAACCCTTTCTCCGGGATTAATACTTCAGCTATTTAAAA
ATAGATAAACTTTACTGTACATTATCACTTGAATGGAACAAATGCTTTTCAGTGCCTCC
GTAGACAATTGGCGTTCACATTGAATCCTGGTGATTTATTATTTTTTTTAAATAAAGA
GAAAATCATCAGCATTGAACTAGATTAAAATAGACATCTTATTTAGAATTATAAAAGCC
```

FIGURE 6-4

```
ATTCCTTTTTCATGTCACATTTAAAATACGGTTATTATTTTAGAATGATAGCACAGATG
ATATTATAGGTTTAACAAGAAGAGCCACGTGGAACAGTGCCTCAATAAAGGATGAAGGC
AAAGTAGAAGGAGAATATCCATCTTATTTCATTTGACTTTTTTTTGGAACAAATCTA
AATGAAAAGTCATTTACACAAAGGCAAATAAAACCCAGTAATGAAATTACCGGGCCCAC
CTATTGTGTTACCATAATAAGCCATAAGAAAAGACGCATGCAAAGTAAGGTTTCAGCA
AAGCCAGAGTCACTCTTAACAACAGAGCCATGTGAGGAAGCGTCTGGAACAGTTTCCTC
TTCTGTGGCTGAGAAATGCCTGACACTTTCCGTGCAAGATGGAGAGCAAGGCCTGTGT
TTCTTGATCTTTCTTTGATAACCTCATCACTCTTGATGAAGCATCTACTGTGTGCTGGA
TCATTGGAATCAGTTATAGTAAGGTTAATATGCAAAATAGCAATCAGTAAGCCAGAACT
TTGGGCAATATCCGAAAGTCCAAAAGAATGTGGATTACATCAGTGAGTTGGAGTCTGCG
CAGTACATCTCACAGGAAGTTCAAGCAAAGACAGTGGAGGCAAGATCAGTAAGAGTTTG
TAAAACTGCAGTATGAGACAGTACAGAGACTCTAGGCTCTTTTTTTTTTTTAAACACA
TGAATCTAGAAACAACAGAGCTGGAAAATAGCCCAGTCATAAGCACAACAAACTAATTT
GCTCACTAGGACCCAATGTGAAGCAAGCCAGACTGATGGGTGGTATACACACATCATCC
ACTGTGTTTGTTCACAAGAACCCGTGCAAAATAAGCTGGACCAGCGATGGTATAGTATA
CACATATCATCTCAGGCAGAGACAGGCAGATCTCTGGGGCTCGCTGGCCAGCCAACCTA
GCTTACCCGGTGAGTCCCAGGCCTAGTGAAAGACCCTATCTCAGAAAGAAGGTAGAAG
GCTCTTGAAGAATGTCAGCTGGGGCTGTCCCTGGCCTCCACATGCAAAGACGCAGTGT
GTGCCCACGAATGCGCACACACACACACACAACGAGGAATCAGCAAGCTTTCTCTAC
ACTAGCAGATAGAAGATATTTTTGGCTTTTCCAATCATGTGGTCTCACAAGTACTCAG
TAAAAAGCAGACACGGGCAATACAGAAACAGGCATGGCTAGATAGAACATAAAAAATAA
ATAATAGATAGATAGATAGATAGATAGATAGATAGATAGATAGATAGATAGATAGAATA
CTGGCTAGTTTTGTGTCAACTTGACACAGCTGGAGTTATCACAGAGAGGGGAGCTTCAG
TTGGGGAAATGCCTCCATGAGATACAACTGTAAGGCATTTTCTCAATTAGTGATCAAGA
GGGAAAGGCCCCTTGTGGGTGGGACCATCTCTGGGCTGGTAGTCTTGGGTTCTATAAGA
GAGCAGGCTGAGCAAGCCAGGGGAAGGAAGACAGTAAGTAACATCCCTCCATGGCCTCT
GCATTAGCTTCTGCTTCCTGACCTGCTTGAGTTCCAGTCCTGACTTCCTTTGGTGATGA
AGAGCAGTATGGAAGTGTAAGCCGAATAAACCCTTTCCTCCCCAACTTGCTTCTTGGTC
ATCATGTTTGTACAAGAATAGAAACCCTGACTAAGACAGATAGATAGACAACAAAAGC
AATGTGTCAACGTTTTCCCAGTTTCTACTAAATCCTAGTCATTGTGGCTACATTCTATG
AAATGAAAAATTTTAAAGTCCAACAAGAAGCCACTGGTTGGCCATTTCTTTCTTTAGC
TCAGCTGCTCCCCCTCGCCCTGCCTGCCTTTGTCCAATCCCATGTAAGCACCAGAGTCC
CTCCTGCGAGCCAGTTACCACAGTGAGGTTCCTCCTTCCTCCCACTCCCAATAGTTCC
TGCCCTTCTTTCTCTTGACTGCCCACAAGGATTCTGCAGTGCTCTGCCTTCAGGAGATG
GATGGTGACTTCTCTCAGTCCTCCATCATGCTCTTCTCCACATTCCTAGTGATTTGGTC
AGCCAAAATCGAGTGCTTTGTTCAATTCTTGGTACATAGCTTGTGCTTAGTAAGTACCT
GCTGAATGAGTGAATGAATGATGGTCTATTAGTTAAAACAAAGCACTCTCAGCTTGCAC
ATTTGTACTCTTTCACCATGTATCACTTGAAGGACTAAACAAACAAATACAGACACACA
TTATCCTTTGGAGTAAGAATTACTAAGGTTGGCCAAAGTACAGTGGCTCCTTTCCTGTA
GCACTGCTTACCAGATTTCTGGTCTTAGCAGCAACTACATTTGCACTGCTGTCTTTAGC
AAGGTGAACTGTCACGTGACCCGTTTCCGTCACTGTGGCACAGTCAGGCTTGAGTTCCA
GGCAGAGGCAGCAGAAAGCTGAATTGCAACCCTCCAGCCCCACCCTTCCTTTTAGTTTC
```

FIGURE 6-5

```
CCAGAGGTTCTAGGAGAAGTGAGCAGAACTAGGTGGCATCGCACATCAGAGGTTATTTT
CTTGTAGCTCTGGATGTTAGAAGTCCAAAATCAAGGATGCTTTCCCCAGCTCTTCTGAA
TTCTGAAAGCCAGCTGTGGGGGAGGAGGTGTGTCATATCAGTCTCTATATCCAAAGATC
TTGCATCTGTTATAAAAGATGGGAAAATAGCTTAGTCAGCAAAGGGCTTGCCTCGAAA
ACATTGATGTCCTGAGTTCAGTCTCCAGAACTCAAAAAAGCCAGGTGCGGTGACTTGAG
TCTGTGGCTACCTGAGTCTGTAATCCCAACAATGGTAAAATGGGAGGCCGAGGCAGGCA
GATTTCCTGAGGCTCACAGGACAGTGAGGCTGACCTACATGTCAAAGTTCCAGTCTAGT
GAGAGACCCTGTCCCAAACAAAGGTAGAAGCCGTCTGGTACTCAAGGTTGTCTGACCT
GCACATATGCTGTGTGTAGAGGTGCCCACACATACACAATGCATACTCATGCATGCAC
AGACACACACACACACAAAACCACACTTTTAAAAAAAATGACAAAGATATCAGTTGTT
GGGTTTAGGGCATACTCTCATCCAGTATGACTTCAAGTTTGGTTGATCATATCAGCAAG
GACCCTACTTCCAAATAAAGACACAGGAACCAGGAGCTAGAGTTTCAACATAACTTTCT
AGGTGAGACTTAGTATAACCCTAGTCTGGAATCATCATAAATCATCAGTTCAAATAAAG
TCCCCCTCAGCTGAGCTCCCAGAGTGCCTGCTGTAGCTTGAATGTGTGACAGCTGTAAG
ACATGTCTCCAGGGGCCCCTCATTCCAGTCCCATATTCTTGGAGGAAACAGCAGGCGAA
TCCCCTGCACCAGGTCTCTCTTTCCCTCAAGCTTTTGCTGCCTGCATTCGTGATCCAT
GTAGATTAAGTAAGTGCATCTACACTGTGTGATTCTTGCTTCTAACCTCTCTCTGTCCC
TGATCACAAAATCCACTCCTGGTGCTCATCAATCATTGTCTGAGTGCTGGCTAATGCCA
CATGCAAGAAGGATTTTCAGGAGAAATGGACTCCTAGCCAGCACGTGTATGCGATCTAA
TTAGGTGGGCAGGACAGAAAACAGCCGTATCAGTGTTCAATGAACCTATCAGGGAAAAG
CACATGATAAGATTTAACTAGAGTGCACCCCCTTGCAGGACTTCCAGGCTATCACAGAC
TTGGTGCTTAGCACTTTCAAAGGTGTTCTCTTTGAGCTTCATGGTGGCTGGACCAGGAA
GTTGGTATTTTATGCCCACAGGGAGCCAGAGACCTTAAGAGGTCAAAGGTTCAGTTGCC
ACAAAAGACTCCAATCCAGGTCACTCTAACTTTCAAATGTAGGGTTCTTCGTATCACAC
TGTCAAACCAGCTGAGAGGTGGTAGTCATGCAAGACTGCCAGCTATATATACTCTGAAC
CCACGAAGTTTTGGTCCTCACCCAAAGGTTGTTCCTGGCTAATTTGACCACAATGACTG
ATCGAACCAACAGGTTGCAGTAACAAAACAGAACTTGAATTTCATTATTGTTTTATCGT
TGTCTTACGGTGGGGAGGAGTGTAATTCAAACAGTGTCTTTCCATTTCTAATAAATGAA
ATCAGACTTGATCTAACTTACCTGTGGGTCCAAAGAAGTTCTGTTGAAGAGTTTTCAT
TTCTTCTATCAAGTATTAAAGCCATTAAACCCTTCCAAAGAGGTTTAGGGGGTAGCCGA
GCAGTAGAATTGACCCAGGATGTCCATGCCCTTGGTTGCAACCTCAGCACAGGAAAACA
GAAGAGCCTTAAACCAGTCTTATGTTTAAGCATCTCTAACCTTGATTCAAAAGTCTTAG
GAGACTGTTTTGGGAACAGTCAATCTCAATGGAAGGTTAGCATTTCCTGGGTAGAGAT
GGCCTGTTTTCTACGCTCTGAGAAGTAGGGAATACCCAGTTGGCATTTGATAGTAACAA
ATATGAAACCGACCATTTAAGAAAAGAATTAAAAGAGTGTCAGGAATGTTAAAGTTCAT
GTTGACTGGTTTTTACATTTCCCCCGGGCTGCACTCCCATGCCTTCGTTGGCATGGAGA
CTGGAAAGGAAACTTTCCACCAGTCTGTCACTTGCTACTGTTTCCACTTAGTTTACTGT
GAATCCACTTTTAACAGTTTTCTCAAAGTTAAAAGGAGTTTGATCCCGGGTGTGTTTT
CGGTCTCAGGATGCTTCTTGAACTCAAAACATGGTACAAAAGGCTTTAAAACTCAGC
CAAAGATCTAGGGTTTGAAACGCCCAGCTGTTTAACATTCAAATAATTCCCTGGCCCTT
TGTTCATTTTTTTCCCCTCTACATTTCGTCTGAATGCTTTGGCATGAGGGAGCCCACA
GACTGAAAGTAACTGTGGCCCAGCTCTCCTTACTGTATTGATTAAAGTGGCTGAAAGG
```

FIGURE 6-6

CCCATCTGCCTTTCAGCAGTCTGTGGTCCTATGGGACATGGGAAAGTCTAAGGTCCCTA
GCTGTCTAGGAGTGAGGTGGGCTCCCCCAAACCTCAGAAAAAGTCAAATTGATCATCCT
TGTAGAAGCAAGCAAGATGAGATTATTGGAGCCAAATTAGGAACACAGAGAGGGTTGTC
TCTTGTCTCATGGGATGAATGCCTAGAGTCCAGCAGACACACCTAAGTGATTGATCAGA
ACCCCCACCACCACCACCAAAAAAAAATATATATATATGTATAAGACTTGGAGTTTCCT
AGGCTGGAGAACCGAGCTGGGAGAGAGCCACCTTCCCAGGGCCTCAGGCTGGCAGAGCA
AGCTGGGAGTTCTCCTTTTTTCCCCCTTTGGCAACATCCTGTTCTGCCTGAAGCAGGCT
GGAAGCTGCAGAGGGGAGGGAACGCACGTGAGAGAAATCAGGGCAGAAAGGGTCAGGAA
CAGATGTGGGCACCGGAGAAGTCATTTCCAAAAAGGAAAGGAGACTCCCACAGCTGGAG
GGGCAGCCGAGTCCCTCCAACTTCTTAAGAGATGTGGGACGGGGTGTGCTGGCGCTTTG
TTCTTCCAGCCTGCTATGTTCGCTTGCCCTTTGCTTGTTTGTCTGTTCTTTCTATGTTG
TGCCACCTCAGGGCAGAGCCGGTGGCAGTACCTGGCACGCACGGATCTCTCACTGTAGA
TATGCTGAACAAATGTGTACAAATACAGTGCAGTTGTGTCCGCCGCGTCTGGCACGTCG
TGGGTACCCCCTGCACATCTGTATGGCAAATGATGTGCCTCTGCGAGTGTGGGGCTGA
GCACGTGAGGCTCTGGAAAACAGGACGGCGAAGGAGGAGGGTTTCTGAGACCACAAAAG
CTTCAGGAAGGCTGGCTAGGGCTGCGGCGCCCGCGGGGCTCTGCCCGCGTGGCGCTT
TGCGCGTGGGGCGCGGGGCACGTGCGCGTGTGCGCGTGGAGCGCGGGGTGTGTGCCCGC
GCCGTGCCCCCGCGTGCTGCCTGGCGTGAGTCACCGCGGGGCTCGCCTTTATAACCGC
CGCCAGGCTCGCAGCTCCGCAGAGCAGCCCGGCC

SEQ ID NO:19
mouse PK2 promoter region (2.8 kb)

CAGCTGAGCTCCCAGAGTGCCTGCTGTAGCTTGAATGTGTGACAGCTGTAAGACATGTC
TCCAGGGGCCCCTCATTCCAGTCCCATATTCTTGGAGGAAACAGCAGGCGAATCCCCTG
CACCAGGTCTCTCTTTCCCTCTAAGCTTTTGCTGCCTGCATTCGTGATCCATGTAGATT
AAGTAAGTGCATCTACACTGTGTGATTCTTGCTTCTAACCTCTCTCTGTCCCTGATCAC
AAAATCCACTCCTGGTGCTCATCAATCATTGTCTGAGTGCTGGCTAATGCCACATGCAA
GAAGGATTTTCAGGAGAAATGGACTCCTAGCCAGCACGTGTATGCGATCTAATTAGGTG
GGCAGGACAGAAAACAGCCGTATCAGTGTTCAATGAACCTATCAGGGAAAAGCACATGA
TAAGATTTAACTAGAGTGCACCCCCTTGCAGGACTTCCAGGCTATCACAGACTTGGTGC
TTAGCACTTTCAAAGGTGTTCTCTTTGAGCTTCATGGTGGCTGGACCAGGAAGTTGGTA
TTTTATGCCCACAGGGAGCCAGAGACCTTAAGAGGTCAAAGGTTCAGTTGCCACAAAAG
ACTCCAATCCAGGTCACTCTAACTTTCAAATGTAGGGTTCTTCGTATCACACTGTCAAA
CCAGCTGAGAGGTGGTAGTCATGCAAGACTGCCAGCTATATATACTCTGAACCCACGAA
GTTTTGGTCCTCACCCAAAGGTTGTTCCTGGCTAATTTGACCACAATGACTGATCGAAC
CAACAGGTTGCAGTAACAAAACAGAACTTGAATTTCATTATTGTTTTATCGTTGTCTTA
CGGTGGGGAGGAGTGTAATTCAAACAGTGTCTTTCCATTTCTAATAAATGAAATCAGAC
TTGATCTAACTTACCTGTGGGTCCAAAGAAGTTCTGTTGAAGAGTTTTCATTTCTTCT
ATCAAGTATTAAAGCCATTAAACCCTTCCAAAGAGGTTTAGGGGGTAGCCGAGCAGTAG
AATTGACCCAGGATGTCCATGCCCTTGGTTGCAACCTCAGCACAGGAAAACAGAAGAGC
CTTAAACCAGTCTTATGTTTAAGCATCTCTAACCTTGATTCAAAGTCTTAGGAGACTG

FIGURE 6-7

```
TTTTGGGAACAGTCAATCTCAATGGAAGGTTAGCATTTCCCTGGGTAGAGATGGCCTGT
TTTCTACGCTCTGAGAAGTAGGGAATACCCAGTTGGCATTTGATAGTAACAAATATGAA
ACCGACCATTTAAGAAAAGAATTAAAAGAGTGTCAGGAATGTTAAAGTTCATGTTGACT
GGTTTTTACATTTCCCCCGGGCTGCACTCCCATGCCTTCGTTGGCATGGAGACTGGAAA
GGAAACTTTCCACCAGTCTGTCACTTGCTACTGTTTCCACTTAGTTTACTGTGAATCCA
CTTTTAACAGTTTTCTCAAAGTTAAAAAGGAGTTTGATCCCGGGTGTGTTTTCGGTCTC
AGGATGCTTCTTGAACTCAAAAACATGGTACAAAAAGGCTTTAAAACTCAGCCAAAGAT
CTAGGGTTTGAAACGCCCAGCTGTTTAACATTCAAATAATTCCCTGGCCCTTTGTTCAT
TTTTTTTCCCCTCTACATTTCGTCTGAATGCTTTGGCATGAGGGAGCCCACAGACTGAA
AGTAACTGTGGCCCAGCTCTCCTTACTGTATTGATTAAAGTGGCTGAAAAGGCCCATCT
GCCTTTCAGCAGTCTGTGGTCCTATGGGACATGGGAAAGTCTAAGGTCCCTAGCTGTCT
AGGAGTGAGGTGGGCTCCCCCAAACCTCAGAAAAGTCAAATTGATCATCCTTGTAGAA
GCAAGCAAGATGAGATTATTGGAGCCAAATTAGGAACACAGAGAGGGTTGTCTCTTGTC
TCATGGGATGAATGCCTAGAGTCCAGCAGACACACCTAAGTGATTGATCAGAACCCCCA
CCACCACCACCAAAAAAAAATATATATATATGTATAAGACTTGGAGTTTCCTAGGCTGG
AGAACCGAGCTGGGAGAGAGCCACCTTCCCAGGGCCTCAGGCTGGCAGAGCAAGCTGGG
AGTTCTCCTTTTTTCCCCCTTTGGCAACATCCTGTTCTGCCTGAAGCAGGCTGGAAGCT
GCAGAGGGGAGGGAACGCACGTGAGAGAAATCAGGGCAGAAAGGGTCAGGAACAGATGT
GGGCACCGGAGAAGTCATTTCCAAAAAGGAAAGGAGACTCCCACAGCTGGAGGGGCAGC
CGAGTCCCTCCAACTTCTTAAGAGATGTGGGACGGGGTGTGCTGGCGCTTTGTTCTTCC
AGCCTGCTATGTTCGCTTGCCCTTTGCTTGTTTGTCTGTTCTTTCTATGTTGTGCCACC
TCAGGGCAGAGCCGGTGGCAGTACCTGGCACGCACGGATCTCTCACTGTAGATATGCTG
AACAAATGTGTACAAATACAGTGCAGTTGTGTCCGCCGCGTCTGGCACGTCGTGGGTAC
CCCCTGCACATCTGTATGGCAAATGATGTGCCTCTGCGAGTGTGGGGCTGAGCACGTG
AGGCTCTGGAAAACAGGACGGCGAAGGAGGAGGGTTTCTGAGACCACAAAAGCTTCAGG
AAGGCTGGCTAGGGCTGCGGCGCCCCGCGGGGCTCTGCCCGCGTGGCGCTTTGCGCGT
GGGGCGCGGGGCACGTGCGCGTGTGCGCGTGGAGCGCGGGGTGTGTGCCCGCGCCGTGC
CCCCCGCGTGCTGCCTGGCGTGAGTCACCGCGGGGCTCGCCTTTATAACCGCCGCCAGG
CTCGCAGCTCCGCAGAGCAGCCCGGCC
```

SEQ ID NO:20
human PK2 promoter region (GenBank Accession No. AF500109)

```
TCCCATGAGATGGTAAGCTCCCAGGGGGCTGGGTTCATGTCTGTTTTGCTCACCCTCGT
ACCCCCAATGCTGCACACAATATCTGGAATATAGTAAGTCTTAGTTAATACCTGTTGAA
TGAATAAATTATGGTTTTCTACCCACCTAAAAGAAAATATTAGCTTACACATTTACTCA
CTTTCAGAGTCTTTGTATAATTCTGGTATAAAGAATGCTGTACTAGAAAAATACAAAG
GAAATTACACATTATTATTTATAATAGCAATTACTAATATAATTCAAGTTCATTATGC
TCATTAAGGAGTCCAAGCCATGAATGATTCATTTCCTGTAGAATATAGCACTGCTCACC
TGATACCTTGTTGTCTTCAGAAACCAGTGACAGACTTGCACTGTCTGTCCCCTTGAAGA
CAGATTGTCATGTGGCTTGTTTTGGTCACTAAAAGTGAGCAAAGTGACAGGCATGAA
```

```
TTCCAGGCAGAGAAAGCTGGTGTACAACCCTCTGGCTGCACCCAACTATGTTAGTTTCC
TGTGTCTGCCATAATGAAATCACCACAACTGGGTGGCTTAAAACAATAGAAACTTATTC
TTTCGTGGTTCTGGAGGCTAAAAGTCCAAAACCAAGGGGCTGACAAGGCCGTGCTCCCT
GTGAAGGATCTGGGGAAGAATCCTTCCTTGCTCTTTCAGATCCTGATGGCTGCTGGCAA
TCCTTGGTGTTCCTTGCCTTGTAGAAGCATTGCTCCAATCTCTGCCCCATCTTCACTT
GATGTTCTCCGTGTGTGTGGGGGGGGTGGGGTGGGGGGAGTCTAGCCTGTGTCTCTGT
ATCCAGCTCTCCCTCCCATTTCTCTTATGAAGACACCAGCCATTGAATTTAGAACCCAC
CCTAATATAGCATGACCTCATCTTAAGTTGATTACGTCTGCAAAAACCCTATTTCCAAA
TAAGGTCACGTCCACAGGTACCAGGGCTTAGGCCTTGAAAATAACTTGCTAGGGGTCAC
AGTATAGGCCACTACACTGGCAATCATGAAGCACATGTTGAAATGGAGCCTTATCAGTC
AGCCTGAGTCCCAATTGACTGCCGTGAGACAGGCCTGTGTCTCCCAGCTCACTTCATT
TCAGTCACGTGGCCCCCAAGTAAAGAGACAGGCTGAATCATCTGCACCAGGTAAAGCTT
CCATCTCTCTTGCTTTTGGTGACTACCTTTAACGGATTCATATACATGACATGAGTCT
GTACTGTATATGATCTTCTCGTAACTGTCTCTGGACTGTCCTTCATGGGACATATTCCT
GTTGCTGGTCACTTACTGAATGCCTGCCATATGCCTATTATCGTGCTGTGTGCCAAGAG
GGATGCATAGAAAATTAGACACAAGGATCCTAATCATGAAAAGTGTACAATCTAATATA
GTGGGCAGGACAGAAAAGACTTATATCAGCATTGGCTGAAATTGTCAGGGGAGACCAAA
TAATAAGGCTTAATAAGAGGTAACCCTAACAGAGCTCCCAGTCTGTTCCAGGCACTGTG
ATAAGCATTTTGCAGGTATTATTAAATTCCATAGGGGTTGTACCCCATGAGGTTGGTAT
TTTATAACCATTTTACAAGACCGGAAACAGAGGCTTCAAAAGGTTGTGTAACTTGCCCA
GTGGTCACACAGGATTCCAATCCTGATCAGCCTGTCTCACAAACATTGGGTTCTATAGA
CGCTCCTAGATTGCATTTTCGTTTAAGCTGAGCCTTGATGGTCTGCTGGAATATGGTAG
GCTACACTTTACACACACAAGGCTCATTTCACCTAATACAGTTATGCCTGGGCAGAAGT
GATCATGTGGCAATATCAACAGGTTACAGTAATAGAAAAGAATCAATAAACTACTGTTT
CATTTCTATGTCATTGTTGCTAAGTTGTCCCAACTACCTTTTTAATGGACTAATCCAA
ACTCTTTTTTTTTCATTTTTCCCTTTATAACAATTGAAGTCAGACTTCATTTTTCAA
ACTTGGCCTCAGATACAAAGATGACATATCAAGAGCCTTCATTTCTCCTAAAGCATT
AAAGCAATTAAAATTTCCAAAAGAACATGAAACTAAACAACCCTATTTTAAGTGTTTC
CAAACTTATTTCTTTTTTTTAAACTTGTTTCAAAACAGCCTTATGAGGACTGTTTTCCA
AACAGCTGTGTAAGAAGCCAGCCACTTTTGAAATCTGATTTTTCCTGTGTAGACATATC
ATATTTTCTATGCTTGAAGAAGCAGGGAATACCCAAGCTGGCATTCAATAGTAGCGAAT
ATGAAATAGACCATTAAAAGAAAGTCATAGGAATGTTAAAATCCATGTTGACTGGTTTT
TACATTTACCCGGCAGCATTCCCGAGCTAGCGTTGGCATGGAGACTGGAAAAGGAAACT
TTCCACAAGTCTGTCACTTGCTACTGTTTCTACTTACTCCACTGTGAGTCCAATTTTAA
CATTTTTTTAAGTTGAAAAAGGGTTTGACTCCTTTTGTGTTTTCTGTTCAAGGCGTTT
TTTAAACATGAGAACACGTGTGAAAAAGGTTTTTAAAAATCAGCCAAAGATTGGGGTTT
CCAAATATTCAGCTGTTTAACATTCAGATAATTGCCTGCCTTCCCCCGCTATCCCCCA
CATTTCGTCTGAATGCTTTGGCACGGGGAGCCCACAGTCTGAAAGTAACTCTGTCCC
AACTCTCCTTACTGCATTTATTAAAGAGGCTGAAAGACGCATCTGCTTTTCAATAGTTT
GCGGTTCTTAAGAGACCAGGAAAGCCAGAGGTTCTGACTATTCAGGAAGAAAGTTGGGT
TTCCCAAAACGGGCAAGCAAGTTCGGTGTGGTCACATCTAGGTATTCTTGACGTCATTT
TTGTTGAGGGAAACAGGCTGCAGTTTTTGGAGCCAGGCTAGGATGAGAGATGGAGGGCA
```

FIGURE 6-9

```
AATCTGTCACTTATTCTTTCCTGGTGTGCCTGGAACCCACTAGACACTCAATTCATGTT
TACGTGAATGAAGGAATCACAATAACGCCCTATCGCATCTGTAAAACCGAAGGGTGATT
TTCCTGGGCTGGAAAGTTTAAGAAAGAAGAGAGAGCTGCGTACCTAGGGCTTAAGGGGC
CTCAGGCTGGCACTCGAAACCAGGCGTTCTCATTTCCCTTTGGCATCACCCTGAACGGC
TGTGCCTGGAGCTGGCGCGGGGCTGAAGAGGGGAGGAAATACATGTGAGGAAATCAGA
GGAGAGGGTCGGGAACAGATGTGGGCATAAAGGGAAGGCCTCTGACTTGAAATAAACAA
ATAGGAGTCCCGCAGCTGGAAGGACAAATCCTTTCACGTCGCGGGTGATGTGGGATTGG
GGCGATTTTGCTCTCCCTTTGTTCTTTCCCCTGCCTTCCACGTTTCCAGGGTATTTGAT
TGATGTCTGTCTTCTCTGTTAAGTTATTCCACCGTGAGGAGAGAGCCGGTGGCAGTACC
TGGCACGCAGCGGGCGCCCAGTATAGACCTGCTGAACAAACGAATGGATTCAGGGGCTG
CTGTGTCCCCCTCACCCACCCCCGCCCCTATGTGTCCACAGCGCCCCGCACGTAGTA
GGCGACCCCTAAACATCTGTACAGCAAATGATTTGCAAGTTTTCGGCGCTGAGCACGTG
GAGCTTTGGAAACCAGGACAGCAAATGAGTGTCTCGGAGACCACAAAAGCGGTTCCGGC
GCGTGCGAAAGGCGGTGGCTGGGCGACGGCGGAGGGAACGGCGCAGAGCGGGGCGCCCC
GCCGGGAGCGCTGCCTGCGTGGCGCCCGAGGCGGGGGCGCGGGGGGCCGCGCATAGCAC
GTGCTCGTCTGGGAGCCGGCCGGGCCGAGGCGGGCGCGCGTGTGCGCGTGGGCGTGGG
GTGTGTGCCCGCGCCGTGCCCCCCGCGTGTGCTGCCGGGCGGGCGCCGGCGTGAGTCAC
GGCGGGGCTAGCCTTTATAACGGCCCGGAGGCTCGCGGGAGCCGCCGCGCCCGTCCGCC
CGCCGCTCCGCGCTCCACCCAGCGCA
```

SEQ ID NO:21
human PK2 promoter region (2.8 kb)

```
TGTACTGTATATGATCTTCTCGTAACTGTCTCTGGACTGTCCTTCATGGGACATATTCC
TGTTGCTGGTCACTTACTGAATGCCTGCCATATGCCTATTATCGTGCTGTGTGCCAAGA
GGGATGCATAGAAAATTAGACACAAGGATCCTAATCATGAAAAGTGTACAATCTAATAT
AGTGGGCAGGACAGAAAAGACTTATATCAGCATTGGCTGAAATTGTCAGGGGAGACCAA
ATAATAAGGCTTAATAAGAGGTAACCCTAACAGAGCTCCCAGTCTGTTCCAGGCACTGT
GATAAGCATTTTGCAGGTATTATTAAATTCCATAGGGGTTGTACCCCATGAGGTTGGTA
TTTTATAACCATTTTACAAGACCGGAAACAGAGGCTTCAAAAGGTTGTGTAACTTGCCC
AGTGGTCACACAGGATTCCAATCCTGATCAGCCTGTCTCACAAACATTGGGTTCTATAG
ACGCTCCTAGATTGCATTTTCGTTTAAGCTGAGCCTTGATGGTCTGCTGGAATATGGTA
GGCTACACTTTACACACACAAGGCTCATTTCACCTAATACAGTTATGCCTGGGCAGAAG
TGATCATGTGGCAATATCAACAGGTTACAGTAATAGAAAAGAATCAATAAACTACTGTT
TCATTTCTATGTCATTGTTGCTAAGTTGTCCCAACTACCTTTTTAATGGACTAATCCA
AACTCTTTTTTTTTTTCATTTTTCCCTTTATAACAATTGAAGTCAGACTTCATTTTTCA
AACTTGGCCTCAGATACAAAGATGACATATCAAGAGCCTTCATTTCTCCTAAAGCAT
TAAAGCAATTAAAATTTCCAAAAGAACATGAAACTAAACAACCCTATTTTAAGTGTTT
CCAAACTTATTTCTTTTTTTTAAACTTGTTTCAAAACAGCCTTATGAGGACTGTTTTCC
AAACAGCTGTGTAAGAAGCCAGCCACTTTTGAAATCTGATTTTTCCTGTGTAGACATAT
```

FIGURE 6-10

```
CATATTTTCTATGCTTGAAGAAGCAGGGAATACCCAAGCTGGCATTCAATAGTAGCGAA
TATGAAATAGACCATTAAAAGAAAGTCATAGGAATGTTAAAATCCATGTTGACTGGTTT
TTACATTTACCCGGCAGCATTCCCGAGCTAGCGTTGGCATGGAGACTGGAAAAGGAAAC
TTTCCACAAGTCTGTCACTTGCTACTGTTTCTACTTACTCCACTGTGAGTCCAATTTTA
ACATTTTTTAAGTTGAAAAAAGGGTTTGACTCCTTTTGTGTTTTCTGTTCAAGGCGTT
TTTTAAACATGAGAACACGTGTGAAAAAGGTTTTTAAAAATCAGCCAAAGATTGGGGTT
TCCAAATATTCAGCTGTTTAACATTCAGATAATTGCCTGCCTTCCCCCGCTATCCCCC
ACATTTCGTCTGAATGCTTTGGCACGGGGGAGCCCCACAGTCTGAAAGTAACTCTGTCC
CAACTCTCCTTACTGCATTTATTAAAGAGGCTGAAAGACGCATCTGCTTTTCAATAGTT
TGCGGTTCTTAAGAGACCAGGAAAGCCAGAGGTTCTGACTATTCAGGAAGAAAGTTGGG
TTTCCCAAAACGGGCAAGCAAGTTCGGTGTGGTCACATCTAGGTATTCTTGACGTCATT
TTTGTTGAGGGAAACAGGCTGCAGTTTTTGGAGCCAGGCTAGGATGAGAGATGGAGGGC
AAATCTGTCACTTATTCTTTCCTGGTGTGCCTGGAACCCACTAGACACTCAATTCATGT
TTACGTGAATGAAGGAATCACAATAACGCCCTATCGCATCTGTAAAACCGAAGGGTGAT
TTTCCTGGGCTGGAAAGTTTAAGAAAGAAGAGAGAGCTGCGTACCTAGGGCTTAAGGGG
CCTCAGGCTGGCACTCGAAACCAGGCGTTCTCATTTCCCTTTGGCATCACCCTGAACGG
CTGTGCCTGGAGCTGGCGCGGGCTGAAGAGGGGAGGAAATACATGTGAGGAAAATCAG
AGGAGAGGGTCGGGAACAGATGTGGGCATAAAGGGAAGGCCTCTGACTTGAAATAAACA
AATAGGAGTCCCGCAGCTGGAAGGACAAATCCTTTCACGTCGCGGGTGATGTGGGATTG
GGGCGATTTTGCTCTCCCTTTGTTCTTTCCCCTGCCTTCCACGTTTCCAGGGTATTTGA
TTGATGTCTGTCTTCTCTGTTAAGTTATTCCACCGTGAGGAGAGAGCCGGTGGCAGTAC
CTGGCACGCAGCGGGCGCCCAGTATAGACCTGCTGAACAAACGAATGGATTCAGGGCT
GCTGTGTCCCCTCACCCACCCCCGCCCCTATGTGTCCACAGCGCCCCGCACGTAGT
AGGCGACCCCTAAACATCTGTACAGCAAATGATTTGCAAGTTTTCGGCGCTGAGCACGT
GGAGCTTTGGAAACCAGGACAGCAAATGAGTGTCTCGGAGACCACAAAAGCGGTTCCGG
CGCGTGCGAAAGGCGGTGGCTGGGCGACGGCGGAGGGAACGGCGCAGAGCGGGGCGCCC
CGCCGGGAGCGCTGCCTGCGTGGCGCCCGAGGCGGGGGCGCGGGGGGCCGCGCATAGCA
CGTGCTCGTCTGGGAGCCGGCCGGGCCGAGGCGGGCGCGCGTGTGCGCGTGGGCGTGG
GGTGTGTGCCCGCGCCGTGCCCCCGCGTGTGCTGCCGGGCGGGCGCCGGCGTGAGTCA
CGGCGGGGCTAGCCTTTATAACGGCCCGGAGGCTCGCGGGAGCCGCCGCCCGTCCGC
CCGCCGCTCCGCGCTCCACCCAGCGCA
```

FIGURE 6-11

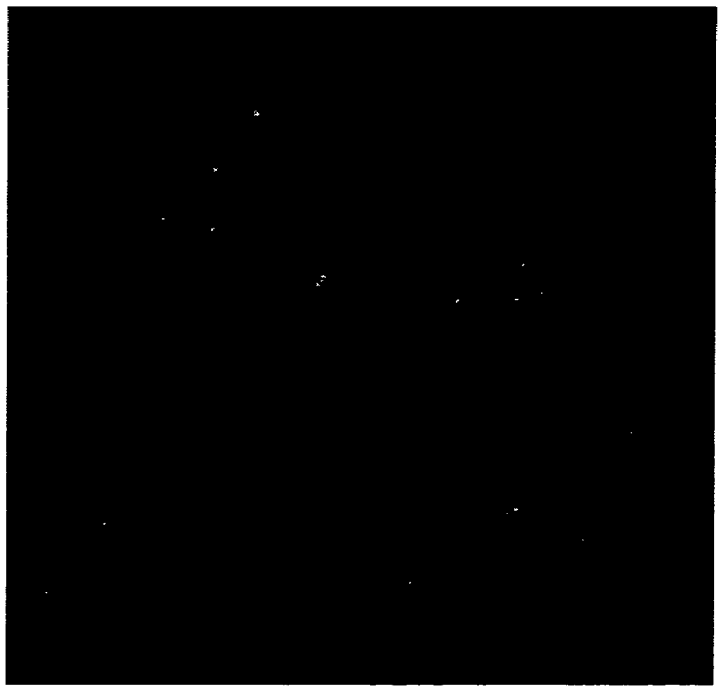
PK2
Saline
FIGURE 7A

SEQUENCE LISTING

<160> NUMBER OF SEQ ID NOS: 21

<210> SEQ ID NO 1
<211> LENGTH: 393
<212> TYPE: PRT
<213> ORGANISM: Homo sapiens

<400> SEQUENCE: 1

```
Met Glu Thr Thr Met Gly Phe Met Asp Asp Asn Ala Thr Asn Thr Ser
 1               5                  10                  15

Thr Ser Phe Leu Ser Val Leu Asn Pro His Gly Ala His Ala Thr Ser
                20                  25                  30

Phe Pro Phe Asn Phe Ser Tyr Ser Asp Tyr Asp Met Pro Leu Asp Glu
            35                  40                  45

Asp Glu Asp Val Thr Asn Ser Arg Thr Phe Phe Ala Ala Lys Ile Val
        50                  55                  60

Ile Gly Met Ala Leu Val Gly Ile Met Leu Val Cys Gly Ile Gly Asn
65                  70                  75                  80

Phe Ile Phe Ile Ala Ala Leu Val Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Thr Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
        195                 200                 205

Val Lys Ser Gln Glu Lys Ile Phe Cys Gly Gln Ile Trp Pro Val Asp
    210                 215                 220

Gln Gln Leu Tyr Tyr Lys Ser Tyr Phe Leu Phe Ile Phe Gly Ile Glu
225                 230                 235                 240

Phe Val Gly Pro Val Val Thr Met Thr Leu Cys Tyr Ala Arg Met Thr
                245                 250                 255

Arg Glu Leu Trp Phe Lys Ala Val Pro Gly Phe Gln Thr Glu Gln Ile
            260                 265                 270

Arg Lys Arg Leu Arg Cys Arg Arg Lys Thr Val Leu Val Leu Met Cys
```

```
                275                 280                 285
Ile Leu Thr Ala Tyr Val Leu Cys Trp Ala Pro Phe Tyr Gly Phe Thr
            290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                325                 330                 335

Ile Asn Thr Leu Cys Phe Val Thr Val Lys Asn Asp Thr Val Lys Tyr
            340                 345                 350

Phe Lys Lys Ile Met Leu Leu His Trp Lys Ala Ser Tyr Asn Gly Gly
        355                 360                 365

Lys Ser Ser Ala Asp Leu Asp Leu Lys Thr Ile Gly Met Pro Ala Thr
370                 375                 380

Glu Glu Val Asp Cys Ile Arg Leu Lys
385                 390

<210> SEQ ID NO 2
<211> LENGTH: 384
<212> TYPE: PRT
<213> ORGANISM: Homo sapiens

<400> SEQUENCE: 2

Met Ala Ala Gln Asn Gly Asn Thr Ser Phe Thr Pro Asn Phe Asn Pro
1               5                   10                  15

Pro Gln Asp His Ala Ser Ser Leu Ser Phe Asn Phe Ser Tyr Gly Asp
            20                  25                  30

Tyr Asp Leu Pro Met Asp Glu Asp Glu Asp Met Thr Lys Thr Arg Thr
        35                  40                  45

Phe Phe Ala Ala Lys Ile Val Ile Gly Ile Ala Leu Ala Gly Ile Met
    50                  55                  60

Leu Val Cys Gly Ile Gly Asn Phe Val Phe Ile Ala Ala Leu Thr Arg
65                  70                  75                  80

Tyr Lys Lys Leu Arg Asn Leu Thr Asn Leu Leu Ile Ala Asn Leu Ala
                85                  90                  95

Ile Ser Asp Phe Leu Val Ala Ile Ile Cys Cys Pro Phe Glu Met Asp
            100                 105                 110

Tyr Tyr Val Val Arg Gln Leu Ser Trp Glu His Gly His Val Leu Cys
        115                 120                 125

Ala Ser Val Asn Tyr Leu Arg Thr Val Ser Leu Tyr Val Ser Thr Asn
130                 135                 140

Ala Leu Leu Ala Ile Ala Ile Asp Arg Tyr Leu Ala Ile Val His Pro
145                 150                 155                 160

Leu Lys Pro Arg Met Asn Tyr Gln Thr Ala Ser Phe Leu Ile Ala Leu
                165                 170                 175

Val Trp Met Val Ser Ile Leu Ile Ala Ile Pro Ser Ala Tyr Phe Ala
            180                 185                 190

Thr Glu Thr Val Leu Phe Ile Val Lys Ser Gln Glu Lys Ile Phe Cys
        195                 200                 205

Gly Gln Ile Trp Pro Val Asp Gln Gln Leu Tyr Tyr Lys Ser Tyr Phe
    210                 215                 220

Leu Phe Ile Phe Gly Val Glu Phe Val Gly Pro Val Val Thr Met Thr
225                 230                 235                 240

Leu Cys Tyr Ala Arg Ile Ser Arg Glu Leu Trp Phe Lys Ala Val Pro
                245                 250                 255
```

-continued

```
Gly Phe Gln Thr Glu Gln Ile Arg Lys Arg Leu Arg Cys Arg Arg Lys
                260                 265                 270

Thr Val Leu Val Leu Met Cys Ile Leu Thr Ala Tyr Val Leu Cys Trp
            275                 280                 285

Ala Pro Phe Tyr Gly Phe Thr Ile Val Arg Asp Phe Pro Thr Val
        290                 295                 300

Phe Val Lys Glu Lys His Tyr Leu Thr Ala Phe Tyr Val Val Glu Cys
305                 310                 315                 320

Ile Ala Met Ser Asn Ser Met Ile Asn Thr Val Cys Phe Val Thr Val
                325                 330                 335

Lys Asn Asn Thr Met Lys Tyr Phe Lys Lys Met Met Leu Leu His Trp
            340                 345                 350

Arg Pro Ser Gln Arg Gly Ser Lys Ser Ser Ala Asp Leu Asp Leu Arg
        355                 360                 365

Thr Asn Gly Val Pro Thr Thr Glu Glu Val Asp Cys Ile Arg Leu Lys
    370                 375                 380
```

<210> SEQ ID NO 3
<211> LENGTH: 393
<212> TYPE: PRT
<213> ORGANISM: Mus musculus

<400> SEQUENCE: 3

```
Met Glu Thr Thr Val Gly Ala Leu Gly Glu Asn Thr Thr Asp Thr Phe
1               5                   10                  15

Thr Asp Phe Phe Ser Ala Leu Asp Gly His Glu Ala Gln Thr Gly Ser
            20                  25                  30

Leu Pro Phe Thr Phe Ser Tyr Gly Asp Tyr Asp Met Pro Leu Asp Glu
        35                  40                  45

Glu Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

Phe Ile Phe Ile Thr Ala Leu Ala Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Arg Gln Leu
        115                 120                 125

Ser Trp Glu His Gly His Val Leu Cys Ala Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Ala Gly Leu Ile Phe Leu Val Trp Ser Val Ser Ile Leu
            180                 185                 190

Ile Ala Ile Pro Ala Ala Tyr Phe Thr Thr Glu Thr Val Leu Val Ile
        195                 200                 205

Val Glu Arg Gln Glu Lys Ile Phe Cys Gly Gln Ile Trp Pro Val Asp
    210                 215                 220

Gln Gln Phe Tyr Tyr Arg Ser Tyr Phe Leu Leu Val Phe Gly Leu Glu
225                 230                 235                 240

Phe Val Gly Pro Val Val Ala Met Thr Leu Cys Tyr Ala Arg Val Ser
                245                 250                 255
```

Arg Glu Leu Trp Phe Lys Ala Val Pro Gly Phe Gln Thr Glu Gln Ile
                260                 265                 270

Arg Arg Thr Val Arg Cys Arg Arg Thr Val Leu Gly Leu Val Cys
            275                 280                 285

Val Leu Ser Ala Tyr Val Leu Cys Trp Ala Pro Phe Tyr Gly Phe Thr
        290                 295                 300

Ile Val Arg Asp Phe Phe Pro Ser Val Phe Val Lys Glu Lys His Tyr
305                 310                 315                 320

Leu Thr Ala Phe Tyr Val Val Glu Cys Ile Ala Met Ser Asn Ser Met
                325                 330                 335

Ile Asn Thr Leu Cys Phe Val Thr Val Arg Asn Asn Thr Ser Lys Tyr
            340                 345                 350

Leu Lys Arg Ile Leu Arg Leu Gln Trp Arg Ala Ser Pro Ser Gly Ser
        355                 360                 365

Lys Ala Ser Ala Asp Leu Asp Leu Arg Thr Thr Gly Ile Pro Ala Thr
370                 375                 380

Glu Glu Val Asp Cys Ile Arg Leu Lys
385                 390

<210> SEQ ID NO 4
<211> LENGTH: 381
<212> TYPE: PRT
<213> ORGANISM: Mus musculus

<400> SEQUENCE: 4

Met Gly Pro Gln Asn Arg Asn Thr Ser Phe Ala Pro Asp Leu Asn Pro
1               5                   10                  15

Pro Gln Asp His Val Ser Leu Asn Tyr Ser Tyr Gly Asp Tyr Asp Leu
            20                  25                  30

Pro Leu Gly Glu Asp Glu Asp Val Thr Lys Thr Gln Thr Phe Phe Ala
        35                  40                  45

Ala Lys Ile Val Ile Gly Val Ala Leu Ala Gly Ile Met Leu Val Cys
50                  55                  60

Gly Ile Gly Asn Phe Val Phe Ile Ala Ala Leu Ala Arg Tyr Lys Lys
65                  70                  75                  80

Leu Arg Asn Leu Thr Asn Leu Leu Ile Ala Asn Leu Ala Ile Ser Asp
                85                  90                  95

Phe Leu Val Ala Ile Val Cys Cys Pro Phe Glu Met Asp Tyr Tyr Val
            100                 105                 110

Val Arg Gln Leu Ser Trp Ala His Gly His Val Leu Cys Ala Ser Val
        115                 120                 125

Asn Tyr Leu Arg Thr Val Ser Leu Tyr Val Ser Thr Asn Ala Leu Leu
130                 135                 140

Ala Ile Ala Ile Asp Arg Tyr Leu Ala Ile Val His Pro Leu Lys Pro
145                 150                 155                 160

Arg Met Asn Tyr Gln Thr Ala Ser Phe Leu Ile Ala Leu Val Trp Met
                165                 170                 175

Val Ser Ile Leu Ile Ala Val Pro Ser Ala Tyr Phe Thr Thr Glu Thr
            180                 185                 190

Ile Leu Val Ile Val Lys Asn Gln Glu Lys Ile Phe Cys Gly Gln Ile
        195                 200                 205

Trp Ser Val Asp Gln Gln Leu Tyr Tyr Lys Ser Tyr Phe Leu Phe Val
210                 215                 220

Phe Gly Leu Glu Phe Val Gly Pro Val Val Thr Met Thr Leu Cys Tyr

```
                     225                 230                 235                 240
Ala Arg Ile Ser Gln Glu Leu Trp Phe Lys Ala Val Pro Gly Phe Gln
                245                 250                 255

Thr Glu Gln Ile Arg Lys Arg Leu Arg Cys Arg Arg Lys Thr Val Leu
            260                 265                 270

Leu Leu Met Gly Ile Leu Thr Ala Tyr Val Leu Cys Trp Ala Pro Phe
        275                 280                 285

Tyr Gly Phe Thr Ile Val Arg Asp Phe Phe Pro Thr Val Val Val Lys
    290                 295                 300

Glu Lys His Tyr Leu Thr Ala Phe Tyr Val Val Glu Cys Ile Ala Met
305                 310                 315                 320

Ser Asn Ser Met Ile Asn Thr Ile Cys Phe Val Thr Val Lys Asn Asn
                325                 330                 335

Thr Met Lys Tyr Phe Lys Lys Met Leu Arg Leu His Trp Arg Pro Ser
            340                 345                 350

His Tyr Gly Ser Lys Ser Ser Ala Asp Leu Asp Leu Lys Thr Ser Gly
        355                 360                 365

Val Pro Ala Thr Glu Glu Val Asp Cys Ile Arg Leu Lys
    370                 375                 380

<210> SEQ ID NO 5
<211> LENGTH: 86
<212> TYPE: PRT
<213> ORGANISM: Homo sapiens

<400> SEQUENCE: 5

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 6
<211> LENGTH: 102
<212> TYPE: PRT
<213> ORGANISM: Homo sapiens

<400> SEQUENCE: 6

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Asn
        35                  40                  45

Asn Phe Gly Asn Gly Arg Gln Glu Arg Arg Lys Arg Lys Arg Ser Lys
    50                  55                  60

Arg Lys Lys Glu Val Pro Phe Phe Gly Arg Arg Met His His Thr Cys
65                  70                  75                  80

Pro Cys Leu Pro Gly Leu Ala Cys Leu Arg Thr Ser Phe Asn Arg Phe
```

```
                           85                  90                  95

Ile Cys Leu Ala Gln Lys
            100

<210> SEQ ID NO 7
<211> LENGTH: 81
<212> TYPE: PRT
<213> ORGANISM: Homo sapiens

<400> SEQUENCE: 7

Ala Val Ile Thr Gly Ala Cys Asp Lys Asp Ser Gln Cys Gly Gly Gly
  1               5                  10                  15

Met Cys Cys Ala Val Ser Ile Trp Val Lys Ser Ile Arg Ile Cys Thr
             20                  25                  30

Pro Met Gly Lys Leu Gly Asp Ser Cys His Pro Leu Thr Arg Lys Val
         35                  40                  45

Pro Phe Phe Gly Arg Arg Met His His Thr Cys Pro Cys Leu Pro Gly
     50                  55                  60

Leu Ala Cys Leu Arg Thr Ser Phe Asn Arg Phe Ile Cys Leu Ala Gln
 65                  70                  75                  80

Lys

<210> SEQ ID NO 8
<211> LENGTH: 86
<212> TYPE: PRT
<213> ORGANISM: Mus musculus

<400> SEQUENCE: 8

Ala Val Ile Thr Gly Ala Cys Glu Arg Asp Ile Gln Cys Gly Ala Gly
  1               5                  10                  15

Thr Cys Cys Ala Ile Ser Leu Trp Leu Arg Gly Leu Arg Leu Cys Thr
             20                  25                  30

Pro Leu Gly Arg Glu Gly Glu Glu Cys His Pro Gly Ser His Lys Ile
         35                  40                  45

Pro Phe Leu Arg Lys Arg Gln His His Thr Cys Pro Cys Ser Pro Ser
     50                  55                  60

Leu Leu Cys Ser Arg Phe Pro Asp Gly Arg Tyr Arg Cys Phe Arg Asp
 65                  70                  75                  80

Leu Lys Asn Ala Asn Phe
             85

<210> SEQ ID NO 9
<211> LENGTH: 81
<212> TYPE: PRT
<213> ORGANISM: Mus musculus

<400> SEQUENCE: 9

Ala Val Ile Thr Gly Ala Cys Asp Lys Asp Ser Gln Cys Gly Gly Gly
  1               5                  10                  15

Met Cys Cys Ala Val Ser Ile Trp Val Lys Ser Ile Arg Ile Cys Thr
             20                  25                  30

Pro Met Gly Gln Val Gly Asp Ser Cys His Pro Leu Thr Arg Lys Val
         35                  40                  45

Pro Phe Trp Gly Arg Arg Met His His Thr Cys Pro Cys Leu Pro Gly
     50                  55                  60

Leu Ala Cys Leu Arg Thr Ser Phe Asn Arg Phe Ile Cys Leu Ala Arg
 65                  70                  75                  80
```

Lys

<210> SEQ ID NO 10
<211> LENGTH: 86
<212> TYPE: PRT
<213> ORGANISM: Rattus sp.

<400> SEQUENCE: 10

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Leu Cys Thr
            20                  25                  30

Pro Leu Gly Arg Glu Gly Glu Glu Cys His Pro Gly Ser His Lys Ile
        35                  40                  45

Pro Phe Phe Arg Lys Arg Gln His His Thr Cys Pro Cys Ser Pro Ser
    50                  55                  60

Leu Leu Cys Ser Arg Phe Pro Asp Gly Arg Tyr Arg Cys Ser Gln Asp
65                  70                  75                  80

Leu Lys Asn Val Asn Phe
                85

<210> SEQ ID NO 11
<211> LENGTH: 81
<212> TYPE: PRT
<213> ORGANISM: Rattus sp.

<400> SEQUENCE: 11

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Gln Val Gly Asp Ser Cys His Pro Leu Thr Arg Lys Val
        35                  40                  45

Pro Phe Trp Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Arg
65                  70                  75                  80

Lys

<210> SEQ ID NO 12
<211> LENGTH: 81
<212> TYPE: PRT
<213> ORGANISM: Dendroaspis polylepis

<400> SEQUENCE: 12

Ala Val Ile Thr Gly Ala Cys Glu Arg Asp Leu Gln Cys Gly Lys Gly
1               5                   10                  15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
        35                  40                  45

Pro Phe Ser Gly Gln Arg Lys Met His His Thr Cys Pro Cys Ala Pro
    50                  55                  60

Asn Leu Ala Cys Val Gln Thr Ser Pro Lys Lys Phe Lys Cys Leu Ser
65                  70                  75                  80

Lys

<210> SEQ ID NO 13
<211> LENGTH: 77
<212> TYPE: PRT
<213> ORGANISM: Bombina variegata

<400> SEQUENCE: 13

```
Ala Val Ile Thr Gly Ala Cys Asp Lys Asp Val Gln Cys Gly Ser Gly
 1               5                   10                  15
Thr Cys Cys Ala Ala Ser Ala Trp Ser Arg Asn Ile Arg Phe Cys Ile
             20                  25                  30
Pro Leu Gly Asn Ser Gly Glu Asp Cys His Pro Ala Ser His Lys Val
         35                  40                  45
Pro Tyr Asp Gly Lys Arg Leu Ser Ser Leu Cys Pro Cys Lys Ser Gly
     50                  55                  60
Leu Thr Cys Ser Lys Ser Gly Glu Lys Phe Lys Cys Ser
 65                  70                  75
```

<210> SEQ ID NO 14
<211> LENGTH: 77
<212> TYPE: PRT
<213> ORGANISM: Bombina maxima

<400> SEQUENCE: 14

```
Ala Val Ile Thr Gly Ala Cys Asp Arg Asp Val Gln Cys Gly Ser Gly
 1               5                   10                  15
Thr Cys Cys Ala Ala Ser Leu Trp Ser Arg Asn Ile Arg Phe Cys Val
             20                  25                  30
Pro Leu Gly Asn Asn Gly Glu Glu Cys His Pro Ala Ser His Lys Val
         35                  40                  45
Pro Tyr Asn Gly Lys Arg Leu Ser Ser Leu Cys Pro Cys Lys Ser Gly
     50                  55                  60
Leu Thr Cys Ser Lys Ser Gly Glu Lys Phe Gln Cys Ser
 65                  70                  75
```

<210> SEQ ID NO 15
<211> LENGTH: 81
<212> TYPE: PRT
<213> ORGANISM: Homo sapiens

<400> SEQUENCE: 15

```
Ala Val Ile Thr Gly Ala Cys Glu Arg Asp Val Gln Cys Gly Ala Gly
 1               5                   10                  15
Thr Cys Cys Ala Ile Ser Leu Trp Leu Arg Gly Leu Arg Met Cys Thr
             20                  25                  30
Pro Leu Gly Arg Glu Gly Glu Glu Cys His Pro Gly Ser His Lys Val
         35                  40                  45
Pro Phe Phe Gly Arg Arg Met His His Thr Cys Pro Cys Leu Pro Gly
     50                  55                  60
Leu Ala Cys Leu Arg Thr Ser Phe Asn Arg Phe Ile Cys Leu Ala Gln
 65                  70                  75                  80
Lys
```

<210> SEQ ID NO 16
<211> LENGTH: 86
<212> TYPE: PRT
<213> ORGANISM: Homo sapiens

<400> SEQUENCE: 16

Ala Val Ile Thr Gly Ala Cys Asp Lys Asp Ser Gln Cys Gly Gly Gly

```
             1               5                  10                 15
       Met Cys Cys Ala Val Ser Ile Trp Val Lys Ser Ile Arg Ile Cys Thr
                        20                  25                  30
       Pro Met Gly Lys Leu Gly Asp Ser Cys His Pro Leu Thr Arg Lys Val
                        35                  40                  45
       Pro Phe Phe Arg Lys Arg Lys His His Thr Cys Pro Cys Leu Pro Asn
                        50                  55                  60
       Leu Leu Cys Ser Arg Phe Pro Asp Gly Arg Tyr Arg Cys Ser Met Asp
       65                   70                  75                  80
       Leu Lys Asn Ile Asn Phe
                        85

<210> SEQ ID NO 17
<211> LENGTH: 1598
<212> TYPE: DNA
<213> ORGANISM: Homo sapiens

<400> SEQUENCE: 17
aataaataaa tagatgaata ctcgcaaaat cgtatgatgt aaatgctatt cttatcccat      60
gttatagata ggaaaactga ggcttggaga gattagcaat attttcaagg tcatgaagcc     120
atcgatctga atcaaagcat ctgcctctgg gggcttagct cccagctccc gtgctagtta     180
accttcctct ctgcactcat aaatgcctat cagcgtttca atgtggaaac cctagacccc     240
tgtgacattt gataagaaag gttttgtgga tgaatctgct tgtgaaatac tacaaactgc     300
atttcccact tggtgtttca aacacttatt agcatatgaa aggccctgaa agttctgca     360
aaaaacaagc cggtttgtgt ttcccaaatt tttgactgta gaagtctttt atttgtttat     420
ttgtgtatta acatattgca acacataccct tgggaaatgt tggcttttat tactgtggag     480
agaaggcaga tcatctgaca aagcactggg agctctctct gggtcgtatg acacagagag     540
ggctggggtc aggggcttcc ctcacaggcg aggggccat cccgaaagtc aacttcccac      600
cagactggca tctgagacca ccgtgtttat acactcacgg ataaggccac tctcatgctc     660
accccctaaaa ctggaaggcc agtggtgtgg ctctggtacc tttcagccac agcccatacc    720
agctcggctc tgcagggtac tgagagagtg tgtgccctgt atgtttgctg gctttctgcc     780
cttgggtcat tgtaccaagg gacacttgct ggtgttcatc ctgagcccat gagagagcaa     840
atccttatgt gtgtgtcact taggaacatc agccccacaa gtctggtctt ttttttcctca    900
ctgtcttatg gctcctcact ataattttaa ccttttagag aaataaggat accacctcac     960
cctcttctgt cttctcagct acctctgtgt tgagcccatg gtaaatgcct agataagtct    1020
tggtgtgagt gagagggaac caataatctt gtatgttgca tagtttggtg cagggaagca    1080
taaatggtga tgttgcaaat cccttaattc attaccagag gctttcctct gccccaagta    1140
ggatagaagg ataccagag gcagaaaaga acattgagtg aaatatacat aactgtctga     1200
atcactgcgt tcttgggaga gttagagcaa ccgtcaaagc cccccaagta tccatttta    1260
ttggttttga tgttgatttg atgttgttag agattcaggt ctcatcttcg cttctgagat    1320
catctgagta acatcggtgt tggagaaggg aagagcagag atgaggcatc acaggcagc    1380
cctggatcct gagtgtaaac atctgggagg aggcggggga tgcaggagag cctggcctcc    1440
ccagcttgcc aggcacaagg ctgagcggga ggaagcgaga ggcatctaag caggcagtgt    1500
tttgccttca ccccaagtga ccatgagagg tgccacgcga gtctcaatca tgctcctcct    1560
agtaactgtg tctgactgtg ctgtgatcac agggtaa                             1598
```

-continued

<210> SEQ ID NO 18
<211> LENGTH: 7349
<212> TYPE: DNA
<213> ORGANISM: Mus musculus

<400> SEQUENCE: 18

| | | | | | |
|---|---|---|---|---|---|
| acacaagaaa | gaagagggaa | gagtgttcta | gaccatcctg | aaagtagata | gccatagatc | 60 |
| agtggcccag | gctctgcact | actgttctct | ggcaagtcac | atgtggaggc | tcagaaacat | 120 |
| ctgagatttg | tggaaacaag | tttaaagatt | gagtatatgg | aatactccca | ccaaattgct | 180 |
| gtgtcttact | tctagttatt | ggccacccaa | ggttttatg | gcaatgttat | aaatttgaag | 240 |
| agaaactcta | acagttaaaa | gcttggcacc | agagcacact | gggtttaaat | ctagtttctt | 300 |
| tccttagcaa | ttaccctggc | ttgagatggc | atggttgacc | tttctaaatt | ccactttgct | 360 |
| cttccataat | ggccaagagt | tctacccaga | gggtccctgg | ggttttttata | gaagatgtac | 420 |
| tggaattcac | aaagtactta | ctgtgtgcaa | cgcatagctc | tgcacttttg | aaatgaaaac | 480 |
| accacaattg | gcttgtgccc | caaaacaaag | aaacaaaaca | aataaagct | aggagtcata | 540 |
| atgtgaaccc | tagttcccta | gcaagcctcc | tgcctcagct | tcctgaatgc | tgggatttca | 600 |
| agctaagagc | caccacatct | ggttataaaa | gttttgtacc | tattatttca | tatgtatatg | 660 |
| aatatgtctt | gttacttctt | ctaggtcctt | tccttcttta | aatgttgctg | aatgaggttt | 720 |
| atttcgctgt | gatagatagt | tcctgttgac | ctgaaaggat | gataaagtaa | ctacctagtc | 780 |
| atggttttta | atcttaagaa | aaccccttttc | ttaggtgaga | cttctttttt | ttccatctgg | 840 |
| aaagttacca | aatacgccac | acatttgcat | aacaatctct | ttgaatgaag | acagcagcgc | 900 |
| acgcagcacc | agcttttgcc | tttagggcca | tcttcaatag | aaaaaaaata | aaaaaaataa | 960 |
| aaagctgac | agagaagagc | agcgaacgtt | ataatgagaa | catctgaatc | tttttagaacc | 1020 |
| aaatgttctt | cggtgaccct | tcatattatc | tcaaagtcac | ggtgtgctaa | ttgcttgaag | 1080 |
| aaaaccctttt | ctccgggatt | aatacttcag | ctatttaaaa | atagataaac | tttactgtac | 1140 |
| attatcactt | gaatgaaaca | aatgcttttc | agtgcctccg | tagacaattg | gcgttcacat | 1200 |
| tgaatcctgg | tgatttatta | tttttttta | aataaagaga | aaatcatcag | cattgaacta | 1260 |
| gattaaaata | gacatcttat | ttagaattat | aaaagccatt | cctttttcat | gtcacattta | 1320 |
| aaatacggtt | attattttag | aatgatagca | cagatgatat | tataggttta | acaagaagag | 1380 |
| ccacgtggaa | cagtgcctca | ataaaggatg | aaggcaaagt | agaaaggaga | atatccatct | 1440 |
| tatttcattt | gactttttttt | ttggaacaaa | tctaaatgaa | aagtcattta | cacaaaggca | 1500 |
| aataaaaccc | agtaatgaaa | ttaccgggcc | cacctattgt | gttaccataa | taagccataa | 1560 |
| gaaaaagacg | catgcaaagt | aaggtttcag | caaagccaga | gtcactctta | acaacagagc | 1620 |
| catgtgagga | agcgtctgga | acagtttcct | cttctgtggc | tgagaaaatg | cctgacactt | 1680 |
| tccgtgcaag | atggagagca | aggcctgtgt | ttcttgatct | ttctttgata | acctcatcac | 1740 |
| tcttgatgaa | gcatctactg | tgtgctggat | cattggaatc | agttatagta | aggttaatat | 1800 |
| gcaaatagc | aatcagtaag | ccagaacttt | ggcaatatc | cgaaagtcca | aagaatgtg | 1860 |
| gattacatca | gtgagttgga | gtctgcgcag | tacatctcac | aggaagttca | agcaaagaca | 1920 |
| gtggaggcaa | gatcagtaag | agtttgtaaa | actgcagtat | gagacagtac | agagactcta | 1980 |
| ggctcttttt | ttttttttaa | acacatgaat | ctagaaacaa | cagagctgga | aaatagccca | 2040 |
| gtcataagca | caacaaacta | atttgctcac | taggacccaa | tgtgaagcaa | gccagactga | 2100 |
| tgggtggtat | acacacatca | tccactgtgt | ttgttcacaa | gaacccgtgc | aaaataagct | 2160 |

```
ggaccagcga tggtatagta tacacatatc atctcaggca gagacaggca gatctctggg    2220
gctcgctggc cagccaacct agcttacccg gtgagtccca ggcctagtga aagaccctat    2280
ctcagaaaag aaggtagaag gctcttgaag aatgtcagct ggggctgtcc cctggcctcc    2340
acatgcaaag acgcagtgtg tgcccacgaa tgcgcacaca cacacacaca caacgaggaa    2400
tcagcaagct ttctctacac tagcagatag aagatatttt ttggcttttc caatcatgtg    2460
gtctcacaag tactcagtaa aaagcagaca cgggcaatac agaaacaggc atggctagat    2520
agaacataaa aaataaataa tagatagata gatagataga tagatagata gatagataga    2580
tagatagata gaatactggc tagttttgtg tcaacttgac acagctggag ttatcacaga    2640
gaggggagct tcagttgggg aaatgcctcc atgagataca actgtaaggc attttctcaa    2700
ttagtgatca agagggaaag gccccttgtg ggtgggacca tctctgggct ggtagtcttg    2760
ggttctataa gagagcaggc tgagcaagcc aggggaagga agacagtaag taacatccct    2820
ccatggcctc tgcattagct tctgcttcct gacctgcttg agttccagtc ctgacttcct    2880
ttggtgatga agagcagtat ggaagtgtaa gccgaataaa cccttcctc cccaacttgc    2940 ttcttggtca tcatgtttgt acaagaatag aaaccctgac taagacagat agatagacaa    3000
caaaaagcaa tgtgtcaacg ttttcccagt ttctactaaa tcctagtcat tgtggctaca    3060
ttctatgaaa tgaaaaaatt ttaaagtcca acaagaagcc actggttggc catttctttc    3120
tttagctcag ctgctccccc tcgccctgcc tgcctttgtc caatcccatg taagcaccag    3180
agtccctcct gcgagccagt taccacagtg aggttcctcc ttcctcccca ctcccaatag    3240
ttcctgccct tctttctctt gactgcccac aaggattctg cagtgctctg ccttcaggag    3300
atggatggtg acttctctca gtcctccatc atgctcttct ccacattcct agtgatttgg    3360
tcagccaaaa tcgagtgctt tgttcaattc ttggtacata gcttgtgctt agtaagtacc    3420
tgctgaatga gtgaatgaat gatggtctat tagttaaaac aaagcactct cagcttgcac    3480
atttgtactc tttcaccatg tatcacttga aggactaaac aaacaaatac agacacacat    3540
tatcctttgg agtaagaatt actaaggttg gccaaagtac agtggctcct ttcctgtagc    3600
actgcttacc agatttctgg tcttagcagc aactacattt gcactgctgt ctttagcaag    3660
gtgaactgtc acgtgacccg tttccgtcac tgtggcacag tcaggcttga gttccaggca    3720
gaggcagcag aaagctgaat tgcaaccctc cagccccacc cttccttta gtttcccaga    3780 ggttctagga gaagtgagca gaactaggtg gcatcgcaca tcagaggtta ttttcttgta    3840
gctctggatg ttagaagtcc aaaatcaagg atgctttccc cagctcttct gaattctgaa    3900
agccagctgt gggggaggag gtgtgtcata tcagtctcta tatccaaaga tcttgcatct    3960
gttataaaaa gatgggaaaa tagcttagtc agcaaagggc ttgcctcgaa acattgatg    4020 tcctgagttc agtctccaga actcaaaaaa gccaggtgcg gtgacttgag tctgtggcta    4080
cctgagtctg taatcccaac aatggtaaaa tgggaggccg aggcaggcag atttcctgag    4140
gctcacagga cagtgaggct gacctacatg tcaaagttcc agtctagtga gagaccctgt    4200
cccaaacaaa aggtagaagc cgtctggtac tcaaggttgt ctgacctgca catatgctgt    4260
gtgtagaggt gcccacacat acacaaatgc atactcatgc atgcacagac acacacacac    4320
acaaaaccac acttttaaa aaaaatgaca aagatatcag ttgttgggtt tagggcatac    4380
tctcatccag tatgacttca agtttggttg atcatatcag caaggaccct acttccaaat    4440
aaagacacag gaaccaggag ctagagtttc aacataactt tctaggtgag acttagtata    4500
```

```
acctagtct ggaatcatca taaatcatca gttcaaataa agtccccctc agctgagctc    4560
ccagagtgcc tgctgtagct tgaatgtgtg acagctgtaa gacatgtctc caggggcccc    4620
tcattccagt cccatattct tggaggaaac agcaggcgaa tcccctgcac caggtctctc    4680
tttccctcta agcttttgct gcctgcattc gtgatccatg tagattaagt aagtgcatct    4740
acactgtgtg attcttgctt ctaacctctc tctgtccctg atcacaaaat ccactcctgg    4800
tgctcatcaa tcattgtctg agtgctggct aatgccacat gcaagaagga ttttcaggag    4860
aaatggactc ctagccagca cgtgtatgcg atctaattag gtgggcagga cagaaaacag    4920
ccgtatcagt gttcaatgaa cctatcaggg aaaagcacat gataagattt aactagagtg    4980
cacccccttg caggacttcc aggctatcac agacttggtg cttagcactt tcaaaggtgt    5040
tctctttgag cttcatggtg gctggaccag gaagttggta ttttatgccc acagggagcc    5100
agagacctta agaggtcaaa ggttcagttg ccacaaaaga ctccaatcca ggtcactcta    5160
actttcaaat gtagggttct tcgtatcaca ctgtcaaacc agctgagagg tggtagtcat    5220
gcaagactgc cagctatata tactctgaac ccacgaagtt ttggtcctca cccaaaggtt    5280
gttcctggct aatttgacca caatgactga tcgaaccaac aggttgcagt aacaaaacag    5340
aacttgaatt tcattattgt tttatcgttg tcttacggtg gggaggagtg taattcaaac    5400
agtgtctttc catttctaat aaatgaaatc agacttgatc taacttacct gtggggtcca    5460
aagaagttct gttgaagagt tttcatttct tctatcaagt attaaagcca ttaaacccttt    5520 ccaaagaggt ttaggggggta gccgagcagt agaattgacc caggatgtcc atgcccttgg    5580
ttgcaacctc agcacaggaa aacagaagag ccttaaacca gtcttatgtt taagcatctc    5640
taaccttgat tcaaaagtct taggagactg ttttgggaac agtcaatctc aatggaaggt    5700
tagcatttcc ctgggtagag atggcctgtt ttctacgctc tgagaagtag ggaatacccca    5760 gttggcattt gatagtaaca aatatgaaac cgaccattta agaaaagaat taaaagagtg    5820
tcaggaatgt taaagttcat gttgactggt ttttacattt cccccgggct gcactcccat    5880
gccttcgttg gcatggagac tggaaaggaa actttccacc agtctgtcac ttgctactgt    5940
ttccacttag tttactgtga atccactttt aacagttttc tcaaagttaa aaaggagttt    6000
gatcccgggt gtgttttcgg tctcaggatg cttcttgaac tcaaaaacat ggtacaaaaa    6060
ggctttaaaa ctcagccaaa gatctagggt ttgaaacgcc cagctgttta acattcaaat    6120
aattccctgg ccctttgttc atttttttc ccctctacat ttcgtctgaa tgctttggca    6180
tgagggagcc cacagactga aagtaactgt ggcccagctc tccttactgt attgattaaa    6240
gtggctgaaa aggcccatct gcctttcagc agtctgtggt cctatgggac atgggaaagt    6300
ctaaggtccc tagctgtcta ggagtgaggt gggctccccc aaacctcaga aaagtcaaa    6360 ttgatcatcc ttgtagaagc aagcaagatg agattattgg agccaaatta ggaacacaga    6420
gagggttgtc tcttgtctca tgggatgaat gcctagagtc cagcagacac acctaagtga    6480
ttgatcagaa ccccccaccac caccaccaaa aaaaaatata tatatatgta taagacttgg    6540
agtttcctag gctggagaac cgagctggga gagagccacc ttcccagggc ctcaggctgg    6600
cagagcaagc tgggagttct ccttttttcc cccttttggca acatcctgtt ctgcctgaag    6660
caggctggaa gctgcagagg ggagggaacg cacgtgagag aaatcagggc agaaagggtc    6720
aggaacagat gtgggcaccg gagaagtcat ttccaaaaag gaaggagac tcccacagct    6780 ggaggggcag ccgagtccct ccaacttctt aagagatgtg ggacgggtg tgctggcgct    6840 ttgttcttcc agcctgctat gttcgcttgc ccttgcttg tttgtctgtt ctttctatgt    6900
```

-continued

```
tgtgccacct cagggcagag ccggtggcag tacctggcac gcacggatct ctcactgtag    6960
atatgctgaa caaatgtgta caaatacagt gcagttgtgt ccgccgcgtc tggcacgtcg    7020
tgggtacccc ctgcacatct gtatggcaaa tgatgtgcct ctgcgagtgt gggggctgag    7080
cacgtgaggc tctggaaaac aggacggcga aggaggaggg tttctgagac cacaaaagct    7140
tcaggaaggc tggctagggc tgcggcgccc cgcggggggct ctgcccgcgt ggcgctttgc    7200
gcgtggggcg cggggcacgt gcgcgtgtgc gcgtggagcg cggggtgtgt gcccgcgccg    7260 tgcccccgc gtgctgcctg gcgtgagtca ccgcggggct cgcctttata accgccgcca    7320
ggctcgcagc tccgcagagc agcccggcc                                     7349
```

```
<210> SEQ ID NO 19
<211> LENGTH: 2800
<212> TYPE: DNA
<213> ORGANISM: Mus musculus

<400> SEQUENCE: 19
```

```
cagctgagct cccagagtgc ctgctgtagc ttgaatgtgt gacagctgta agacatgtct      60
ccaggggccc ctcattccag tcccatattc ttggaggaaa cagcaggcga atccctgca     120 ccaggtctct ctttcctct aagcttttgc tgcctgcatt cgtgatccat gtagattaag     180
taagtgcatc tacactgtgt gattcttgct tctaacctct ctctgtccct gatcacaaaa    240
tccactcctg gtgctcatca atcattgtct gagtgctggc taatgccaca tgcaagaagg    300
attttcagga gaaatggact cctagccagc acgtgtatgc gatctaatta ggtgggcagg    360
acagaaaaca gccgtatcag tgttcaatga acctatcagg gaaaagcaca tgataagatt    420
taactagagt gcaccccctt gcaggacttc caggctatca cagacttggt gcttagcact    480
ttcaaaggtg ttctctttga gcttcatggt ggctggacca ggaagttggt atttatgcc    540 cacagggagc cagagacctt aagaggtcaa aggttcagtt gccacaaaag actccaatcc    600
aggtcactct aactttcaaa tgtagggttc ttcgtatcac actgtcaaac cagctgagag    660
gtggtagtca tgcaagactg ccagctatat atactctgaa cccacgaagt tttggtcctc    720
acccaaaggt tgttcctggc taatttgacc acaatgactg atcgaaccaa caggttgcag    780
taacaaaaca gaacttgaat tcattattg ttttatcgtt gtcttacggt ggggaggagt    840
gtaattcaaa cagtgtcttt ccatttctaa taaatgaaat cagacttgat ctaacttacc    900
tgtggggtcc aaagaagttc tgttgaagag ttttcatttc ttctatcaag tattaaagcc    960
attaaaccct tccaaagagg tttagggggt agccgagcag tagaattgac ccaggatgtc   1020
catgcccttg gttgcaacct cagcacagga aaacagaaga gccttaaacc agtcttatgt   1080
ttaagcatct ctaaccttga ttcaaaagtc ttaggagact gttttgggaa cagtcaatct   1140
caatggaagg ttagcatttc cctgggtaga gatggcctgt tttctacgct ctgagaagta   1200
gggaataccc agttggcatt tgatagtaac aaatatgaaa ccgaccattt aagaaaagaa   1260
ttaaaagagt gtcaggaatg ttaaagttca tgttgactgg ttttttacatt tcccccgggc   1320 tgcactccca tgccttcgtt ggcatggaga ctggaaagga aactttccac cagtctgtca   1380
cttgctactg tttccactta gtttactgtg aatccacttt taacagtttt ctcaaagtta   1440
aaaaggagtt tgatcccggg tgtgtttttcg gtctcaggat gcttcttgaa ctcaaaaaca   1500
tggtacaaaa aggctttaaa actcagccaa agatctaggg tttgaaacgc ccagctgttt   1560
aacattcaaa taattccctg gccctttgtt cattttttt cccctctaca tttcgtctga   1620
```

```
atgctttggc atgagggagc ccacagactg aaagtaactg tggcccagct ctccttactg    1680
tattgattaa agtggctgaa aaggcccatc tgcctttcag cagtctgtgg tcctatggga    1740
catgggaaag tctaaggtcc ctagctgtct aggagtgagg tgggctcccc caaacctcag    1800
aaaaagtcaa attgatcatc cttgtagaag caagcaagat gagattattg gagccaaatt    1860
aggaacacag agaggttgt ctcttgtctc atgggatgaa tgcctagagt ccagcagaca     1920
cacctaagtg attgatcaga accccccacca ccaccaccaa aaaaaaatat atatatatgt   1980
ataagacttg gagtttccta ggctggagaa ccgagctggg agagagccac cttcccaggg    2040
cctcaggctg gcagagcaag ctgggagttc tcctttttc ccctttggc aacatcctgt      2100 tctgcctgaa gcaggctgga agctgcagag gggagggaac gcacgtgaga gaaatcaggg    2160
cagaaagggt caggaacaga tgtgggcacc ggagaagtca tttccaaaaa ggaaaggaga    2220
ctcccacagc tggaggggca gccgagtccc tccaacttct taagagatgt gggacggggt    2280
gtgctggcgc tttgttcttc cagcctgcta tgttcgcttg ccctttgctt gtttgtctgt    2340
tctttctatg ttgtgccacc tcagggcaga gccggtggca gtacctggca cgcacggatc    2400
tctcactgta gatatgctga acaaatgtgt acaaatacag tgcagttgtg tccgccgcgt    2460
ctggcacgtc gtgggtaccc cctgcacatc tgtatggcaa atgatgtgcc tctgcgagtg    2520
tgggggctga gcacgtgagg ctctggaaaa caggacggcg aaggaggagg gtttctgaga    2580
ccacaaaagc ttcaggaagg ctggctaggg ctgcggcgcc ccgcgggggc tctgcccgcg    2640
tggcgctttg cgcgtgggcg cggggcacgt gcgcgtgtg cgcgtggagc gcggggtgtg     2700
tgcccgcgcc gtgccccccg cgtgctgcct ggcgtgagtc accgcggggc tcgcctttat    2760
aaccgccgcc aggctcgcag ctccgcagag cagcccggcc                          2800
```

<210> SEQ ID NO 20
<211> LENGTH: 4038
<212> TYPE: DNA
<213> ORGANISM: Homo sapiens

<400> SEQUENCE: 20

```
tcccatgaga tggtaagctc ccagggggct gggttcatgt ctgttttgct caccctcgta     60
cccccaatgc tgcacacaat atctggaata tagtaagtct tagttaatac ctgttgaatg    120
aataaattat ggttttctac ccacctaaaa gaaaatatta gcttacacat ttactcactt    180
tcagagtctt tgtataattc tggtataaag aatgctgtac tagaaaaaat acaaaggaaa    240
ttacacatta ttatttataa tagcaattac taatataatt caaagttcat tatgctcatt    300
aaggagtcca agccatgaat gattcatttc ctgtagaata tagcactgct cacctgatac    360
cttgttgtct tcagaaacca gtgacagact tgcactgtct gtccccttga agacagattg    420
tcatgtggct tgttttggtc actaaaaagt gagcaaaagt gacaggcatg aattccaggc    480
agagaaagct ggtgtacaac cctctggctg cacccaacta tgttagtttc ctgtgtctgc    540
cataatgaaa tcaccacaac tgggtggctt aaaacaatag aaacttattc tttcgtggtt    600
ctggaggcta aaagtccaaa accaaggggc tgacaaggcc gtgctccctg tgaaggatct    660
ggggaagaat ccttccttgc tctttcagat cctgatggct gctggcaatc cttggtgttc    720
cttgccttgt agaagcattg ctccaatctc tgccccatc ttcacttgat gttctcccgt     780
gtgtgtgggg gggtgggt ggggggagtc tagcctgtgt ctctgtatcc agctctccct      840
cccatttctc ttatgaagac accagccatt gaatttagaa cccacccctaa tatagcatga   900 cctcatctta agttgattac gtctgcaaaa accctatttc caaataaggt cacgtccaca    960
```

-continued

```
ggtaccaggg cttaggcctt gaaaataact tgctagggt cacagtatag gccactacac    1020
tggcaatcat gaagcacatg ttgaaatgga gccttatcag tcagcctgag tcccaaattg    1080
actgccgtga dacaggcctg tgtctcccag ctcacttcat ttcagtcacg tggccccaa     1140 gtaaagagac aggctgaatc atctgcacca ggtaaagctt ccatctctct tgctttttgg    1200
tgactacctt taacggattc atatacatga catgagtctg tactgtatat gatcttctcg    1260
taactgtctc tggactgtcc ttcatgggac atattcctgt tgctggtcac ttactgaatg    1320
cctgccatat gcctattatc gtgctgtgtg ccaagaggga tgcatagaaa attagacaca    1380
aggatcctaa tcatgaaaag tgtacaatct aatatagtgg gcaggacaga aaagactat     1440 atcagcattg gctgaaattg tcaggggaga ccaaataata aggcttaata agaggtaacc    1500
ctaacagagc tcccagtctg ttccaggcac tgtgataagc attttgcagg tattattaaa    1560
ttccataggg gttgtacccc atgaggttgg tattttataa ccattttaca agaccggaaa    1620
cagaggcttc aaaaggttgt gtaacttgcc cagtggtcac acaggattcc aatcctgatc    1680
agcctgtctc acaaacattg ggttctatag acgctcctag attgcatttt cgtttaagct    1740
gagccttgat ggtctgctgg aatatggtag gctacactt acacacacaa ggctcatttc     1800
acctaataca gttatgcctg ggcagaagtg atcatgtggc aatatcaaca ggttacagta    1860
atagaaaaga atcaataaac tactgttca tttctatgtc attgttgcta agttgtccca     1920
actacctttt ttaatggact aatccaaact ctttttttt ttcattttc cctttataac      1980 aattgaagtc agacttcatt tttcaaactt ggcctcagat acaaagatga catatcaaga    2040
gccttcattt ctctcctaaa gcattaaagc aattaaaatt tccaaaagaa catgaaacta    2100 aacaaccctta tttttaagtg tttccaaact tatttctttt ttttaaactt gtttcaaaac    2160
agccttatga ggactgtttt ccaaacagct gtgtaagaag ccagccactt ttgaaatctg    2220
atttttcctg tgtagacata tcatatttc tatgcttgaa gaagcaggga atacccaagc     2280
tggcattcaa tagtagcgaa tatgaaatag accattaaaa gaaagtcata ggaatgttaa    2340
aatccatgtt gactggtttt tacatttacc cggcagcatt cccgagctag cgttggcatg    2400
gagactggaa aaggaaactt tccacaagtc tgtcacttgc tactgttct acttactcca     2460 ctgtgagtcc aattttaaca ttttttttaag ttgaaaaaag ggtttgactc cttttgtgtt    2520
ttctgttcaa ggcgtttttt aaacatgaga acacgtgtga aaaaggtttt taaaaatcag    2580
ccaaagattg gggtttccaa atattcagct gtttaacatt cagataattg cctgccttcc    2640
ccccgctatc ccccacattt cgtctgaatg ctttggcacg ggggagcccc acagtctgaa    2700
agtaactctg tcccaactct ccttactgca tttattaaag aggctgaaag acgcatctgc    2760
ttttcaatag tttgcggttc ttaagagacc aggaaagcca gaggttctga ctattcagga    2820
agaaagttgg gtttcccaaa acgggcaagc aagttcggtg tggtcacatc taggtattct    2880
tgacgtcatt tttgttgagg gaaacaggct gcagttttg gagccaggct aggatgagag     2940
atggagggca aatctgtcac ttattctttc ctggtgtgcc tggaacccac tagacactca    3000
attcatgttt acgtgaatga aggaatcaca ataacgccct atcgcatctg taaaaccgaa    3060
gggtgatttt cctgggctgg aaagtttaag aagaagaga gagctgcgta cctagggctt     3120
aaggggcctc aggctggcac tcgaaaccag gcgttctcat ttcccttgg catcaccctg     3180 aacggctgtg cctggagctg gcgcggggct gaagagggga ggaaatacat gtgaggaaaa    3240
tcagaggaga gggtcgggaa cagatgtggg cataaaggga aggcctctga cttgaaataa    3300
```

```
acaaatagga gtcccgcagc tggaaggaca atcctttca cgtcgcgggt gatgtgggat     3360
tggggcgatt ttgctctccc tttgttcttt ccctgcctt ccacgtttcc agggtatttg     3420
attgatgtct gtcttctctg ttaagttatt ccaccgtgag gagagagccg gtggcagtac     3480
ctggcacgca gcgggcgccc agtatagacc tgctgaacaa acgaatggat tcaggggctg     3540
ctgtgtcccc ctcacccacc cccgccccc tatgtgtcca cagcgccccg cacgtagtag      3600 gcgacccta aacatctgta cagcaaatga tttgcaagtt ttcggcgctg agcacgtgga      3660 gcttggaaa ccaggacagc aaatgagtgt ctcggagacc acaaaagcgg ttccggcgcg      3720
tgcgaaaggc ggtggctggg cgacggcgga gggaacggcg cagagcgggg cgccccgccg     3780
ggagcgctgc ctgcgtggcg cccgaggcgg gggcgcgggg ggccgcgcat agcacgtgct     3840
cgtctgggag ccggccgggc cgaggcgggc gcgcgtgtgc gcgtggggcg tggggtgtgt     3900
gcccgcgccg tgcccccgc gtgtgctgcc gggcgggcgc cggcgtgagt cacggcgggg     3960
ctagccttta taacggcccg gaggctcgcg ggagccgccg cgcccgtccg cccgccgctc     4020
cgcgctccac ccagcgca                                                  4038

<210> SEQ ID NO 21
<211> LENGTH: 2800
<212> TYPE: DNA
<213> ORGANISM: Homo sapiens

<400> SEQUENCE: 21
tgtactgtat atgatcttct cgtaactgtc tctggactgt ccttcatggg acatattcct      60
gttgctggtc acttactgaa tgcctgccat atgcctatta tcgtgctgtg tgccaagagg     120 gatgcatga aaattagaca caaggatcct aatcatgaaa agtgtacaat ctaatatagt      180
gggcaggaca gaaaagactt atatcagcat tggctgaaat tgtcagggga gaccaaataa     240
taaggcttaa taagaggtaa ccctaacaga gctcccagtc tgttccaggc actgtgataa     300
gcattttgca ggtattatta aattccatag gggttgtacc ccatgaggtt ggtatttat      360 aaccatttta caagaccgga acagaggct tcaaaaggtt gtgtaacttg cccagtggtc      420
acacaggatt ccaatcctga tcagcctgtc tcacaaacat tgggttctat agacgctcct     480
agattgcatt ttcgtttaag ctgagccttg atggtctgct ggaatatggt aggctacact     540
ttacacacac aaggctcatt tcacctaata cagttatgcc tgggcagaag tgatcatgtg     600
gcaatatcaa caggttacag taatagaaaa gaatcaataa actactgttt catttctatg     660
tcattgttgc taagttgtcc caactacctt ttttaatgga ctaatccaaa ctcttttttt     720
ttttcatttt tccctttata acaattgaag tcagacttca ttttcaaac ttggcctcag     780 atacaaagat gacatatcaa gagccttcat ttctctccta aagcattaaa gcaattaaaa     840
tttccaaaag aacatgaaac taaacaaccc tattttttaag tgtttccaaa cttatttctt     900
ttttttaaac ttgtttcaaa acagccttat gaggactgtt ttccaaacag ctgtgtaaga     960
agccagccac ttttgaaatc tgatttttcc tgtgtagaca tatcatattt tctatgcttg    1020
aagaagcagg gaatacccaa gctggcattc aatagtagcg aatatgaaat agaccattaa    1080
aagaaagtca taggaatgtt aaaatccatg ttgactggtt tttacattta cccggcagca    1140
ttcccgagct agcgttggca tggagactgg aaaggaaac tttccacaag tctgtcactt    1200
gctactgttt ctacttactc cactgtgagt ccaattttaa cattttttta agttgaaaaa    1260
agggtttgac tcctttgtg ttttctgttc aaggcgtttt ttaaacatga gaacacgtgt    1320
gaaaaaggtt tttaaaaatc agccaaagat tgggggtttcc aaatattcag ctgtttaaca    1380
```

```
ttcagataat tgcctgcctt ccccccgcta tcccccacat ttcgtctgaa tgctttggca    1440
cgggggagcc ccacagtctg aaagtaactc tgtcccaact ctccttactg catttattaa    1500
agaggctgaa agacgcatct gcttttcaat agtttgcggt tcttaagaga ccaggaaagc    1560
cagaggttct gactattcag gaagaaagtt gggtttccca aaacgggcaa gcaagttcgg    1620
tgtggtcaca tctaggtatt cttgacgtca tttttgttga gggaaacagg ctgcagtttt    1680
tggagccagg ctaggatgag agatggaggg caaatctgtc acttattctt tcctggtgtg    1740
cctggaaccc actagacact caattcatgt ttacgtgaat gaaggaatca caataacgcc    1800
ctatcgcatc tgtaaaaccg aagggtgatt ttcctgggct ggaaagttta agaaagaaga    1860
gagagctgcg tacctagggc ttaaggggcc tcaggctggc actcgaaacc aggcgttctc    1920
atttcccttt ggcatcaccc tgaacggctg tgcctggagc tggcgcgggg ctgaagaggg    1980
gaggaaatac atgtgaggaa aatcagagga gagggtcggg aacagatgtg ggcataaagg    2040
gaaggcctct gacttgaaat aaacaaatag gagtcccgca gctggaagga caaatccttt    2100
cacgtcgcgg gtgatgtggg attggggcga ttttgctctc cctttgttct ttcccctgcc    2160
ttccacgttt ccagggtatt tgattgatgt ctgtcttctc tgttaagtta ttccaccgtg    2220
aggagagagc cggtggcagt acctggcacg cagcgggcgc ccagtataga cctgctgaac    2280
aaacgaatgg attcaggggc tgctgtgtcc ccctcaccca ccccccgccc cctatgtgtc    2340
cacagcgccc cgcacgtagt aggcgacccc taaacatctg tacagcaaat gatttgcaag    2400
ttttcggcgc tgagcacgtg gagctttgga aaccaggaca gcaaatgagt gtctcggaga    2460
ccacaaaagc ggttccggcg cgtgcgaaag gcggtggctg ggcgacggcg gagggaacgg    2520
cgcagagcgg ggcgccccgc cgggagcgct gcctgcgtgg cgcccgaggc ggggcgcgg    2580 ggggccgcgc atagcacgtg ctcgtctggg agccggccgg gccgaggcgg gcgcgcgtgt    2640
gcgcgtgggg cgtggggtgt gtgcccgcgc cgtgccccc gcgtgtgctg ccgggcgggc    2700
gccggcgtga gtcacggcgg ggctagcctt tataacggcc cggaggctcg cgggagccgc    2760
cgcgcccgtc cgcccgccgc tccgcgctcc acccagcgca                          2800
```

SCREENING AND THERAPEUTIC METHODS RELATING TO NEUROGENESIS

This application is based on, and claims the benefit of, U.S. Provisional Application No. 60/416,202, filed Oct. 4, 2002, which is incorporated herein by reference.

This invention was made in part with government support under grant number NIH MH57889 awarded by the National Institutes of Health. The United States Government has certain rights in this invention.

BACKGROUND OF THE INVENTION

1. Field of the Invention

This invention relates generally to the fields of G-protein coupled receptor signaling and therapy and, more specifically, to compounds and methods for modulating prokineticin receptor signaling and neurogenesis.

2. Background Information

In recent years, neurodegenerative disease has become an increasingly important concern due to the expanding elderly population, which is at greatest risk for developing Alzheimer's Disease, Parkinson's Disease and other debilitating neurodegenerative diseases. Neural damage as a result of stroke or trauma to the brain or spinal cord is also a leading cause of death and disability.

Providing a supply of new, functional neural cells at the site of the lesion, including new neurons, astrocytes and glial cells, has been proposed as a means to ameliorate neural degeneration or damage. One proposed strategy for achieving this goal is to transplant neural stem and progenitor cells into the brain or spinal cord, such that they develop into specialized neural cells. Another strategy is to boost endogenous neurogenesis by delivering biologically active molecules to the brain or spinal cord, so as to stimulate the proliferation, differentiation and migration of endogenous neural stem or progenitor cells. Ideally, with either approach, the new cells will correctly reconstruct neuronal circuits, produce neurochemically active substances, and remyelinate damaged axons.

However, the development of effective therapies for treating neural disorders is currently limited by the lack of understanding of the mechanisms that control neurogenesis. To develop improved therapies will thus require the identification of signal transduction pathways involved in neurogenesis and the regulators of these pathways. By identifying such pathways and regulators, new drugs can be developed that modulate neurogenesis in either ex vivo or in vivo applications.

Thus, there exists a need to identify compounds and methods for modulating neurogenesis. The invention satisfies this need and provides related advantages as well.

SUMMARY OF THE INVENTION

The invention provides methods of identifying compounds that modulate neurogenesis. The methods involve providing a compound that modulates prokineticin receptor signaling; contacting a neural stem or progenitor cell with the compound; and determining the ability of the compound to modulate neurogenesis.

The invention also provides methods for modulating neurogenesis. The methods involve contacting a neural stem or progenitor cell with an effective amount of a compound that modulates prokineticin receptor signaling. Such methods are useful in both ex vivo and in vivo therapeutic applications.

BRIEF DESCRIPTION OF THE DRAWINGS

FIGS. 1A and 1B are bright field images; FIGS. 1C and 1D are dark-field images; FIGS. 1E and 1F are Nissl staining.

FIGS. 1A, 1D and 1F are bright field images; FIGS. 1B and 1F are dark field images; FIGS. 1C and 1G are Nissl staining. PKR2 mRNA is also expressed in sporadic cells or cell groups in different brain regions, for instance, cortical areas (FIG. 1F).

FIG. 4 shows the results of in situ hybridization of a coronal section of adult mouse brain using a PK2 riboprobe. Expression of PK2 mRNA is seen in the olfactory bulb. FIG. 1A, bright field image; FIG. 1B, dark field image; FIG. 1C, Nissl staining.

FIG. 6 shows the amino acid or nucleotide sequences designated SEQ ID NOS:1-21. A predicted cyclic AMP responsive element in the human PK1 promoter (SEQ ID NO:17) is indicated in bold with underlining.

FIG. 7 shows the acute effects of PK2 administration on BrdU incorporation of neuroblasts of the subventricular zone (SVZ). FIG. 7A shows representative images of BrdU immunofluorescence of neurons from PK2-treated and control animals.

DETAILED DESCRIPTION OF THE INVENTION

Figure 1:
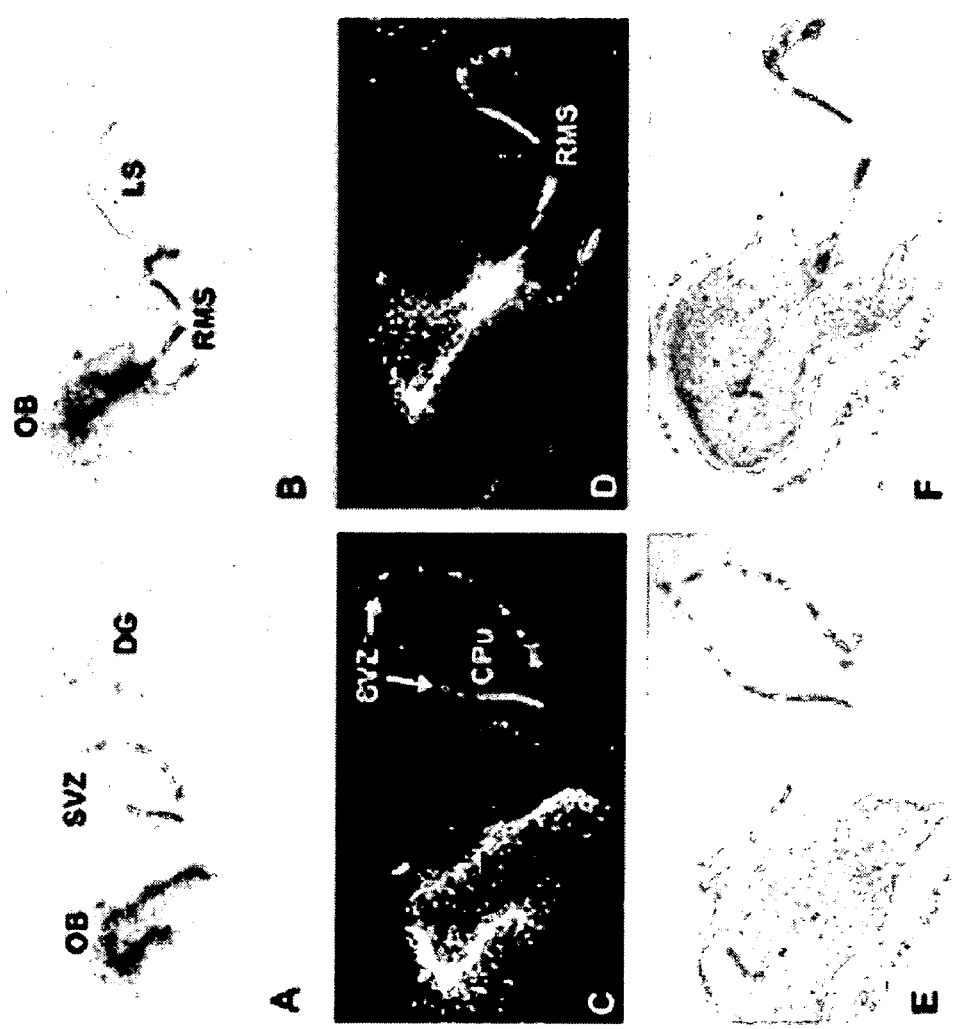
FIG. 1 shows the results of in situ hybridization of a sagittal section of adult mouse brain using a PKR2 3' untranslated region (UTR) riboprobe. Expression of PKR2 mRNA is seen in the subventricular zone (SVZ) of the lateral ventricle, olfactory bulb, olfactory ventricle, and dentate gyrus of hippocampus. RMS: rostral migratory system; OB: olfactory bul; CPu: caudate putamen.
Figure 2:
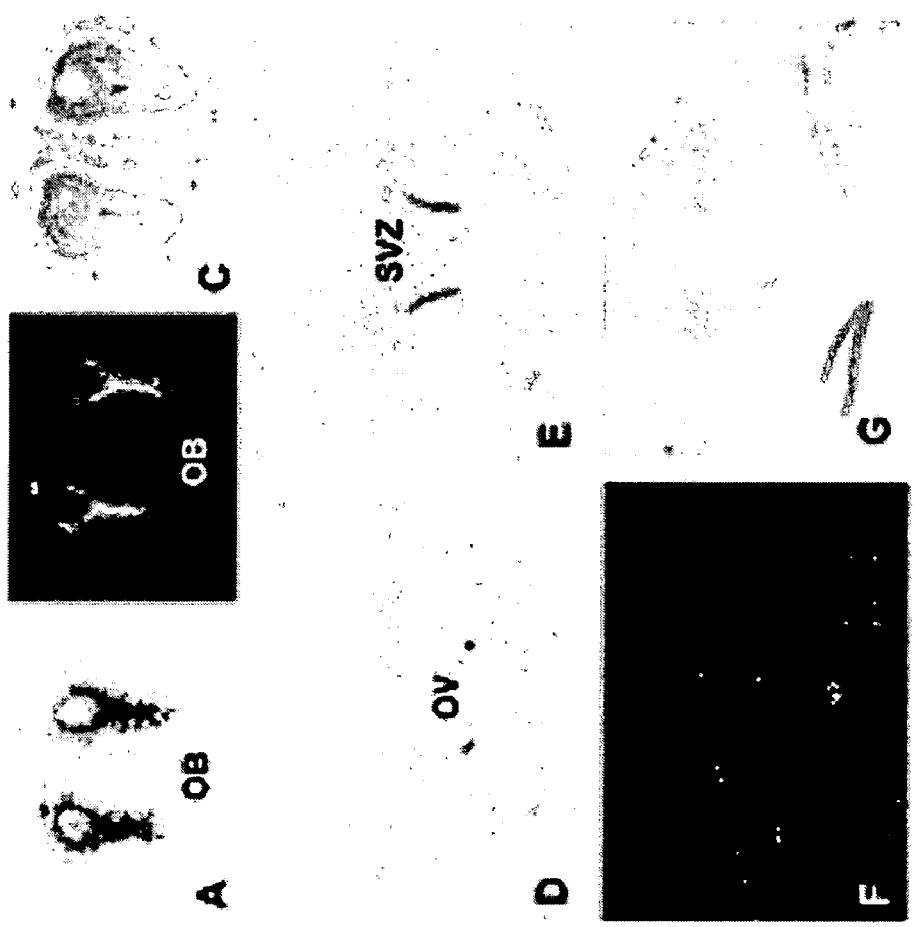
FIG. 2 shows the results of in situ hybridization of a coronal section of adult mouse brain using a PKR2 3' UTR riboprobe. Expression of PKR2 mRNA is seen in the SVZ of lateral ventricle, olfactory bulb, olfactory ventricle. OV: olfactory ventricle; Cx: cortex.
Figure 3:
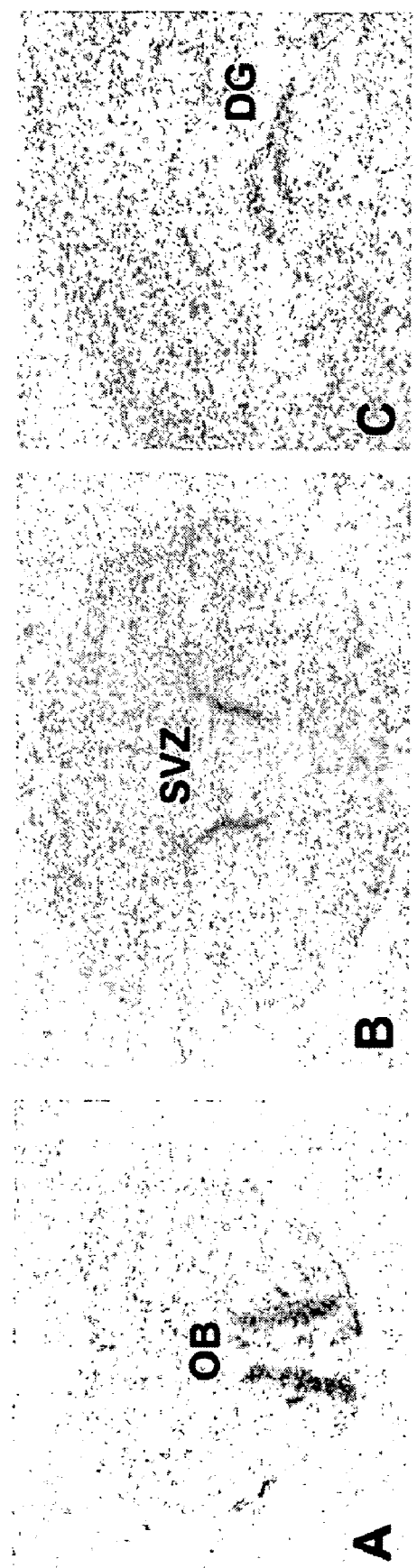
FIG. 3 shows the results of in situ hybridization of a coronal section of adult mouse-brain using a PKR1 3' UTR riboprobe. Expression of PKR1 mRNA is seen in the SVZ of lateral ventricle, olfactory bulb, and dentate gyrus of hippocampus. All panels show bright field images.
Figure 5:
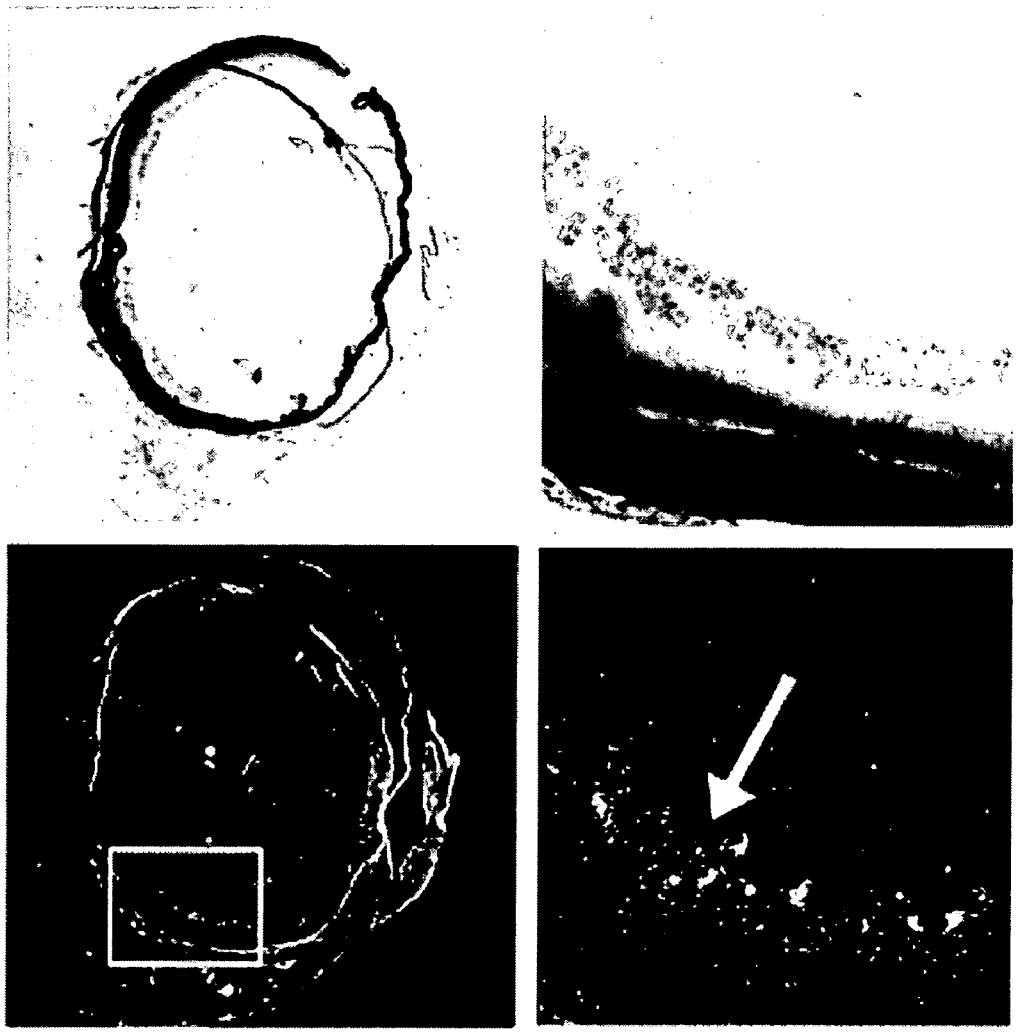
FIG. 5 shows the results of in situ hybridization of adult mouse retina with a PKR2 3'UTR riboprobe. Upper left: Dark field image of the eye; upper right: Nissl staining of the eye; lower left: expression of PKR2 in retina; lower right: Nissl staining.

The present invention relates to the determination that prokineticins effectively promote neurogenesis in rats. Based on this determination of this important pharmacological role of prokineticins, the invention provides screening methods for identifying compounds that modulate neurogenesis and therapeutic methods for modulating neurogenesis in mammals.

As disclosed in Example V, administration of recombinant human prokineticin 2 (PK2) to adult rats via intracerebroventricular infusion resulted in an increased number of newly developed neurons in the forebrain. Specifically, incorporation of the cell proliferation marker BrdU was at least two-fold higher in the subventricular zone in rats treated with PK2 in comparison to control animals. Also disclosed herein are the observations that mRNAs for two related GPCRs, designated prokineticin receptor 1 (PKR1) and prokineticin receptor 2 (PKR2), are expressed at high levels in the subventricular zone (SVZ) of the lateral ventricle, the olfactory bulb/olfactory ventricle, and the dentate gyrus of the hippocampus of adult mouse brain (see Example I). Further disclosed in Example II is that mRNA for PKR2 is also expressed in the inner nuclear layer of the adult mouse retina. mRNA for prokineticin 2 (PK2), which is an agonist of both PKR1 and PKR2, is expressed in both the olfactory bulb and the dentate gyrus of the hippocampus of the adult mouse brain. Non-neurogenic surrounding tissues express PKR1, PKR2 or PK2 at much lower levels. These findings indicate a role for signaling through prokineticin receptors in the regulation of neurogenesis.

Methods for modulating neurogenesis have a variety of important applications, including for treating individuals having, or who are likely to develop, disorders relating to neural degeneration, neural damage and neural demyelination, as described in more detail below. Therapeutic methods of modulating neurogenesis include both drug-based therapies, in which compounds that modulate neurogenesis are administered to an individual, and cell-based therapies, in which neural cells generated, propagated or genetically modified ex vivo using compounds that modulate neurogenesis are transplanted into the nervous system of an individual. Developing methods for modulating neurogenesis ex vivo are also useful for advancing understanding of the complex processes of neural proliferation and differentiation, which can lead to development of additional compounds and approaches for diagnosing and treating disorders of the nervous system.

Accordingly, the invention provides methods of screening for compounds that modulate neurogenesis. The invention screening methods involve providing a compound that modulates PKR signaling, and determining the ability of the compound to modulate neurogenesis.

The invention also provides methods of modulating neurogenesis by contacting a neural stem or progenitor cell with an effective amount of a compound that modulates PKR signaling.

A compound that modulates PKR signaling will generally promote signaling in a suitable signaling assay, as described below, by at least about 10%, such as at least 25%, 50%, 100%, 500% or more, or alternatively reduce signaling in a suitable signaling assay by at least about 10%, such as at least 25%, 50%, 90% or more, in comparison to a control compound.

It will be appreciated that PKR signaling can be modulated either directly or indirectly, and by altering either activity or abundance of either a PKR receptor or of a PKR ligand. For example, PKR signaling can be modulated directly, such as by contacting the PKR with an agonist or antagonist. PKR signaling can also be modulated indirectly, such as by altering PKR expression, localization, stability, or ability to bind effector molecules, or by altering prokineticin (PK) expression, secretion, stability or ability to bind or activate a PKR. Various methods of modulating PKR signaling are described below, following a description of prokinetin receptors and prokineticins. Other general approaches to qualitatively or quantitatively modulate signaling through G-protein coupled receptors are known in the art, and can be applied in accordance with the invention to prokineticin receptors given the guidance herein.

As used herein, the term "prokineticin receptor" or "PKR" refers to a heptahelical membrane-spanning polypeptide that binds to a prokineticin and signals through a G-protein coupled signal transduction pathway in response to prokineticin binding. Prokineticin receptors are believed to couple exclusively to the Gα subtype known as Gαq, and thereby mediate intracellular calcium mobilization in response to agonists.

A prokineticin receptor can have the naturally-occurring amino acid sequence of a PKR from any species, or can contain minor modifications with respect to the naturally-occurring sequence. For example, a PKR can be a mammalian PKR, such as human PKR1 (SEQ ID NO:1; GenBank Accession No. AAM48127; also called. GPR73, fb41a, hZAQ, hGPRv21 and EG-VEGF receptor-1; Lin et al., *J. Biol. Chem.* 277:19276-19280 (2002), Masuda et al., *Biochem. Biophys. Res. Commun.* 293:396-402 (2002), WO 00/34334, WO 01/48188 and WO 01/16309); human PKR2 (SEQ ID NO:2; GenBank Accession No. AAM48128; also known as I5E, hRUP8 and hZAQ2; Lin et al., supra (2002), Masuda et al., supra (2002), WO 98/46620, WO 01/36471 and WO 02/06483); mouse PKR1 (SEQ ID NO:3; GenBank Accession No. AAM49570; Cheng et al., *Nature* 417:405-410 (2002) and WO 02/06483); mouse PKR2 (SEQ ID NO:4; GenBank Accession No. AAM49571; Cheng et al., supra (2002) and WO 02/06483); rat PKR1 (WO 02/06483); rat PKR2 (WO 02/06483); monkey PKR2 (also known as AXOR8; WO 01/53308); bovine PKR1 (Masuda et al., supra (2002), or a PKR of another mammalian species, such as other primate, dog, cat, pig, sheep or goat; or a PKR of another vertebrate species, such as an amphibian, reptile, fish or bird.

Based on the high degree of homology between the nucleotide sequences encoding PKR1 and PKR2, and between PKR types across species, the skilled person can readily identify and clone a PKR from any other species. For example, other PKRs can be identified from nucleic acid libraries using standard molecular biology approaches such as hybridization and polymerase chain reaction (PCR) techniques. Additionally, PKRs from other species can be identified from nucleic acid sequence databases specific for the species of interest. Methods of identifying, isolating and propagating homologous nucleic acid molecules are well known in the art and described, for example, in Sambrook et al., Molecular Cloning: A Laboratory Manual, 3rd ed., Cold Spring Harbor Press, Plainview, N.Y. (2001) and Ausubel et al. (Current Protocols in Molecular Biology, John Wiley & Sons, New York ((current supplement)).

Likewise, based on the high degree of homology among PKR polypeptides, the skilled person can readily identify a cell from another species or from an expression library that expresses a PKR, using PKR-specific antibodies. Methods of preparing and using antibodies to identify polypeptides are well known in the art and described, for example, in Harlow and Lane, *Antibodies: A Laboratory Manual*, Cold Spring Harbor Laboratory Press (1988)

A prokineticin receptor can also contain minor modifications with respect to a naturally-occurring PKR, so long as the PKR retains its ability to bind to, and signal in response to, a prokineticin, such as a human PK1 or human PK2 described below.

A prokineticin receptor that contains minor modifications with respect to a naturally-occurring PKR can contain one or more additions, deletions, or substitutions of natural or non-natural amino acids relative to the naturally-occurring polypeptide sequence. Such a modification can be, for example, a conservative change, wherein a substituted amino acid has similar structural or chemical properties, for example, substitution of an apolar amino acid with another apolar amino acid, substitution fo a charged amino acid with another amino acid of similar charge, and the like. Such a modification can also be a non-conservative change, wherein a substituted amino acid has different but sufficiently similar structural or chemical properties so as to not adversely affect the desired biological activity. Further, a minor modification can be the substitution of an L-configuration amino acid with the corresponding D-configuration amino acid with a non-natural amino acid.

In addition, a minor modification can be a chemical or enzymatic modification to the polypeptide, such as replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

Those skilled in the art can determine whether minor modifications to a naturally occurring prokineticin receptor sequence is advantageous in a method of the invention. Minor modifications are useful, for example, to enhance the stability, selectivity, bioactivity of a receptor. Modified PKR polypeptides can be prepared, for example, by recombinant methods, by synthetic methods, by post-synthesis chemical or enzymatic methods, or by a combination of these methods, and tested for ability to bind a prokineticin or signal through a G-protein coupled signal transduction pathway.

Those skilled in the art can readily predict regions in a prokineticin receptor amino acid sequence that can be modified without abolishing binding or signaling. Such prediction can be based on sequence analysis, structure-function studies, and computer algorithms. For example, comparisons of amino acid sequences of PKR2 and PKR1, and of PKRs across species, can provide guidance in determining amino acid residues that are tolerant of modification. Further, a large number of published GPCR-structure-function studies have indicated regions of GPCRs involved in ligand interaction, G-protein coupling and in forming transmembrane regions, and indicate regions of GPCRs tolerant of modification (see, for example, Burstein et al., *J. Biol. Chem.*, 273:24322-24327 (1998) and Burstein et al., *Biochemistry*, 37(12):4052-4058 (1998)). In addition, computer programs known in the art can be used to determine which amino acid residues of a polypeptide can be modified without abolishing activity (see, for example, Eroshkin et al., *Comput. Appl. Biosci.* 9:491-497 (1993); Gueros et al., *J. Mol. Biol.* 320: 369-387(2002)). These methods can likewise be applied to PKRs.

For certain applications, a PKR has at least 80%, such as at least 85%, 90%, 95%, 97%, 99% or greater identity with either human PKR1 (SEQ ID NO:1) or with human PKR2 (SEQ ID NO:2).

That a presumptive PKR, such as a PKR from another species or a modified PKR is actually a PKR can be confirmed by prokineticin binding assays and G-protein coupled receptor signaling assays known in the art (see, for example, U.S. published application 20020115610A1, Lin et al., supra (2002) and Masuda et al., supra (2002)), and described further below.

Depending on the intended application, the skilled person can determine an appropriate form for the PKR, such as in a live animal, a tissue, a tissue extract, a cell, a cell extract, or in substantially purified form. For example, for receptor binding or signaling assays, the PKR will typically be either endogenously expressed or recombinantly expressed at the surface of a cell.

Cells that endogenously express a PKR are well known in the art, and include, for example, M2A7 melanoma cells (available from American Type Culture Collection as ATCC CRL-2500), M2 melanoma cells (Cunningham et al., *Science* 255;325-327 (1992)) and RC-4B/C pituitary tumor cells (ATCC CRL-1903)(see U.S. 20020115610A1). Other cells that endogenously express a PKR include, for example, ileal and other gastrointestinal cells (see U.S. 20020115610A1), endothelial cells such as BACE cells (Masuda et al., supra (2002)), and endocrine cells (Lin et al., supra (2002)). As disclosed herein, other cells that express PKR include neural stem and progenitor cells, including such cells in the subventricular zone of the lateral ventricle, the olfactory bulb/olfactory ventricle, the dentate gyrus of the hippocampus, and the inner nuclear layer of the retina.

Methods of recombinantly expressing a PKR are also well known in the art (see, for example, Lin et al., supra (2002) and Masuda et al., supra (2002)). Host cells suitable for recombinantly expressing polypeptides are well known in the art, and include bacterial cells (e.g. *E. coli*), insect cells (e.g. *Drosophila*), yeast cells (e.g. *S. cerevisiae, S. pombe,* or *Pichia pastoris*), and vertebrate cells (e.g. mammalian primary cells and established cell lines; and amphibian cells, such as *Xenopus* embryos and oocytes). Vectors appropriate for expressing polypeptides in the particular host cell are also well known in the art, and include, for example, vectors derived from a virus, such as a bacteriophage, a baculovirus or a retrovirus, and vectors derived from bacteria or a combination of bacterial sequences and sequences from other organisms, such as a cosmid or a plasmid. Suitable expression vectors generally contain elements such as an origin of replication compatible with the intended host cells; constitutive or inducible promoter sequences; transcription termination and RNA processing signals; one or more selectable markers compatible with the intended host cells; one or more multiple cloning sites; and optionally contain tag sequences that facilitate expression or purification of the encoded polypeptide. Methods of recombinantly expressing polypeptides are well known in the art and described, for example, in Sambrook et al., supra (2001) and Ausubel et al. supra (current supplement).

As used herein, the term "prokineticin" or "PK" refers to a peptide that binds to a prokineticin receptor and elicits signaling by the receptor through a G-protein coupled signal transduction pathway.

A prokineticin can have the naturally-occurring amino acid sequence of a PK from any species, or can contain minor modifications with respect to the naturally-occurring sequence. For example, a PK can be a mammalian PK, such as human PK1 (SEQ ID NO:5; GenBank Accession No. P58294; also known as endocrine-gland-derived endothelial growth factor or EG-VEGF, TANGO 266, PRO 1186 and Zven2; Li et al., supra (2001), LeCouter et al., *Nature* 412: 877-884 (2001), WO 01/36465, WO 99/63088 and WO 00/52022; human PK2 (GenBank Accession No. Q9HC23; isoform 1, SEQ ID NO:6, Wechselberger et al., *FEBS Lett.* 462:177-181 (1999) or isoform 2, SEQ ID NO:7; also known as Zven1, Li et al., supra (2001)); mouse PK1 (SEQ ID NO:8; GenBank Accession No. AAM49573); mouse PK2 (SEQ ID NO:9; GenBank Accession No. AAM49572); rat PK1 (SEQ ID NO:10; GenBank Accession No. AAM09104; Masuda et al., supra (2002)); rat PK2 (SEQ ID NO:11; GenBank Accession No. AAM09105; Masuda et al., supra (2002)), or a PK of another mammalian species, such as other primate, dog, cat, pig, cow, sheep or goat.

A PK can alternatively be a PK of another vertebrate species, such as a snake, frog or toad. For example, a PK can be black mamba PK (SEQ ID NO:12; GenBank-Accession No. P25687; also known as MIT1; Schweitz et al., *FEBS Lett.* 461:183-188 (1999)); *Bombina variegata* frog PK (SEQ ID NO:13; GenBank Accession No. Q9PW66; also known as Bv8; Mollay et al., *Eur. J. Pharmacol.* 374:189-196 (1999); *Bombina maxima* toad PK (SEQ ID NO:14; GenBank Accession No. AAN03822), or a PK from another vertebrate species, such as an amphibian, reptile, fish or bird.

A prokineticin can also contain minor modifications with respect to a naturally-occurring PK, so long as the PK retains its ability to bind to, and elicit signaling by, a prokineticin receptor, such as a human PKR1 or PKR2 as described above. Examples of types of suitable minor modifications have been described above with respect to PKRs, and also apply to PKs. Minor modifications to a PK can be useful, for example, for applications in which it is desired to enhance a property of the PK, such as stability, bioavailability, bioactivity or specificity.

Specific examples of prokineticins that are modified from naturally-occurring sequences while retaining activity include human prokineticin chimeras having SEQ ID NO:15 (chimera of PK1 at N-terminus, PK2 at C-terminus) and SEQ ID NO:16 (chimera of PK2 at N-terminus, PK1 at C-terminus). Chimeras between PK1 and PK2 within species, or between prokineticins across species, so long as they retain PK activity, are also considered prokineticins.

As described in U.S. 20020115610A1, prokineticins are not tolerant of additions, deletions or substitutions at the N-terminal 6 amino acids conserved across all species (AVITGA), or at any of the 10 conserved cysteine residues. However, modifications at other internal residues are tolerated, as are modifications at residues C-terminal to the tenth cysteine.

For certain applications, a PK has at least 40%, such as at least 45%, 50%, 60%, 70%, 80%, 85%, 90%, 95%, 97%, 99% or greater identity-with either human PK1 (SEQ ID NO:5) or with human PK2 (SEQ ID NO:6).

That a presumptive PK, such as a PK from another species or a modified PK is actually a PK can be confirmed by prokineticin binding assays and G-protein coupled receptor signaling assays known in the art (see, for example, U.S. 20020115610A1, Lin et al., supra (2002) and Masuda et al., supra (2002)), and described further below.

Depending on the intended application, the skilled person can determine an appropriate form for the PK, such as in a live animal, a tissue, a tissue extract, a cell, a cell extract, or in substantially purified form. A prokineticin can be substantially purified from any tissue, cell or body fluid source that endogenously contains PK peptide, or can be produced recombinantly and then substantially purified. Sources of endogenous PK include milk (Masuda et al., supra (2002)), venom (Masuda et al., supra (2002); Mollay et al., *Eur. J. Pharmacol.* 374:189-196 (1999)), various fetal and adult tissues, including GI tract, liver, spleen, testis and placenta (U.S. 20020115610A1) and, as disclosed herein, neural stem and progenitor cells. Methods of substantially purifying prokineticins from such sources are described in the aforementioned references.

Methods of recombinantly expressing prokineticins are also known in the art (see U.S. 20020115610A1 and Masuda et al., supra (2001) for examples of bacterial expression and WO 01/36465 and WO 00/52022 for-examples of eukaryotic expression). Such methods can involve initially expressing the PK as a fusion protein, such as a fusion with a glutathione-S-transferase tag, Fc tag, 6X His tag, myc epitope, or other tag sequences known in the art. Methods of substantially purifying recombinantly expressed prokineticins, and for removing optional tag sequences, are also known in the art. For example, U.S. 20020115610A1 describes conditions for refolding and purifying recombinantly expressed prokineticins that minimize protein aggregation, and also describes methods of confirming correct disulfide bond formation.

In one embodiment, the invention screening and therapeutic methods involve providing a compound that is a prokineticin receptor agonist or antagonist. A PKR agonist or antagonist can optionally be selective for PKR1 or PKR2, or alternatively be equally active with respect to both PKR1 and PKR2.

As used herein, the term "prokineticin receptor, agonist" refers to a compound that promotes or enhances normal G-protein coupled signal transduction through a PKR. A PKR agonist can act by any agonistic mechanism, such as by directly binding a PKR at the normal ligand binding site, thereby promoting receptor signaling. A PKR agonist can also act indirectly, for example, by potentiating the binding activity of the endogenous ligand, or by altering the conformation of the PKR so as to increase its signaling activity.

Examples of PKR agonists include naturally-occurring, chimeric and modified PK peptides, as described above. PKR agonists can also include peptidomimetics of such PK peptides. Methods of preparing peptidomimetics are known in the art and reviewed, for example, in Ripka et al., *Curr. Opin. Chem. Biol.* 2:441-452 (1998) and al-Obeidi et al., *Mol. Biotechnol.* 9:205-223 (1998). Other PKR agonists include compounds identified as such by the screening assays described below. An exemplary partial agonist is PK2-insert (insertion of 23 amino acids between exon 2 and exon 3 of PK2) and an exemplary weak agonist is GIL-PK1 (tripeptide Gly-Ile-Leu added to the N-terminus of PK1).

As used herein, the term "prokineticin receptor antagonist" refers to a compound that inhibits or decreases normal G-protein coupled signal transduction through a PKR. A PKR antagonist can act by any antagonistic mechanism, such as by directly binding a PKR at the PK binding site, thereby inhibiting binding between the PKR and its ligand. A PKR antagonist can also act indirectly, for example, by binding a PK, or by altering the conformation or state of phosphorylation or glycosylation of a PKR, thereby affecting its ability to bind or respond to ligand. The term "PKR antagonist" is also intended to include compounds that act as "inverse agonists," meaning that they decrease PKR signaling from a baseline amount of constitutive signaling activity.

Examples of PKR antagonists include peptides with either a single N-terminal residue addition or a single N-terminal residue deletion with respect to human PK1 and PK2 (see U.S. 20020115610A1). Peptides having similar modifications to other prokineticins, or other modifications to the conserved N-terminal six residues of human or other prokineticins, such as more extensive additions or deletions and substitutions, can also be PKR antagonists. An exemplary PKR antagonist is MVITGA.

Other examples of PKR antagonists are antibodies selective for a PKR or a PK. The term "antibody" is intended to include both polyclonal and monoclonal antibodies, as well as antigen binding fragments of such-antibodies (e.g. Fab, F(ab')$_2$, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

Methods of preparing and isolating antibodies, including polyclonal and monoclonal antibodies, using peptide and polypeptide immunogens, are well known in the art and are described, for example, in Harlow and Lane, *Antibodies: A Laboratory Manual*, Cold Spring Harbor Laboratory Press (1988). Non-naturally occurring antibodies can be constructed using solid phase peptide synthesis, can be produced recombinantly or can be obtained, for example, by screening combinatorial libraries consisting of variable heavy chains and variable light chains. Such methods are described, for example, in Huse et al. *Science* 246:1275-1281 (1989); Winter and Harris, *Immunol. Today* 14:243-246 (1993); Ward et al., *Nature* 341:544-546 (1989); Hilyard et al., *Protein Engineering: A practical approach* (IRL Press 1992); and Borrabeck, *Antibody Engineerinq*, 2d ed. (Oxford University Press 1995).

A prokineticin receptor agonist will generally have an $EC_{50}$ that is no more than 2-fold, 5-fold, 10-fold, 50-fold, 100-fold or 1000-fold higher or lower than the $EC_{50}$ for human PK1 or PK2 in the particular assay. For therapeutic applications described below, a prokineticin receptor agonist preferably has an $EC_{50}$, and a prokineticin receptor antagonist preferably has an $IC_{50}$, of less than about $10^{-7}$ M, such as less than $10^{-8}$ M, and more preferably less than $10^{-9}$ or $10_{-10}$ M. However, depending on the stability, selectivity and toxicity of the compound, a prokineticin receptor agonist with a higher $EC_{50}$, or a prokineticin receptor antagonist with a higher $IC_{50}$, can also be useful therapeutically.

Signaling assays to identify or confirm the activity of PKR agonists and antagonists are known in the art. Because PKRs are $G\alpha q$-coupled receptors, signaling assays typically used with other $G\alpha q$-coupled GPCRs can be used to determine PKR signaling activity. $G\alpha q$-coupled GPCRs, when bound to ligand, activate phospholipase C (PLC), which cleaves the lipid phosphatidylinositol 4,5-bisphosphate (PIP2) to generate the second messengers inositol 1,4,5-trisphosphate (IP3) and diacylglycerol (DAG). These second messengers increase intracellular $Ca^{2+}$ concentration and activate the MAP kinase cascade. The change in activity of PLC, or in abundance of downstream messengers, is a reflection of GPCR activation.

The specificity of $G\alpha$ subunits for cell-surface receptors is determined by the C-terminal five amino acids of the $G\alpha$. Thus, if it is desired to assay a GPCR signaling pathway other than a typical $G\alpha q$ pathway, a chimeric $G\alpha$ containing the five C-terminal residues of $G\alpha q$ and the remainder of the protein corresponding to another $G\alpha$ can be expressed in a cell such that the PKR is coupled to a different signaling pathway (see, for example, Conklin et al., *Nature* 363:274-276 (1993), and Komatsuzaki et al., *FEBS Letters* 406:165-170 (1995)). For example, a PKR can be coupled to a $G\alpha s$ or $G\alpha i$, and adenylate cyclase activation or inhibition assayed by methods known in the art.

Depending on the $G\alpha$ and the assay system, GPCR signals that can be determined include, but are not limited to, calcium ion mobilization; increased or decreased production or liberation of arachidonic acid, acetylcholine, diacylglycerol, cGMP, cAMP, inositol phosphate and ions; altered cell membrane potential; GTP hydrolysis; influx or efflux of amino acids; increased or decreased phosphorylation of intracellular proteins; and activation of transcription of an endogenous gene or promoter-reporter construct downstream of any of the above-described second messenger pathways.

A variety of cell-based GPCR signaling assays, including assays performed in bacterial, yeast, baculovirus/insect systems and mammalian cells, are reviewed, for example, in Tate et al., *Trends in Biotecha.* 14:426-430 (1996). More recently developed GPCR signaling assays include, for example, AequoScreen, which is a cellular aequorin-based functional assay that detects calcium mobilization (LePoul et al., *J. Biomol. Screen.* 7:57-65 (2002)); MAP kinase reporter assays (Rees et al., *J. Biomol. Screen.* 6:19-27 (2001); and fluorescence resonance energy transfer (FRET) based PLC activation assays (van der Wal, *J. Biol. Chem.* 276:15337-15344 (2001)). Several examples of PKR signaling assays are described in Lin et al., supra (2002) and in Masuda et al., supra (2002).

Optionally, a compound can initially be tested to determine whether it binds a PKR, such compounds being likely to act as PKR agonists or antagonists. Competitive and non-competitive binding assays for detecting ligand binding to a receptor are described, for example, in Mellentin-Micelotti et al., *Anal. Biochem.* 272:182-190 (1999); Zuck et al., *Proc. Natl. Acad. Sci. USA* 96:11122-11127 (1999); and Zhang et al., *Anal. Biochem.* 268;134-142 (1999). Examples of PKR binding assays are described in Lin et al., supra (2002) and in Masuda et al., supra (2002).

For certain applications of the invention methods it will be advantageous to employ a compound that modulates PKR signaling by a mechanism other than by acting as a prokineticin receptor agonist or antagonist.

Thus, in one embodiment, a compound that modulates PKR signaling is a compound that modulates endogenous prokineticin mRNA expression. A compound that modulates PK expression can be, for example, an expressible nucleic acid molecule that encodes a PK, or that serves to inhibit PK gene expression, such as an antisense nucleic acid molecule, a ribozyme or an RNA interference (RNAi) molecule. Methods of preparing such nucleic acid molecules and using them in ex vivo and in vivo applications are known in the art. For example, viral delivery systems are reviewed in Mah et al., *Clin. Pharmacokinet.* 41:901-911; non-viral delivery systems in Li et al., *Curr. Gene Ther.* 1:201-226 (2001); RNAi in Hannon, *Nature* 418:244-251 (2002); antisense in Galderisi et al., *J. Cell Physiol.* 181:251-257 (1999) and ribozymes in Lewin et al., *Trends Mol. Med.* 7:221-228 (2001)).

A compound that enhances endogenous PK mRNA expression can also be a compound identified by a screening assay. In an exemplary screening assay, an animal, tissue or cell that endogenously expresses a PK is contacted with one or more candidate compounds. PK mRNA can be detected and quantitated using methods known in the art, such as hybridization with a detectable probe or primer, or PCR, and the mRNA level compared to a control. Such methods are described, for example, in Sambrook et al., supra (2001) and Ausubel et al. supra (current supplement). Alternatively, PK peptide can be detected and quantitated using methods known in the art, such as by assaying direct or competitive binding to an antibody or receptor. Such methods are described, for example, in Harlow and Lane, supra (1988).

Alternatively, a screening assay to identify a compound that enhances endogenous PK mRNA expression can employ a PK promoter operatively linked to a nucleic acid molecule encoding a reporter gene, such as β-lactamase, luciferase, green fluorescent protein or β-galactosidase. In such assays, a cell transfected with the promoter-reporter construct is contacted with a candidate compound, and the expression of reporter gene product detected by methods known in the art which depend on the particular reporter.

The nucleotide sequences of PK1 and PK2 promoters are known in the art, and human and mouse promoter sequences are set forth herein as SEQ ID NOS:17-21. A smaller portion of a prokineticin promoter sequence can alternatively be used, such as a region of at least about 100 nucleotides, such as at least about 200, 250, 300, 500, 1000, 1500, 2000, 2500 or more nucleotides upstream of the transcriptional start site.

Both the PK1 promoter and the PK2 promoters contain presumptive cyclic-AMP response elements (CREs), in that they contain the core CRE consensus sequence CGTCA. In the human PK2 promoter, for example, the presumptive CRE is about 200 nucleotides upstream of the transcriptional start site. Thus, it is contemplated that compounds that modulate prokineticin mRNA expression include compounds known or expected to modulate cyclic-AMP production and/or MAP kinase activation, such as various growth factors.

In another embodiment, a compound that modulates PKR signaling is a compound that enhances endogenous prokineticin peptide production or secretion. Methods of detecting prokineticin production secretion can include bioassays, binding assays, immunoassays and the like, and can be adapted to prokineticins based on peptide assays known in the art and the guidance provided herein.

In a further embodiment, a compound that modulates PKR signaling can be a compound that modulates PKR mRNA or protein expression. A compound that modulates PKR expression can be, for example, an expressible nucleic acid molecule that encodes a PKR, or that serves to inhibit PKR gene expression, such as an antisense nucleic acid molecule, a ribozyme or an RNA interference (RNAi) molecule. Methods of preparing such nucleic acid molecules and using them are known in the art, as described above.

A compound that modulates PKR expression can also be a compound identified from a screening assay. In an exemplary screening assay, an animal, tissue or cell that endogenously expresses a PKR is contacted with one or more candidate compounds. Expression of PKR mRNA or protein can be detected and the level compared to a control using methods known in the art, such as methods analogous to those described above for detecting increased prokineticin mRNA or peptide expression.

The skilled person will appreciate that the above methods to identify compounds that modulate PKR signaling are exemplary. Alternative methods and mechanisms for modulating GPCR signaling by modulating abundance or activity of a PKR or its ligand are known in the art or can be determined based on the guidance herein.

In the screening assays described above, a candidate compound that is tested for its ability to modulate PKR signaling can be any type of biological or chemical molecule. For example, the candidate compound can be a naturally occurring macromolecule, such as a polypeptide, peptidomimetic, nucleic acid, carbohydrate, lipid, or any combination thereof. A candidate compound also can be a partially or completely synthetic derivative, analog or mimetic of such a macromolecule, or a small organic molecule, such as a molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several compounds that are known or predicted to act as PKR modulatory compounds. However, it will be appreciated that the larger the number of candidate compounds, the greater the likelihood of identifying a compound having the desired activity in a screening assay. Additionally, large numbers of compounds can be processed in high-throughput automated screening assays. Therefore, the term "one or more candidate compounds" can refer, for example, to 2 or more, such as 5, 10, 15, 20, 50 or 100 or more different compounds, such as greater than about $10^3$, $10^5$ or $10^7$ different compounds. Such candidate compounds can be assayed simultaneously, such as in pools of compounds or in parallel assays, or sequentially.

Assay methods for identifying compounds that modulate PKR signaling generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond to a PK. In this situation, the response of the test preparation to a candidate compound is compared to the response (or lack of response) of the control preparation to the same compound under substantially the same reaction conditions.

The methods of the invention involve contacting a neural stem or progenitor cell with a compound that modulates PKR signaling under conditions in which the compound can modulate neurogenesis.

As used herein, the term "neurogenesis" refers to the process by which neural stem and progenitor cells give rise to more differentiated neural cells. Neurogenesis encompasses proliferation of neural stem and progenitor cells, differentiation of these cells into new neural cell types, as well as migration and survival of the new cells. The term is intended to cover neurogenesis as it occurs during normal development, as well as neural regeneration that occurs following disease, damage or therapeutic intervention. Neurogenesis is reviewed, for example, in Okano et al., J. Neurosci. Res. 69:698-707 (2002).

A number of factors have been shown to modulate neurogenesis in adult mammals. For example, learning and environment enrichment have been shown to enhance survival of neural stem and/or progenitor cells, whereas stress has been shown to diminish proliferation of these cells. In animal models of epilepsy and stroke, neurogenesis is enhanced. At the biochemical level, a number of molecules have been shown to influence neurogenesis. For example, the growth factors EGF, bFGF, VEGF, IGF-1, and the monoamine neurotransmitters have been shown to stimulate neurogenesis, while high levels of corticosterone, glutamate, gamma-aminobutyric acid, and opioid peptides diminish neurogenesis.

As used herein, the term "neural stem cell" refers to a cell of the central nervous system that can self-replicate and can also give rise to cells of a plurality of neural cell lineages, such as astrocytes, oligodendrocytes and neurons.

As used herein, the term "neural progenitor cell" refers to a cell of the central nervous system that can proliferate but is more lineage-restricted in comparison with a neural stem cell. Neural progenitor cells include neuronal progenitor cells, which produce neurons, and glial progenitor cells that produce astroglial and/or oligodendroglial cells.

Neurogenesis has been shown to occur throughout adulthood in several neurogenic areas of the mammalian central nervous system, including the olfactory bulb (OB), the dentate gyrus (DG) of the hippocampus and the subventricular zone (SVZ). Low levels of neurogenesis have also been reported in the Ammon's horn. The new neuronal cells in the adult mammalian OB are generated from neural progenitor cells in the anterior part of the SVZ. The SVZ is a narrow zone of tissue in the wall of the lateral ventricle in the forebrain. The neural progenitor cells of the SVZ migrate to the OB via the rostro-migratory stream (RMS), where they differentiate into interneurons of the OB, known as granule cells and periglomerular cells. The neural progenitor cells of the adult DG are generated in the subgranular zone (SGZ) of the DG and differentiate into neuronal and glial cells in the granular layer of the DG. The newly generated neuronal cells extend axons into the CA3 region of the hippocampus as soon as 4-10 days after mitosis (reviewed in Taupin and Gage, *J. Neurosci. Res.* 69:745-749 (2002)).

Neural stem and/or progenitor cells have been isolated from diverse areas of the adult central nervous system, including the subventricular zone (SVZ), hippocampus, septum, striatum, cortex, olfactory bulb, the rostral extension of the SVZ, in different levels of the spinal cord, including cervical, thoracic, lumbar, and sacral levels. In the spinal cord, neural stem and/or progenitor cells can be isolated from the periventricular area and the parenchyma. Neural stem and/or progenitor cells have also been isolated and cultured from adult postmortem neural tissues (reviewed in Taupin and Gage, supra (2002)), and are present in the inner nuclear layer of the adult retina.

Neural stem cells express a number of selective immunocytochemical markers, including Nestin, an intermediate filament protein (Hockfield and McKay, *J. Neurosci.* 5:3310-3328 (1985)); Musashil (Msil), an RNA-binding protein (Sakakibara et al., *Dev. Biol.* 176:230-242 (1996)); and Soxl, a transcription factor (Pevny et al., *Development* 125:1967-1978 (1998)). These markers are also expressed by neural progenitor cells, albeit at lower levels. Neural stem and progenitor cells are also characterized by their expression of the polysialylated form of the neural cell adhesion molecule (PSA-NCAM; Rousselot et al., *J. Comp. Neurol.* 351:51-61(1995)) and by their expression of the fibroblast growth factor (FGF) and epidermal growth factor (EGF) receptors (Gritti et al., *J. Neurosci.* 19:3287-3297 (1999)). Other characteristics of neural stem and progenitor cells are known in the art and reviewed, for example, in Okano et al., supra (2002).

Compounds that modulate neurogenesis can act by enhancing or reducing neural stem and/or progenitor cell proliferation, differentiation, survival or migration. Assays to identify compounds that modulate neurogenesis can be performed either ex vivo or in vivo, as described below.

A compound that modulates neurogenesis will generally promote neurogenesis in a suitable neurogenesis assay, as described below, by at least about 10%, such as at least 25%, 50%, 100%, 500% or more, or alternatively reduce neurogenesis in such an assay by at least about 10%, such as at least 25%, 50%, 90% or more, in comparison to a control compound.

Modulation of neurogenesis can be evidenced following contacting the cells with the compound alone, or with the compound in combination with another neurogenic modulatory factor, such as EGF, FGF, or VEGF. Modulation of neurogenesis can also be evidenced under normal ex vivo or in vivo conditions, or under conditions that mimic neural disease or damage.

Neural stem and/or progenitor cells suitable for use in the assay methods described below can be obtained from mammals, including humans (post-mortem or following surgery) and experimental animals (such as rodents, non-human primates, dogs, cats and the like). Neural stem and/or progenitor cells can also be obtained from other vertebrates, including reptiles, amphibians, fish and birds, or from invertebrates. The human or animal can be male or female, can be fetal, young, adult or old, and can be normal or exhibiting or susceptible to a neural disease or disorder.

For certain applications, tissue explants can be used, whereas for others, dissociated cells or neurospheres can be obtained. Tissue explants or cells can be obtained from any neural tissue that contains neural stem or progenitor cells, including brain and spinal tissues as described above. Exemplary tissues include olfactory bulb (OB), the dentate gyrus (DG) of the hippocampus and the subventricular zone (SVZ) of the lateral ventricles. Example III describes a method of obtaining neural stem and/or progenitor cells from the lateral ventricles of adult mice. Other methods are known in the art (see, for example, U.S. Pat. No. 5,753,506; and Gritti et al., *J. Neurosci.* 16:1091-1100 (1996)).

In addition to primary cells, neural stem and/or progenitor cell lines can be used in neurogenesis assays, such as MHP36 cells of mouse hippocampal origin (Gray et al., *Philos. Trans. Royal Soc. Lond. B. Biol. Sci.* 354:1407-1421 (1999)), CSM14.1 cells of rat mesencephalic origin (Haas et al., *J. Anat.* 201:61-69 (2002)), and embryonic stem cells differentiated along the neural lineage.

In ex vivo neurogenesis assays, either proliferation or differentiation, or both, can be readily assessed by methods known in the art. Proliferation and differentiation assays can also indirectly measure cell survival.

In an exemplary proliferation assay, a cell composition containing neural stem and/or progenitor cells can be cultured under conditions in which clonal spheroid colonies, or "neurospheres," form. These neurospheres can be visualized and counted under a light microscope. Neurospheres can then be dissociated, and the culture continued, such that the number of secondary and subsequent neurospheres can be determined as an indication of proliferation. Conditions for culturing and dissociating neurospheres are described in Example III.

In other exemplary proliferation assays, the cells are assessed for their ability to incorporate $^3$H thymidine or bromodeoxyurine (BrdU, a thymidine analog), or assessed for their expression of proliferation markers, such as proliferating cell nuclear antigen (PCNA) or cdc2. Such proliferation assays are well known in the art and are described, for example, in Freshney, "Culture of Animal Cells: A Manual of Basic Technique" New York: Wiley-Liss, 4$^{th}$ ed. (2000).

Other types of proliferation assays suitable for determining whether a compound modulates neurogenesis are known in the art or can be determined using the guidance herein. The total number of cells, or number of labeled cells, observed in the presence of compound and in the absence of compound can be compared to determine if neurogenesis is modulated.

In an exemplary differentiation assay, cells are contacted with suitable primary antibodies specific for markers expressed by the type or types of cells it is desired to detect. Markers expressed by neural-stem and progenitor cells have been described above. As described in Example III, a marker for neurons is β-tubulin, a marker for astrocytes is GFAP, and a marker for oligodendrocytes is O4. Other markers specific for cells of various neural lineages are known in the art, and antibodies thereto are commercially available or can be generated by known methods.

Unless the primary antibody is labeled, the cells are then generally contacted with labeled secondary antibodies, such as enzymatically or fluorescently labeled antibodies, and the cells visualized or sorted. Methods to immunolabel cells, as well as methods to detect and sort immunolabeled cells, are well known in the art and described, for example, in Freshney, supra (2000). The types and numbers of cells of each lineage of interest observed in the presence of compound and in the absence of compound can be compared to determine if neurogenesis is modulated.

Neurogenesis assays can be performed in vivo in a human or other mammal, vertebrate or invertebrate, as described above. Such assays are generally similar to ex vivo assays, except that the tissue of interest is generally fixed and sectioned prior to detection of the label or marker of interest. Example IV describes a method of labeling proliferating cells in vivo with BrdU and subsequently detecting BrdU-labeled cells, and cells expressing neural stage-specific differentiation markers, by immunohistochemistry.

Alternatively, and particularly where the human or animal is not sacrificed, detection of proliferation and differentiation markers can be done using radiolabeled antibodies and non-invasive imaging methods known in the art, such as single photon emission computed tomography (SPECT) and positron emission tomography (PET).

For in vivo applications, various delivery methods can be used to contact neural stem or progenitors within the tissue of interest with a compound, as described in more detail below with respect to therapeutic applications. The delivery method will depend on factors such as the tissue of interest, the nature of the compound (i.e. its stability and ability to cross the blood-brain barrier), and the duration of the experiment. As described in Example IV, for delivery of peptides and BrdU to the brain over a period of several weeks, an osmotic minipump can be implanted into a neurogenic region, such as the lateral ventricle. Alternatively, compounds can be administered by direct injection into the cerebrospinal fluid of the brain or spinal column, or into the eye. Compounds can also be administered into the periphery (such as by intravenous or subcutaneous injection, or oral delivery), and subsequently cross the blood-brain barrier.

Advantageously, in vivo methods allow the effect of compounds to be tested for their effect on neurogenesis both in normal subjects and in subjects having neural damage and disease. Either human subjects or experimental animal models can be used.

Experimental animal models of trauma due to stroke or neural injury are known in the art. One experimental model of stroke involves occluding the right middle cerebral artery and both common carotid arteries of rats for a short period, followed by reperfusion (Moore et al., *J. Neurochem.* 80:111-118). An experimenal model of CNS injury is the fluid percussion injury (FPI) model, in which moderate impact (1.5-2.0 atm) is applied to the parietal cerebral cortex (Akasu et al., *Neurosci. Lett.* 329:305-308 (2002). Experimental models of spinal cord injury are also used in the art (Scheifer et al., *Neurosci. Lett.* 323:117-120 (2002). Suitable models for neural damage due to oxidative stress, hypoxia, radiation and toxins are also known in the art.

Experimental animal models of human neurodegenerative diseases are also known in the art. Various experimental models of Alzheimer's disease are reviewed in Janus, *Physiol. Behav.* 73:873-886 (2001); models of Parkinson's disease are reviewed in Tolwani et al., *Lab. Anim. Sci.* 49:363-371 (1999); models of Huntington's disease are reviewed in Menalled et al., *Trends Pharmacol. Sci.* 23:32-39 (2002); and a SOD-1 transgenic model of amyotrophic lateral sclerosis is described in Ripps et al., *Proc. Natl. Acad. Sci. USA* 92:689-693 (1995). Other animal models for human neural degenerative diseases, including those described below with respect to therapeutic applications, are known in the art.

Experimental animal models of retinal neurogenesis are described, for example, in Marcus et al., *Visual Neurosci.* 16:417-424 (1999).

Experimental animal models of demyelinating diseases, such as experimental autoimmune encephalomyelitis (a model of multiple sclerosis), are also known in the art.

In any of the in vivo assays, neurogenesis in the presence of compound and in the absence of compound can be compared to determine if the compound modulates neurogenesis. Such in vivo assays can further provide evidence of safety, toxicity, pharmacokinetics and therapeutic efficacy of the compound of interest in preparation for human therapeutic use.

The compounds of the invention that modulate neurogenesis can be used directly as therapeutic agents to prevent or treat a variety of disorders of the nervous system in which it is beneficial to promote or inhibit neurogenesis. The compounds of the invention can also be used to promote neurogenesis ex vivo, such that a cell composition containing neural stem cells, neural progenitor cells, and/or more differentiated neural cells can subsequently be administered to an individual to prevent or treat the same indications.

Nervous system disorders that can be treated with the compounds of the invention include, but are not limited to, nervous system injuries, and diseases or disorders which result in either a disconnection of axons, a diminution or degeneration of neurons, or demyelination. Such diseases and disorders include, for example, the following lesions of the central nervous system (including spinal cord and brain) or peripheral nervous systems:

(1) ischemic lesions, in which a lack of oxygen in a portion of the nervous system results in neuronal injury or death, including cerebral infarction or ischemia, or spinal cord infarction or ischemia;

(2) traumatic lesions, including lesions caused by physical injury or associated with surgery, for example, lesions which sever a portion of the nervous system, or compression injuries;

(3) malignant lesions, in which a portion of the nervous system is destroyed or injured by malignant tissue which is either a nervous system associated malignancy or a malignancy derived from non-nervous system tissue;

(4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis;

(5) degenerative lesions, in which a portion of the nervous system is destroyed or injured as a result of a degenerative process including but not limited to, degeneration associated with Parkinson's disease, Alzheimer's disease, Huntington's chorea, amyotrophic lateral sclerosis (ALS) and retinal degeneration;

(6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(7) neurological lesions associated with systemic diseases including, but not limited to, diabetes (diabetic neuropathy, Bell's palsy), systemic lupus erythematosus, carcinoma, or sarcoidosis;

(8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

Because neurogenesis is involved in learning and memory, compounds of the invention can also be used in normal individuals to enhance learning and/or memory, or to treat individuals with defects in learning and/or memory.

Other conditions that can be beneficially treated with compounds that modulate neurogenesis are known in the art (see, for example, U.S. published application 20020106731).

It is expected that the compounds identified by the methods described herein as compounds that modulate PKR signaling and further modulate neurogenesis will have beneficial activities in addition to modulating neurogenesis. For example, PKR1 and/or PKR2 are expressed on a variety of tissues apart from the neural tissues described herein. Modulation of PKR signaling has been proposed to be beneficial to treat conditions relating to these tissues, such as disorders of gastrointestinal motility (see U.S. 20020115610A1), circadian rhythm (Cheng et al., *Nature* 417:405-410 (2002)) and angiogenesis (LeCouter et al., supra (2001)).

Stem cells have the ability to divide for indefinite periods in culture and to give rise to specialized cells. The fertilized egg is totipotent, meaning that its potential is total. After several cycles of cell division, these totipotent cells begin to specialize, forming a hollow sphere of cells, called a blastocyst. The cells of the inner cell mass of the blastocyst are pluripotent, and will go on to form many but not all types of cells necessary for fetal development. The pluripotent stem cells undergo further specialization into stem cells that are committed to give rise to cells that have a particular function. These cells are called multipotent stem cells. Examples of multipotent stem cells include hematopoietic stem cells, which give rise to red blood cells, white blood cells and platelets; hepatic stem cells, which differentiate into hepatocytes and biliary epithelial cells; myogenic stem cells, which differentiate into muscle; and neural stem cells described above. Multipotent stem cells have been identified in many other organs and tissues, including lung, heart, prostate, skin and gastrointestinal tract.

Because neural stem cells share certain features with other types of stem cells, such as certain surface markers (see, for example, Klassen et al., *Neurosci. Lett.* 312:180-182 (2001); Hunziker et al., *Biochem. Biophys. Res. Commun.* 271:116-119 (2000)), as well as the ability to self-replicate and differentiate, it is expected that signaling through prokineticin receptors, disclosed herein to be implicated in neurogenesis, is also important in modulating proliferation and differentiation of pluripotent and other multipotent stem cells. Accordingly, the methods described herein for identifying and using compounds that modulate neurogenesis can be readily applied to identifying and using compounds that modulate proliferation and differentiation of other stem cells in ex vivo and in vivo applications known in the art.

Those skilled in the art can determine other useful applications for compounds that modulate PKR signaling.

Compounds of the invention that modulate neurogenesis can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the ex vivo and in vivo neurogenesis assays described herein.

The total amount of a compound can be administered as a single dose or by infusion over a relatively short period of time, or can be administered in multiple doses administered over a more prolonged period of time. Additionally, the compound can be administered in a slow-release matrix, which can be implanted for systemic delivery at or near the site of the target tissue. Contemplated matrices useful for controlled release of compounds, including therapeutic compounds, are well known in the art, and include materials such as DepoFoam™, biopolymers, micropumps, and the like.

The invention compounds can be administered to a mammal by a variety of routes known in the art including, for example, intracerebrally, intraspinally, intravenously, intramuscularly, subcutaneously, intraorbitally, intracapsularly, intraperitoneally, intracisternally, intra-articularly, orally, intravaginally, rectally, topically, intranasally, or transdermally.

Generally, the invention compounds are administered to an animal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or detrains; antioxidants, such as ascorbic acid or glutathione; chelating agents; and low molecular weight proteins (see for example, "Remington's Pharmaceutical Sciences" 18th ed., Mack Publishing Co. (1990)).

For applications that require the compounds to cross the blood-brain barrier, or to cross cell membranes, formulations that increase the lipophilicity of the compound can be useful. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Other approaches for formulating a compound such that it crosses the blood-brain barrier are known in the art and include the use of nanoparticles, which are solid colloidal particles ranging in size from 1 to 1000 nm (Lockman et al., Drug Dev. Ind. Pharm. 28:1-13 (2002)), and peptides and peptidomimetics that serve as transport vectors (Pardridge, *Nat. Rev. Drug Discov.* 1:131-139 (2002).

Although drug delivery to the central nervous system poses unique challenges, the CNS is also a site of immune privilege. Thus, a compound that could elicit an immune response that precludes its use for many indications can still be an effective therapeutic if delivered into the CNS. Accordingly, compounds that are potentially immunogenic, such as chimeric prokineticin peptides, prokineticins from other species, and certain other PKR modulatory compounds, can be used as effective therapeutics to modulate neurogenesis in humans.

Besides peptides and compounds identified in drug screens, PKR modulatory compounds described herein include nucleic acid molecules that encode prokineticins or prokineticin receptors, as well as ribozymes, antisense molecules, RNAi and the like. Methods of formulating and delivering nucleic acid molecules to individuals for therapeutic use are known in the art. Useful vectors for delivering therapeutic nucleic acid molecules to the CNS include, for example, herpes simplex virus vectors, adenoviral vectors, VSV-G-pseudotyped retroviral vectors and adeno-associated viral vectors. Methods for delivering nucleic acid molecules to the CNS are reviewed, for example, in Hsich et al., *Hum. Gene Ther.* 13:579-604 (2002).

Cells that have been contacted with PKR modulatory compounds, including neural stem and progenitor cells, more differentiated cells, and genetically modified cells expressing PK, can be used in therapeutic applications described herein. Methods of formulating and delivering cells to individuals for therapeutic use are known in the art (see, for example, reviews by Cao et al., *J. Neurosci. Res.* 68:501-510 (2002), and Park et al., *Gene Ther.* 9:613-624 (2002)).

To enhance the modulation of neurogenesis, more than one therapeutic approach or composition can be provided to an individual or used ex vivo. For example, a compound that modulates PKR signaling can be used in conjunction with neurogenic growth factors, such as EGF and FGF, or in conjunction with conventional therapies for the disorder or condition being treated. The skilled clinician will be able to determine appropriate concurrent or sequential therapies for use in conjunction with the compounds-and methods of-the invention.

As described herein, PKR1, PKR2 and PK2 are expressed on cells within regions of the brain and retina that are neurogenically active. Accordingly, molecules that specifically bind these polypeptides can be used in either ex vivo or in vivo applications to label neurogenically active cells or regions. Molecules that specifically bind PKRs and PKs include their cognate ligands and receptors, respectively, as well as antibodies and binding compounds identified in the assays described herein.

Thus, the invention provides a method of labeling neural cells, by contacting a mixed cell population, tissue or animal with a ligand that binds a PKR or a PK, and detecting binding of said ligand to a cell within said population, tissue or animal.

The use of prokineticins and prokineticin receptors as markers is particularly advantageous in cases in which these markers are more abundant or more selective for particular cell types than other markers currently used to identify neural cells, such as the markers described above. The labeling method can be used in a variety of research and clinical applications, such as in identifying and distinguishing different types of cells, in diagnosing neural disorders, and in monitoring the efficacy of therapies with neurogenic agents. The skilled person can determine other useful applications for the compounds and methods described herein.

The following examples are intended to illustrate but not limit the present invention.

EXAMPLE I

This example shows the expression of prokineticin 2 (PK2), prokineticin receptor 1 (PKR1) and prokineticin receptor 2 (PKR2) in regions of the brain with high neurogenic activity.

In situ hybridization analysis of PKR1, PKR2 and PK2 mRNA expression in mouse brain was performed according to the following method. Antisense and sense riboprobes were generated containing the coding region of mouse PK2 (accession number AF487280; nucleotides 1-528) or the 3'UTR (untranslated region) of mouse PKR2 (accession number AF487279; nucleotides 1147-2211) or the 3'UTR of mouse PKR1 (accession number AF487278; nucleotides 1208-2183). The 3'UTR of PKR1 and PKR2 were used to distinguish the repsective mRNAs since these receptors are over 80% identical at the nucleic acid sequence level in their coding regions. The riboprobes were generated using T7 or SP6 RNA polymerases and were radioactively labeled with $^{35}$S-UTP. Probes were used at a concentration of $1\times10^{7}$ cpm/ml.

Brains from adult C57B16 male mice were quickly removed and frozen in isopentane at −20° C. for 30 sec. Twenty-micrometer coronal or saggittal sections were cut on a cryostat and serial sections were collected. Tissue sections were processed for in situ hybridization according to the method described in Cheng et al., *Nature* 417:405-410 (2002). Briefly, tissue sections were pretreated with proteinase K, hybridized with the riboprobe for 18 hours at 60° C., followed by RNAse digestion, high stringency washes and dehydration. Tissue sections were then exposed to BioMax film (Kodak) for 3-4 days. The mRNA distributions were analyzed in autoradiograms and emulsion-dipped sections. Specific hybridization signals were quantitatively analyzed by comparing to $^{14}$C-standards of known radioactivity using a video-based computer image analysis system (MCID, Imaging Research, St. Catharine's, Ontario, Canada). A calibration curve of optical density versus radioactivity (dpm/mg tissue wet weight) was constructed using $^{14}$C-standards. Autoradiographic images were captured using MCID, and emulsion-dipped brain images were taken under the transillumination microscope (BX50, Olympus) by using Spot camera software version 2.2.2 (Diagnostic Instruments, Sterling Heights, Mich.). Figures were prepared by using Adobe Photoshop (version 5.5).

In situ hybridization of adult mouse brain section with PKR1 and PKR2 probes revealed that PKR1 and PKR2 mRNAs are expressed in the subventricular zone (SVZ) of the lateral ventricle, olfactory bulb, olfactory ventricle, and dentate gyrus of hippocampus, which are all regions that have been shown to have neurogenic activity in adult brains. Quantification indicated that the highest levels of both PKR1 and PKR2 mRNAs are in the regions of olfactory bulb/olfactory ventricle, followed by the SVZ of lateral ventricle and the dentate gyrus of hippocampus. Thus, the expression level of PKR1 and PKR2 mRNAs correlate with the level of neurogenic activity in the adult brain.

Expression of PK2, one of the ligands that can activate PKR1 and PKR2, was also detected in the olfactory bulb, the brain region that has the highest neurogenic activity. PK2 mRNA is also expressed in the dentate gyrus of hippocampus.

The expression of prokineticin ligand and receptors in regions of adult brain that have neurogenic activity indicates that prokineticins and prokineticin receptors are important signaling molecules that modulate neurogenisis in the nervous system. Thus, compounds that modulate prokineticin receptor signaling can be used therapeutically in applications in which it is desired to promote or inhibit neurogenesis.

EXAMPLE II

This example shows expression of PKR2 mRNA in adult retina.

Retinas of adult mice were processed for immunohistochemistry as described in Example I, using a PKR2 3'UTR riboprobe. Expression of PKR2 mRNA was observed in the retina, and particularly in the inner nuclear layer of the retina.

During retinogenesis, seven principal retinal cell types are known to derive from a common population of multipotent retinal progenitor cells (RPCs) residing in the inner layer of the optic cup (Marquardt et al., *Trends Neurosci.* 25:32-38 (2002). The inner nuclear layer, or layer 6, is the presumptive location of multipotent stem cells in the adult retina.

The expression of PKR2 in the inner nuclear layer of the retina is consistent with a role for PKR signaling in retinal neurogenesis. Thus, compounds that modulate prokineticin receptor signaling can be used therapeutically in applications in which it is desired to promote or inhibit neurogenesis in the retina.

EXAMPLE III

This example shows a method of contacting neural stem cell or precursor cells ex vivo with prokineticins and assessing the effect on neurogenesis.

Neural stem cell cultures are established from the lateral walls of the lateral ventricles of adult mice under conditions in which they form clonal spheroid colonies, referred to as neurospheres (Reynolds and Weiss, *Science* 255:1707-1710 (2002)). The neural stem cells are then cultured under nine different conditions: in the presence of EGF, FGF2, PK1, PK2, EGF+PK1, FGF2+PK1, EGF+PK2, FGF+PK2, or without growth factor. The total number of neurospheres in the six different culture conditions are counted after 5 days in vitro, and the average number of neurospheres from five independent experiments are calculated. In each independent experiment, 300,000 lateral ventricle wall cells from four animals are divided between the nine different conditions. According to previous reports, no neurospheres or some very small spheres are detected in the cultures without supplemented growth factor. In addition to the number, the morphology of the neurospheres is scored for their size and appearance. The possible synergistic effects of PK and EGF and/or FGF2 are also determined.

The neurosphere-forming cells are then tested under the different conditions to determine if they have self-renewal capacity and whether cells expanded under one condition could be propagated in another growth factor. The neurospheres are dissociated after 8 days in vitro, and each culture grown in a single growth factor are divided into two halves; one half continues to grow in the same growth factor as before the passage, and the other half is grown in the other growth factor. The neurospheres grown in both growth factors continue to grow in both growth factors, and the neurospheres grown without growth factor continued without growth factor. Five days after passage, the total number of neurospheres are counted from five independent experiments.

To prepare primary neuronal cells, four- to eight-month-old CD-1 albino mice are anesthetized by intraperitoneal injection of pentobarbital (120 mg/kg) and killed by cervical dislocation. The brains are removed and placed in artificial cerebrospinal fluid (aCSF) (124 mM NaCl, 5 mM KCl, 1.3 mM $MgCl_2$, 0.1 mM $CaCl_2$, 26 mM $NaHCO_3$, and 10 mM D-glucose, pH 7.3) aerated with 95% $O_2$/5% $CO_2$ at room temperature. Subependyma are isolated after coronal sectioning and cut into 1 $mm^3$ pieces. Pieces are transferred into 30 ml of aCSF containing 1.3 mg/ml trypsin (Type XII, 9000 BASF units/mg; Sigma, St. Louis, Mo.), 0.67 mg/ml hyaluronidase (2000 units/mg; Sigma), and 0.2 mg/ml kynurenic acid (Sigma) and incubated, under continuous oxygenation and stirring, for 90 min at 32-34° C. Tissue sections are then rinsed in aCSF for 10 min, transferred to DMEM/F12 medium (1:1 v/v; Life Technologies, Gaithersburg, Md.) containing 0.7 mg/ml ovomucoid (Sigma), and carefully triturated with a fire-polished Pasteur pipette. The cells are collected by centrifugation and resuspended in growth factor-free, chemically defined DMEM/F12 medium containing 2 mM L-glutamine, 0.6% glucose, 9.6 gm/ml putrescine, 6.3 ng/ml progesterone, 5.2 ng/ml sodium selenite, 0.025 mg/ml insulin, 0.1 mg/ml transferrin, and 2 µg/ml heparin (sodium salt, grade II; Sigma) (control medium).

Cells prepared as described above are plated into 35 mm Petri dishes (Corning, Corning, N.Y.) containing control medium with growth factors (GF; either FGF2 (human recombinant, 20 ng/ml; Peprotech, Rocky Hill, N.J., or Upstate Biotechnology, Lake Placid, N.Y.), EGF (human recombinant, 20 ng/ml; Peprotech)), or recombinant human PK1 or PK2 (10 nM, or 10 ng/ml). The medium is changed every 3-4 d.

For population analyses, primary cells are plated at 3500 cells/$cm^2$, and the spheres formed after 8-10 d are harvested, collected by centrifugation (10 min at 800×g), mechanically dissociated to a single-cell suspension, and replated in medium containing the appropriate GF(s). This procedure is repeated every 8-10 d in vitro (DIV) for up to 6 months. The total number of viable cells is assessed at each passage by trypan blue exclusion and confirmed by the calcein/propidium iodide technique.

To assess stem-like cell numbers in primary cultures, culture conditions are established that allow quantitative determination of the number of stem-like cells plated on a dish that are responsive to EGF, FGF2, or recombinant human PK2. The methodology has been developed for adult neural stem cells (Gritti et al., *J. Neurosci.* 16:1091-1100 (1996))), and is modified from the classical assay for assessing the type and number of clonogenic cells isolated from various hemopoietic tissues (Bodine et al., *Blood* 15;78: 914-920(1991); Bodine et al., *Blood* 79:913-919 (1992)). Subventricular tissues are dissociated to a suspension of single cells that are embedded in a methylcellulose gel matrix (1.5% final concentration; Dow Methocell A4 M, premium grade) to prevent aggregation, plated at a final density of <10 viable cells/cm², and cultured in the presence of the appropriate GF until spherical clones are formed (8-10 DIV). Counting the number of spheres formed in the presence of FGF2, EGF, or recombinant PK1 or PK2 yields the number of stem cells plated, which can proliferate under the conditions tested. To assess the number of single cells, doublets, and triplets in these cultures, samples are seeded onto glass coverslips and the cell nuclei, counterstained with 4',6-diamidino2-phenylindole dihydrochloride (DAPI; 1 mg/ml in methanol; 15 min at 37° C.), are counted.

At every other subculturing step and after a growth factor switch, an aliquot of the cells is withdrawn from culture, and clonal spheres are generated by embedding dissociated single cells in methylcellulose and plating at a clonal density (<1 cell/cm²) in the presence of the appropriate GF. Clonal spheres are used to assay for self-renewal capacity and multipotentiality, in serial subcloning experiments. For self-renewal, individual spheres are collected by micromanipulation, dissociated to a single-cell suspension, embedded in methylcellulose, and replated as described above for primary cultures in medium containing the appropriate GF(s). The number of spheres generated under the various conditions is assessed after 8-10 d and normalized by the total number of cells plated into each well, as determined by direct observation 30 min after plating.

Retention of multipotentiality by stem cells after GF switches is assessed as follows. A single-cell suspension is prepared, and individual cells selected under high-power magnification, transferred into a single well by micromanipulation, and grown in isolation (1 cell/well). A mark is notched on the well to facilitate identification of the field, and microphotographs are taken at the appropriate intervals. After a clonal sphere is formed, it is further subcultured and expanded, and the progeny generated plated onto multiple glass coverslips, differentiated, and processed for multiple immunocytochemistry, as described below.

Multiple immunofluorescence assays are performed as follows. Freshly dissociated cells from subependymal tissue (1000 cells/cm²) and serially passaged clonal spheres are plated onto polyornithine-coated glass coverslips. For differentiation experiments, cells are plated in GF-free culture medium for 5 d, followed by the addition of fetal bovine serum for a further 2-5 DIV. Primary or differentiated cultures are fixed (20 min) with 4% paraformaldehyde in PBS, pH 7.4, and rinsed three times with PBS. The coverslips are then incubated for 90 min at 37° C. in PBS containing 10% normal goat serum (NGS), 0.3% Triton X-100, and the appropriate primary antibodies or antisera. After thorough washing with PBS and 10% NGS, cells are reacted for 45 min (room temperature) with secondary fluorescein isothiocyanate- or rhodamine isothiocyanate-conjugated goat anti-mouse or anti-rabbit IgG antibodies (1:100; Boehringer Mannheim, Indianapolis, Ind.) or with donkey anti-mouse IgM antibodies coupled to 7-amino-4-methylcoumarin-3-acetic acid (1:100; Jackson ImmunoResearch, West Grove, Pa.). The coverslips are rinsed three times in PBS and once in distilled water and mounted on glass slides with Fluorsave (Calbiochem, La Jolla, Calif.). After immunostaining, coverslips are counterstained with DAPI.

The primary antibodies or antisera used are mouse monoclonal anti-microtubule-associated protein-2 (MAP2; IgG; 1:100; Boehringer Mannheim), anti-tau-microtubule-associated protein (IgG; 1:100; Boehringer Mannheim), anti-β-tubulin (IgG; 1:1250; Sigma), anti-galactocerebroside (GalC; IgG; 1:50; Boehringer Mannheim), anti-O4 (IgM;.1:200; Boehringer Mannheim) and rabbit antisera against glial fibrillary acidic protein (GFAP; ready to use; Incstar). Samples are viewed and photographed with an inverted Nikon Axiophot fluorescence microscope.

EXAMPLE IV

This example shows a method of contacting neural stem cell or precursor cells in vivo with prokineticins and assessing the effect on neurogenesis.

Recombinant prokineticins are administered to rat brains by intracerebroventricular (ICV) injection, and neurogenesis is examined. The procedure for infusing recombinant PK1 and PK2 is as follows. Adult Sprague-Dawley rats are anesthetized with ketamine and implanted with an osmotic minipump (Alzet 2002; Alza Scientific Products, Palo Alto, Calif.), as described in Cheng et al., Nature 417:405-410 (2002). The cannula are placed in the right lateral ventricle 4.0 mm deep to the pial surface and +0.0 mm anteroposterior relative to the bregma and 1.8 mm lateral to the midline. Each rat is infused for 14 d with 10 µl/d of either human recombinant prokineticin 1 or prokineticin 2 dissolved in 0.1 M PBS (1 µg/ml), or PBS only. To label the newly generated cells in the prokineticin- or vehicle-infused brains, the cell proliferation marker BrdU is delivered at the same rate (12 µg/d) and through the same minipump as prokineticin or PBS. After the cessation of the infusion of prokineticins and BrdU or PBS and BrdU, the cannula remains in the lateral ventricle, and the animals are allowed to survive another 16 d before perfusion.

To determine whether the ICV infusion of recombinant prokineticins modulates neurogenesis, the distribution and number of newly generated cells in the forebrain after the administration of human prokineticin 1 or 2 (n=3) are examined and compared with results following administration of the control vehicle, 0.1 M PBS, given alone (n=3). Areas that are examined include subventricular zone (SVZ) of the lateral ventricle, olfactory bulb, olfactory ventricle, dentate gyrus of hippocampus, cortical areas, and other regions of the brain where neuronal proliferation, differentiation or migration occur, or where PKR1 or PKR2 are expressed.

Sixteen days after the cessation of intracerebroventricular administration of compounds, the animals are anesthetized with pentobarbital (50 mg/kg) and perfused transcardially with 4% paraformaldehyde in 0.1 M phosphate buffer, pH 7.4. Brains are cryoprotected with 30% sucrose in 0.1 M phosphate buffer, pH 7.2, embedded in Tissue-Tek OCT compound (Sakura Finetek, Torrance, Calif.), and sectioned on a cryostat in the coronal plane at 20 µm.

To reveal newly generated BrdU-positive cells, the sections are incubated for 30 min in 1N HCl at 60° C. to denature the DNA. Subsequently, the sections are incubated first in blocking serum (10% normal goat serum in 0.1 M phosphate buffer containing 0.02% Triton X-100, pH 7.4; abbreviated as NGS) for 1 hr, and then for 48 hr with a 1:200 dilution of a mouse IgG anti-BrdU (Accurate Chemicals, Westbury, N.Y.) in NGS. For fluorescent visualization of BrdU-labeled cells, the sections are incubated for 1 hr at room temperature in a rhodamine-conjugated goat anti-rat secondary antibody (1:200 dilution).

Some sections are processed to visualize only BrdU-labeled cells, whereas others are double-labeled with anti-BrdU, as well as an antibody to a cell type-specific marker to determine the phenotype of the newly generated cells. To identify neurons, the antibody TuJ1 (1:400) (Covance, Richmond, Calif.) is used, which is a mouse polyclonal IgG that recognizes neuron-specific βIII-tubulin (Lee et al., *Proc. Natl. Acad. Sci.* USA 87: 7195-7199 (1990)) usually expressed by immature neurons, or a monoclonal antibody to microtubule-associated protein-2 (MAP-2) (1:200; Roche Products, Indianapolis, Ind.), which recognizes more differentiated neurons (Bernhardt et al., *J. Neurosci.* 5:977-991 (1985)). A polyclonal antibody to glial fibrillary acidic protein (GFAP) (1:500 dilution; Dako, Glostrup, Denmark; Bignami et al., *Brain Res.* 43: 429-435 (1972)) is also used to identify astrocytes and a mouse monoclonal anti-myelin proteolipid protein (PLP) (Chemicon, Temecula, Calif.) at a 1:200 dilution (Cheng et al., *J. Neurosci.* 18:5673-5681 (1998)) used to identify oligodendrocytes. As a marker for undifferentiated cells, a mouse monoclonal antibody to the intermediate filament protein nestin (Hockfield and McKay, *J. Neurosci.* 5:3310-3328 (1985)); Frederiksen and McKay, *J. Neurosci.* 18:5673-5681 (1988)) is used as an undiluted supernatant (Developmental Studies Hybridoma Bank, Iowa City, Iowa).

For fluorescent visualization of all cell type-specific antibodies, fluorescein-conjugated secondary antibodies are used at a 1:200 dilution. All secondary antibodies are purchased from Jackson ImmunoResearch (West Grove, Pa.). The slides are coverslipped with VectaShield (Vector Laboratories, Burlingame, Calif.) and viewed using a Nikon Axiophot fluorescent microscope equipped with rhodamine and fluorescein filters, as well as a dual filter for visualizing rhodamine and fluorescein fluorescence simultaneously. For confirmation of the phenotype of individual BrdU+ cells, sections are also viewed using a confocal scanning laser microscope (Bio-Rad), as described in Bermak et al., *Nat. Cell Biol.* 3:492-498 (2001). To reveal the cytoarchitecture of the structures analyzed, some sections are dehydrated in ethanol, counterstained with cresyl violet, rehydrated, and coverslipped with DPX (BDH Laboratory Supplies, Poole, UK). All microscopic images are processed using Adobe Photoshop (Adobe Systems, Mountainview, Calif.).

The density of BrdU-labeled cells, expressed as cells per cubic millimeter, is determined in both the PK1 or PK2-infused and PBS-infused brains. Corresponding coronal sections exhibiting the same cytoarchitectonic features, determined using the rat atlas of Paxinos and Watson, are used for comparison. The counts are carried out, using a 40× objective, by-placing an optical grid (field size, 250×250 µm) starting from the wall of the lateral or third ventricle and proceeding into the parenchyma until BrdU+ cells are no longer detectable. The density of BrdU-labeled cells is calculated for each structure analyzed in every animal, and statistical analyses are performed using the Student's t test.

EXAMPLE V

This example shows that administration of prokineticin 2 results in increased neurogenesis in the adult rat brain.

To confirm that prokineticins modulate neurogenesis, recombinant human PK2 was administered via intracerebroventribular infusion into adult rat forebrain. The number of newly generated cells in the forebrain of male Sprague Dawley rats (3 months old) in comparison to control animals was then measured. The cell proliferation marker BrdU, which was used to label newly generated cells, was delivered by a single intraperitoneal injection (50 mg/Kg). Delivery of PK2 was accomplished using Alzet osmotic minipumps connected to ICV cannula via plastic tubing. The ICV cannula was placed in the right lateral ventricle 4.0 mm deep to the pial surface, +0.0 mm anteroposterior relative to bregma, and 1.8 mm lateral to the midline.

For acute studies, rats were infused for three or six days with either human PK2 (10 µM) dissolved in aCSF (artificial cerebrospinal fluid)or aCSF alone. Rats were euthanized by transcardial paraformaldehyde infusion. For chronic studies, rats were infused for about 14 days with either human PK2 dissolved in aCSF (10 µM) or aCSF alone, and were euthanized by transcardial paraformaldehyde infusion five weeks after of the start of ICV infusion.

Animals were anesthetized with pentobarbital (50 mg/kg) and perfused transcardially with 4% paraformaldehyde in 0.1 M phosphate buffer, pH 7.4. Brains were removed, post-fixed overnight in 4% paraformaldehyde, and transferred to 0.32 M sucrose. Sections (40 µm) were cut with a cryostat and stored at −20° C. in a cryoprotectant solution (glycerol, ethylene glycol, and 0.1 M phosphate buffer, pH 7.4, 3:3:4 by volume).

The following antibodies and final dilutions were used for immunostaining and detection: rat anti-BrdU (1:100, Accurate, Westbury, N.Y.), mouse anti-BrdU (1:400, Boehringer Mannheim, Indianapolis, Ind.), mouse anti-NeuN (1:20, clone A60 from Dr. R. Mullen, University of Utah, Salt Lake City, Utah), rabbit anti-S100 (1:5000, Swant, Bellinzona, Switzerland), biotinylated horse anti-mouse IgG (1:160, Vector Laboratories, Burlingame, Calif.), avidin-biotin-peroxidase complex (1:100, VECTASTAIN ELITE, VECTOR Laboratories), and donkey anti-rat-FITC, anti-mouse-Texas Red, and anti-rabbit-CY5 (all 1:300, Jackson ImmunoResearch, West Grove, Pa.).

For immunoperoxidase detection, free-floating sections were treated with 0.6% $H_2O_2$ in TBS (0.15 M NaCl and 0.1 M Tris-HCl, pH 7.5) for 30 min to block endogenous peroxidase. For DNA denaturation, sections were incubated for 2 hr in 50% formamide/2×SSC (0.3 M NaCl and 0.03 M sodium citrate) at 65° C., rinsed for 5 min in 2×SSC, incubated for 30 min in 2N HCl at 37° C., and rinsed for 10 min in 0.1 M boric acid, pH 8.5. Several rinses in TBS were followed by incubation in TBS/0.1% Triton X-100/3% normal horse serum (TBS-Ths) for 30 min and incubation with mouse anti-BrdU antibody in TBS-Ths overnight at 4° C. After being rinsed in TBS-Ths, sections were incubated for 1 hour with biotinylated horse anti-mouse antibody. With intermittent rinses in TBS, avidin-biotin-peroxidase complex will be applied for 1 hour, followed by peroxidase detection for 5 min (0.25 mg/ml DAB, 0.01% $H_2O_2$, 0.04% NiCl). BrdU-positive cells were quantified with unbiased counting methods.

For immunofluorescence, sections were treated for DNA denaturation as described above, followed by several rinses in TBS and incubation in TBS/0.1% Triton X-100/3% normal donkey serum (TBS-Tds) for 30 min. Primary antibodies were applied in TBS-Tds for 48 hours at +4° C., rinsed in TBS three times for 10 min, and blocked in TBS-Tds for 10 min. Antibodies were detected with donkey, rat, mouse, or rabbit coupled to FITC, Texas Red, or CY5 for 2 hours. Fluorescent signals were detected and processed by a confocal scanning laser microscope (Bio-Rad MRC1024, Hercules, Calif.) and Adobe Photoshop (Adobe Systems, Mountain view, Calif.).

Figure 7B:
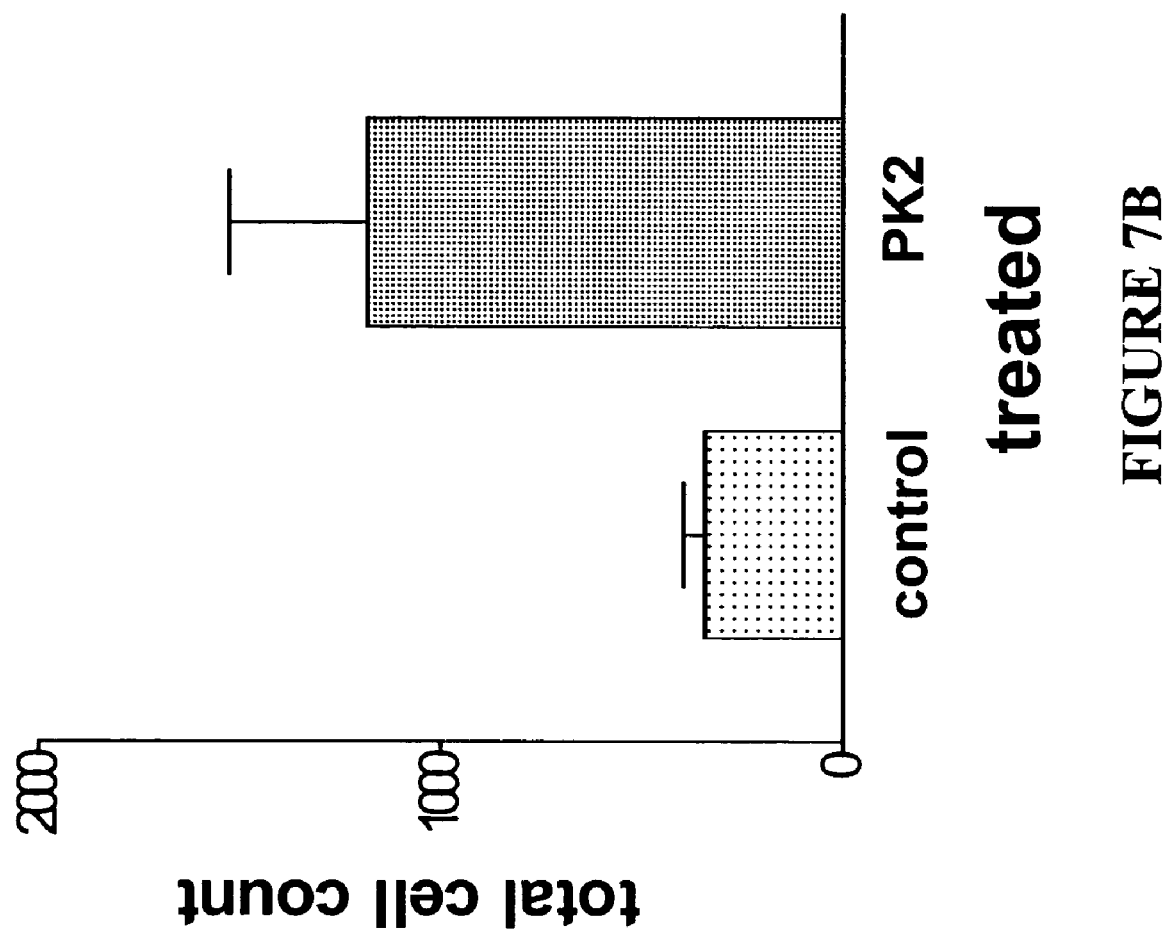
FIG. 7B shows quantification of BrdU-positive neurons from PK2-treated and control animals.

FIG. 7A shows representative images of BrdU immunofluorescence of neuroblasts of the subventricular zone (SVZ) in PK2-treated and control animals. FIG. 7B shows that PK2-treated animals had about 2.5-fold more BrdU-positive cells in their SVZ compared to control animals. These results indicate that acute administration of PK2 results in increased neurogenesis.

Figure 8:
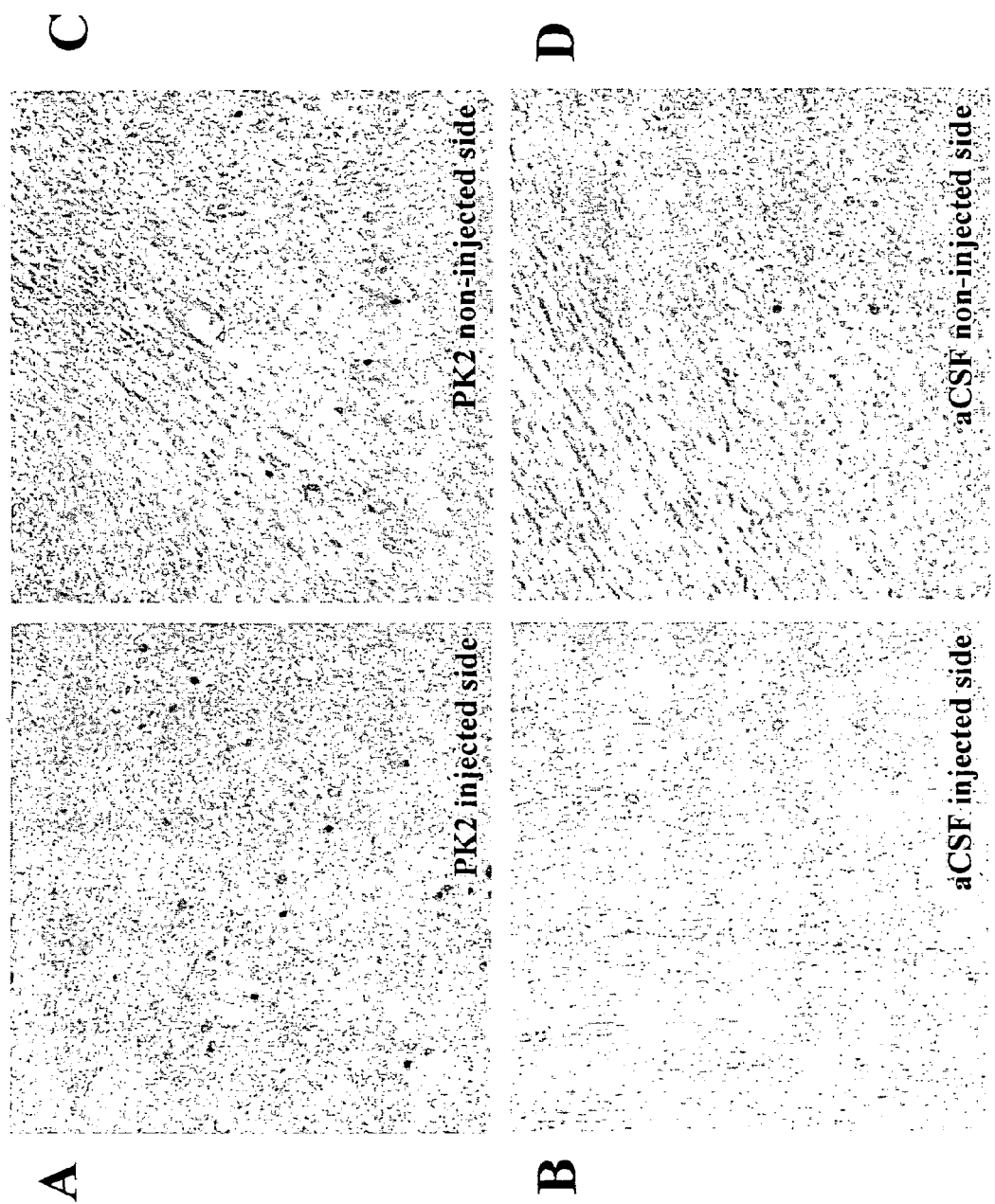
FIG. 8 shows representative images of BrdU staining of olfactory bulb (OB) neurons in animals treated chronically with PK2 and in untreated animals.
Figure 9:
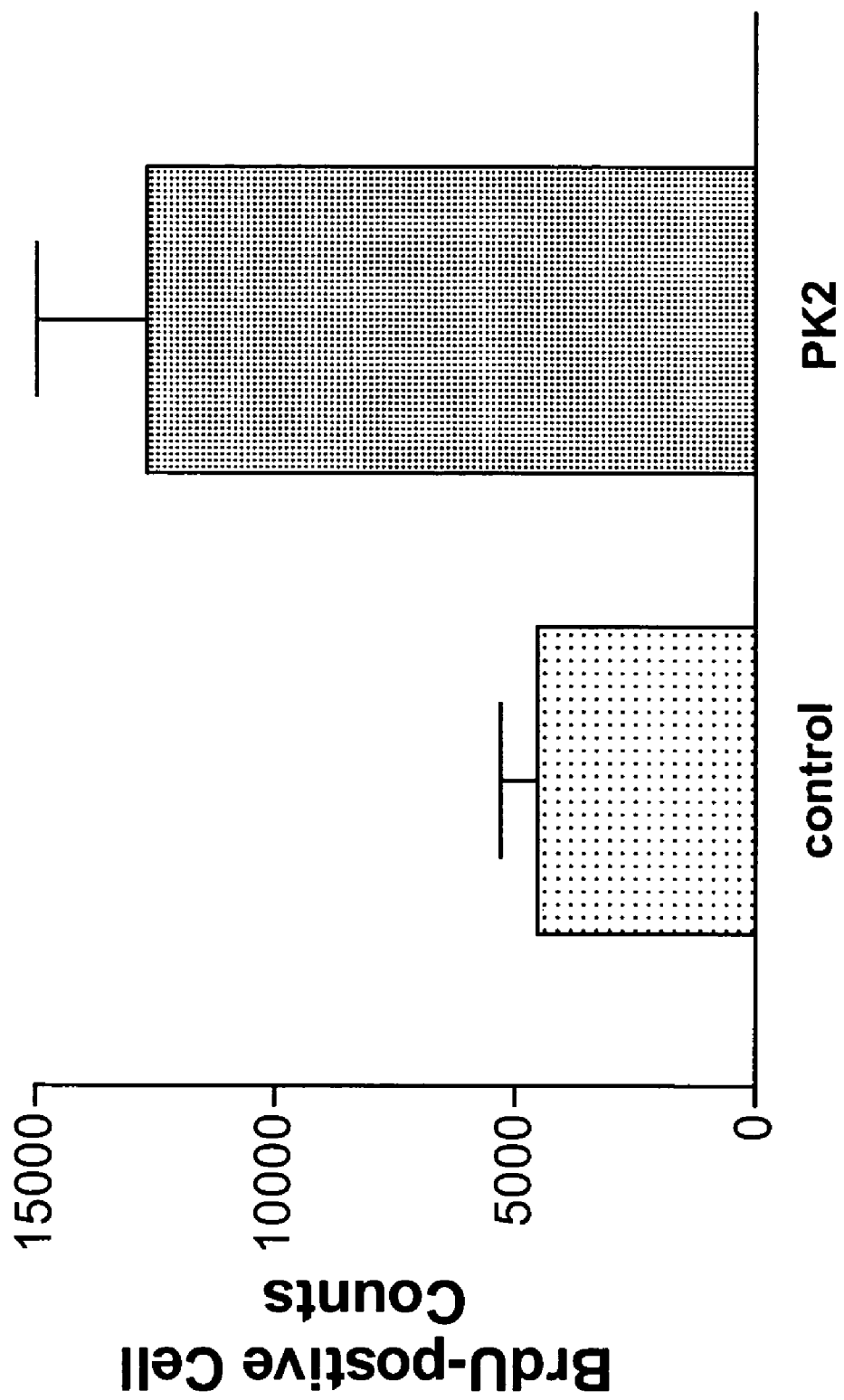
FIG. 9 shows quantification of BrdU-positive OB neurons in animals treated chronically with PK2 and in untreated animals.

FIG. 8 shows representative images of BrdU immunoperoxidase staining of olfactory bulb neurons from animals treated with PK2 after 5 weeks of treatment. FIG. 8A shows a greater number of newly generated neurons in tissue obtained from the side of the brain into which PK2 was injected in comparison to the number of newly generated neurons in tissue obtained from the untreated side of the brain (FIG. 8C) and in comparison to the number of newly generated neurons in control animals (FIGS. 8B and 8D). FIG. 9 shows quantification of BrdU-positive cells for PK2-treated and control animals, indicating that PK2-treated animals had about 2.5-fold more newly generated neurons than control animals. These results indicate that chronic administration of PK2 results in increased neurogenesis.

All journal article, reference, GenBank and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A method for modulating neurogenesis, comprising contacting a neural stem or progenitor cell with an effective amount of a prokineticin receptor (PKR) agonist compound wherein the PKR agonist is selected from the group consisting of SEQ ID NOS:5-11 and 14-15.

2. The method of claim 1, wherein the prokineticin agonist is SEQ ID NO:5 or SEQ ID NO:7.

3. The method of claim 1, wherein the cell is contacted ex vivo.

4. The method of claim 3, wherein the cell is a mammalian cell.

5. The method of claim 4, wherein the cell is a human cell.

6. The method of claim 1, wherein the neural stem or progenitor cell is contacted in vivo.

7. The method of claim 6, wherein the cell is a mammalian cell.

8. The method of claim 7, wherein the cell is a human cell.

9. The method of claim 8, wherein the human cell resides in an individual having a disorder of neural degeneration or damage.

* * * * *